United States Patent [19]
Ogawa et al.

[11] Patent Number: 5,498,609
[45] Date of Patent: Mar. 12, 1996

[54] BENZOAZEPINYL COMPOUNDS AS OXYTOCIN AND VASOPRESSIN ANTAGONISTS

[75] Inventors: Hidenori Ogawa; Kazumi Kondo; Hiroshi Yamashita; Keizo Kan; Michiaki Tominaga; Yoichi Yabuuchi, all of Tokushima, Japan

[73] Assignee: Otsuka Pharmaceutical Company, Limited, Tokyo, Japan

[21] Appl. No.: 211,887

[22] PCT Filed: Aug. 3, 1993

[86] PCT No.: PCT/JP93/01082

§ 371 Date: Apr. 20, 1994

§ 102(e) Date: Apr. 20, 1994

[87] PCT Pub. No.: WO94/04525

PCT Pub. Date: Mar. 3, 1994

[30] Foreign Application Priority Data

Aug. 20, 1992 [JP] Japan ..................................... 221359

[51] Int. Cl.$^6$ ..................... C07D 223/16; A61K 31/55
[52] U.S. Cl. ............................................. 514/213; 540/593
[58] Field of Search .............................. 540/593; 514/213

[56] References Cited

PUBLICATIONS

Boyer, S. et al. "The Synthesis of 1,3-Dihydro-1-[1-[(4-methyl-4H,6H-pyrrolo[1,2-a [4,1] benzoxazepin-4-yl)methyl]-4-piperidinyl]-2H-benzimidazol-2-one (1:1) Maleate (CG59443B, Potent Calmodulin Inhibitor)." J. Hetereocyclic Chem. 25, 1003–1005 (1988).

Roe E. T. et al. "Fatty Acid Amides. I. Preparation of Amides of Oleic and the 9,10-Dihydroxystearic Acids." J. Am. Chem. Soc. 71, 2215–2218 (1949).

Primary Examiner—Mukund J. Shah
Assistant Examiner—King L. Wong
Attorney, Agent, or Firm—Sughrue, Mion, Zinn, Macpeak & Seas

[57] ABSTRACT

Novel benzoheterocyclic compound of the formula (1):

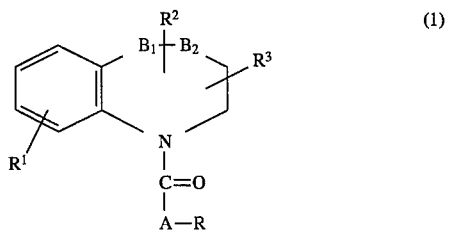

and pharmaceutically acceptable salts thereof, which show excellent anti-vasopressin activity and oxytocin antagonistic activity, and are useful as a vasopressin antagonist or oxytocin antagonist.

29 Claims, No Drawings

BENZOAZEPINYL COMPOUNDS AS OXYTOCIN AND VASOPRESSIN ANTAGONISTS

DESCRIPTION

1. Technical Field

The invention relates to novel benzoheterocyclic compounds which are useful as medicines.

2. Background Art

Various benzoheterocyclic compounds analogous to the compounds of the present invention have been known to have anti-vasopressin activities in European Patent Publication 0382185 (published on Aug. 16, 1990), WO 91/05549 (published on May 2, 1991), and EP-A-0470514 (published on Feb. 12, 1992). These known compounds are similar to the compounds of the present invention in the benzoheterocyclic nucleus of the chemical structure but are different from the compounds of the present invention in the substituent at 1-position and in the anti-vasopressin activities to some extent.

DISCLOSURE OF THE INVENTION

An object of the present invention is to provide benzoheterocyclic compounds of the formula (1):

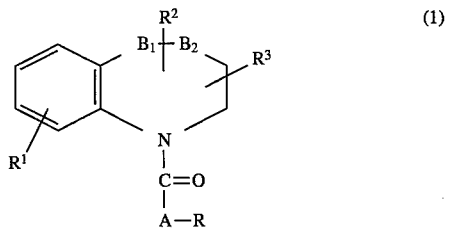

wherein $R^1$ is hydrogen atom or a halogen atom, $R^2$ is hydrogen atom, oxo group, a lower alkylidene group, hydroxy group, a lower alkoxy group, a lower alkenyloxy group, a hydroxy-substituted lower alkoxy group, a lower alkoxycarbonyl-substituted lower alkoxy group, a carboxy-substituted lower alkoxy group, a lower alkylsulfonyloxy-substituted lower alkoxy group, a phthalimide-substituted lower alkoxy group, a hydroxy-substituted lower alkyl group, a group of the formula: —O—D—(CO)$_I$NR$^4$R$^5$ (wherein D is a lower alkylene group, I is 0 or 1, $R^4$ and $R^5$ are the same or different and are hydrogen atom, a lower alkyl group, a lower alkanoyl group, a cycloalkyl group, or an amino-substituted lower alkyl group which may optionally have a lower alkyl substituent, or $R^4$ and $R^5$ may combine together with the nitrogen atom to which they bond to form a 5- or 6-membered saturated heterocyclic group which may be intervened or not with a nitrogen atom, an oxygen atom or a sulfur atom, wherein said heterocyclic group may optionally be substituted by a lower alkyl group or a lower alkanoyl group), a group of the formula: —E—(CO)$_I$NR$^6$R$^7$ (wherein I is the same as defined above, E is a lower alkylene group, $R^6$ and $R^7$ are the same or different and are hydrogen atom, a lower alkyl group, an amino-substituted lower alkyl group which may optionally have a lower alkyl substituent, or a lower alkanoyl group, or $R^6$ and $R^7$ may combine together with the nitrogen atom to which they bond to form a 5- or 6-membered saturated heterocyclic group which may be intervened or not with a nitrogen atom, an oxygen atom or a sulfur atom, wherein said heterocyclic group may optionally be substituted by a lower alkyl group, a lower alkanoyl group or a lower alkoxycarbonyl group), a lower alkanoyloxy-substituted lower alkyl group, a lower alkoxycarbonyl-substituted lower alkyl group, an amino which may optionally be substituted by a lower alkyl group or a cycloalkyl group, a carboxy-substituted lower alkyl group, a lower alkylsulfonyloxy-substituted lower alkyl group, a phthalimide-substituted lower alkyl group, an imidazolyl-substituted lower alkyl group, a 1,2,4-triazolyl-substituted lower alkyl group, an amino-substituted lower alkanoyloxy group which may optionally have a lower alkyl substituent, or an imidazolyl-substituted lower alkoxy group, $R^3$ is hydrogen atom, a lower alkoxy group or a hydroxy-substituted lower alkyl group, $B_1$ and B2 are each methylene group or a group of the formula: —NR$^8$— (wherein R$^8$ is hydrogen atom or a lower alkyl group), A is a 5- or 6-membered unsaturated heterocyclic residue having 1 to 2 heteroatoms selected from an oxygen atom, a nitrogen atom and a sulfur atom, and R is a group of the formula: —NHR$^A$ or a group of the formula:

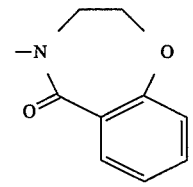

wherein $R^A$ is a group of the formula:

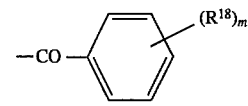

[wherein m is an integer of 1 to 3, $R^{18}$ is hydrogen atom, a lower alkyl group, a lower alkoxy group, a halogen atom, nitro group, a lower alkoxycarbonyl group, carboxy group, a lower alkoxycarbonyl-substituted lower alkoxy group, a hydroxy-substituted lower alkoxy group, a carboxy-substituted lower alkoxy group, a lower alkylsulfonyloxy-substituted lower alkoxy group, a phthalimide-substituted lower alkoxy group, or a group of the formula: —O—E—(CO)$_I$NR$^{19}$R$^{20}$ (wherein E and I are the same as defined above, $R^{19}$ and $R^{20}$ are the same or different and are hydrogen atom or a lower alkyl group, or $R^{19}$ and $R^{20}$ may combine together with the nitrogen atom to which they bond to form a 5- or 6-membered saturated heterocyclic group which may be intervened or not with a nitrogen atom or an oxygen atom, wherein said heterocyclic group may optionally be substituted by a lower alkyl group, or an amino group which may optionally be substituted by a lower alkanoyl group)], thienylcarbonyl group, a cycloalkylcarbonyl group or a phenyl-lower alkanoyl group which may optionally have a lower alkyl substituent on the phenyl ring, or a salt thereof.

The compounds of the formula (1) of the present invention and salts thereof show excellent vasopressin antagonistic activities, for examples, vasodilating activity, hypotensive activity, activity for inhibiting saccharide release in liver, activity for inhibiting growth of mesangium cells, water diuretic activity, platelet agglutination inhibitory activity, inhibitory activity for vomiting, and hence, they are useful as vasodilators, hypotensive agents, water diuretics, platelet agglutination inhibitor, etc., and are used in the prophylaxis or treatment of hypertension, edema, ascites, heart failure, renal function disorder, vasopressin parasecretion syndrome (SIADH), hepatocirrhosis, hyponatremia, hypokalemia, diabetic, circulation disorder, motion sickness, and the like. In addition, the compounds of the present invention and salts thereof show oxytocin antagonistic activities, for example, inhibitory effect on uterine smooth muscle constriction, inhibitory effect on milk secretion, inhibitory effect on synthesis and secretion of prostaglandin, and vasodilation activity, and hence, are useful in the protection or treatment of oxytocin-associated diseases, especially premature delivery, dysmenorrhea, endometritis, or in stopping labor preparatory to Caesarian delivery. Besides, the compounds of the present invention and salts thereof are characteristic in less side effects, and in prolonged action for a long time in living body.

Each group in the above formula (1) specifically includes the following groups.

The "lower alkoxy group" includes a straight chain or branched chain alkoxy group having 1 to 6 carbon atoms, for example, methoxy, ethoxy, propoxy, isopropoxy, butoxy, t-butoxy, pentyloxy, hexyloxy, and the like.

The "lower alkyl group" includes a straight chain or branched chain alkyl group having 1 to 6 carbon atoms, for example, methyl, ethyl, propyl, isopropyl, butyl, t-butyl, pentyl, hexyl, and the like.

The "halogen atom" includes fluorine atom, chlorine atom, bromine atom, and iodine atom.

The "lower alkylene group" includes a straight chain or branched chain alkylene group having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, and the like.

The "hydroxy-substituted lower alkoxy group" includes a straight chain or branched chain alkoxy group having 1 to 6 carbon atoms which is substituted by 1 to 3 hydroxy groups, for example, hydroxymethoxy, 2-hydroxyethoxy, 1-hydroxyethoxy, 3-hydroxypropoxy, 2,3-dihydroxyethoxy, 4-hydroxybutoxy, 3,4-dihydroxybutoxy, 1,1-dimethyl-2-hydroxyethoxy, 5-hydroxypentyloxy, 6-hydroxyhexyloxy, 2-methyl-3-hydroxypropoxy, 2,3,4-trihydroxybutoxy, and the like, The "lower alkanoyl group" includes a straight chain or branched chain alkanoyl group having 1 to 6 carbon atoms, for example, formyl, acetyl, propionyl, butyryl, isobutyryl, pentanoyl, t-butylcarbonyl, hexanoyl, and the like.

The "carboxy-substituted lower alkyl group" includes a carboxyalkyl group wherein the alkyl moiety is a straight chain or branched chain alkyl group having 1 to 6 carbon atoms, for example, carboxymethyl, 2-carboxylethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl, and the like.

The "5- or 6-membered saturated heterocyclic group which is formed by combining the groups $R^4$ and $R^5$, or the groups of $R^6$ and $R^7$ with the nitrogen atom to which they bond, which may be intervened or not with nitrogen atom, oxygen atom or sulfur atom" includes pyrrolidinyl, piperidinyl, piperazinyl, morpholino, thiomorpholino, and the like.

The "above mentioned heterocyclic group which is substituted by a lower alkyl group or a lower alkanoyl group" includes the above mentioned heterocyclic groups which are substituted by 1 to 3 groups selected from a straight chain or branched chain alkyl group having 1 to 6 carbon atoms and a straight chain or branched chain alkanoyl group having 1 to 6 carbon atoms, for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 3-methylthiomorpholino, 4-hexylpiperazinyl, 4-acetylpiperazinyl, 4-formyl-3-methylpiperazinyl, 3-propionylpyrrolidinyl, 2-butyrylpyrrolidinyl, 4-pentanoylpiperidinyl, 3-hexanoylmorpholino, 3,4,5-triacetylpiperidinyl, and the like.

The "above mentioned heterocyclic groups substituted by a lower alkyl group, a lower alkanoyl group or a lower alkoxycarbonyl group" includes the above mentioned heterocyclic groups substituted by 1 to 3 groups selected from a straight chain or branched chain alkyl group having 1 to 6 carbon atoms, a straight chain or branched chain alkanoyl group having 1 to 6 carbon atoms and a straight chain or branched chain alkoxycarbonyl group having 1 to 6 carbon atoms in the alkoxy moiety, for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 3-methylthiomorpholino, 4-hexylpiperazinyl, 4-acetylpiperazinyl, 4-formyl-3-methylpiperazinyl, 3-propionylpyrrolidinyl, 2-butyrylpyrrolidinyl, 4-pentanoylpiperidinyl, 3-hexanoylmorpholino, 3,4,5-triacetylpiperidinyl, 4-t-butoxycarbonylpiperazinyl, 3-methoxycarbonylpyrrolidinyl, 2-ethoxycarbonylpyrrolidinyl, 4-propoxycarbonylpiperidinyl, 3-pentyloxycarbonylmorpholino, 3-hexyloxycarbonylpiperidinyl, 3,5-dimethyl-4-t-butoxycarbonylpiperazinyl, 3-acetyl-4-t-butoxycarbonylpiperazinyl, and the like.

The "5- or 6-membered unsaturated heterocyclic residue having 1 to 2 heteroatoms selected from oxygen atom, nitrogen atom and sulfur atom" includes imidazolyl, pyrrolyl, imidazolinyl, pyridyl, primidyl, oxazolyl, pyrazolyl, pyrazolinyl, thiazolyl, thiazolinyl, thienyl, furyl, pyranyl, isothiazolyl, isoxazolyl, pyrazinyl, pyridazinyl, pyrrolinyl, and the like.

The "cycloalkylcarbonyl group" includes a cycloalkylcarbonyl group having 3 to 8 carbon atoms in the cycloalkyl moiety, for example, cyclopropylcarbonyl, cyclobutylcarbonyl, cyclopentylcarbonyl, cyclohexylcarbonyl, cycloheptylcarbonyl, cyclooctylcarbonyl, and the like.

The "phenyl-lower alkanoyl wherein the phenyl moiety may optionally have a lower alkyl substituent" includes phenylalkanoyl groups wherein the phenyl ring may optionally have 1 to 3 substituents of a straight chain or branched chain alkyl group having 1 to 6 carbon atoms and the alkanoyl moiety is a straight chain or branched chain alkanoyl group having 2 to 6 carbon atoms, for example, phenylacetyl, 3-phenylpropionyl, 2-phenylpropionyl, 4-phenylbutyryl, 2,2-dimethyl-3-phenylpropionyl, 5-phenylpentanoyl, 6-phenylhexanoyl, (2-methylphenyl)acetyl, (3-methylphenyl)acetyl, (4-methylphenyl)acetyl, 2-(2-ethylphenyl)propionyl, 3-(3-isopropylphenyl)propionyl, 4-(3-butylphenyl)butyryl, 2,2-dimethyl-3-(4-pentylphenyl)propionyl, 5-(4-hexylphenyl)pentanoyl, 6-(3,4-dimethylphenyl)hexanoyl, (3,4,5-trimethylphenyl)acetyl, and the like.

The "hydroxy-substituted lower alkyl group" includes a straight chain or branched chain alkyl group having 1 to 6 carbon atoms which has 1 to 3 hydroxy substituents, for example, hydroxymethyl, 2-hydroxyethyl, 1-hydroxyethyl, 3-hydroxypropyl, 2,3-dihydroxyethyl, 4-hydroxybutyl, 3,4-dihydroxybutyl, 1,1-dimethyl-2-hydroxyethyl, 5-hydroxypentyl, 6-hydroxyhexyl, 2-methyl-3-hydroxypropyl, 2,3,4-trihydroxybutyl, and the like.

The "lower alkylidene group" includes a straight chain or branched chain alkylidene group having 1 to 6 carbon atoms, for example, methylidene, ethylidene, propylidene, isopropylidene, butylidene, pentylidene, hexylidene, and the like.

The "lower alkoxycarbonyl-substituted lower alkoxy group" includes a straight chain or branched chain alkoxy group having 1 to 6 carbon atoms which is substituted by a straight chain or branched chain alkoxycarbonyl group having 1 to 6 carbon atoms in the alkoxy moiety, for example, methoxycarbonylmethoxy, 3-methoxycarbonylpropoxy, ethoxycarbonylmethoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-t-butoxycarbonylpropoxy, 2-pentyloxycarbonylethoxy, hexyloxycarbonylmethoxy, and the like.

The "carboxy-substituted lower alkoxy group" includes a carboxyalkoxy group wherein the alkoxy moiety is a straight chain or branched chain alkoxy group having 1 to 6 carbon atoms, for example, carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, 2-methyl-3-carboxypropoxy, and the like.

The "lower alkylsulfonyloxy-substituted lower alkoxy group" includes an alkylsulfonyloxyalkoxy group wherein the alkylsulfonyloxy moiety is a straight chain or branched chain alkylsulfonyloxy group having 1 to 6 carbon atoms and the alkoxy moiety is a straight chain or branched chain alkoxy group having 1 to 6 carbon atoms, for example, methylsulfonyloxymethoxy, 3-methylsulfonyloxypropoxy, ethylsulfonyloxymethoxy, 3-ethylsulfonyloxypropoxy, 2-methylsulfonyloxyethoxy, 4-ethylsulfonyloxybutoxy, 5-isopropylsulfonyloxypentyloxy, 6-propylsulfonyloxyhexyloxy, 1,1-dimethyl-2-butylsulfonyloxyethoxy, 2-methyl-3-t-butylsulfonyloxypropoxy, 2-pentylsulfonyloxyethoxy, hexylsulfonyloxymethoxy, and the like.

The "phthalimide-substituted lower alkoxy" group includes a phthalimide-substituted alkoxy group wherein the alkoxy moiety is a straight chain or branched chain alkoxy group having 1 to 6 carbon atoms, for example, phthalimidomethoxy, 2-phthalimidoethoxy, 1-phthalimidoethoxy, 3-phthalimidopropoxy, 4-phthalimidobutoxy, 5-phthalimidopentyloxy, 6-phthalimidohexyloxy, 1,1-dimethyl-2-phthalimidoethoxy, 2-methyl-3-phthalimidopropoxy, and the like.

The "lower alkoxycarbonyl-substituted lower alkyl group" includes an alkoxycarbonylalkyl group wherein the alkoxycarbonyl moiety is a straight chain or branched chain alkoxycarbonyl group having 1 to 6 carbon atoms in the alkoxy moiety and the alkyl moiety is a straight chain or branched chain alkyl group having 1 to 6 carbon atoms, for example, methoxycarbonylmethyl, 3-methoxycarbonylpropyl, ethoxycarbonylmethyl, 3-ethoxycarobnylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-t-butoxycarbonylpropyl, 2-pentyloxycarbonylethyl, hexyloxycarbonylmethyl, and the like.

The "amino which may optionally have 1 to 2 substituents of a lower alkyl group or a cycloalkyl group" includes an amino which may optionally be substituted by a straight chain or branched chain alkyl group having 1 to 6 carbon atoms or a cycloalkyl group having 3 to 8 carbon atoms, for example, amino, methylamino, ethylamino, propylamino, isopropylamino, butylamino, t-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, cyclopropylamino, cyclobutylamino, cyclopentylamino, cyclohexylamino, cycloheptylamino, cyclooctylamino, dicyclopropylamino, dicyclobutylamino, dicyclopentylamino, dicyclohexylamino, dicycloheptylamino, dicyclooctylamino, N-methyl-N-cyclopropylamino, N-ethyl-N-cyclopropylamino, N-methyl-N-cyclopentylamino, N-ethyl-N-cyclohexylamino, and the like.

The "lower alkenyloxy group" includes a straight chain or branched chain alkenyloxy group having 2 to 6 carbon atoms, for example, vinyloxy, allyloxy, 2-butenyloxy, 3-butenyloxy, 1-methylallyloxy, 2-pentenyloxy, 2-hexenyloxy, and the like.

The "cycloalkyl group" includes cycloalkyl groups having 3 to 8 carbon atoms, for example, cyclopropyl, cyclobutyl, cyclopentyl, cyclohexyl, cyclopentyl, cyclooctyl, and the like.

The "amino-substituted lower alkyl group which may optionally have a lower alkyl substituent" includes a straight chain or branched chain alkyl group having 1 to 6 carbon atoms which is substituted by an amino group optionally having 1 to 2 substituents of a straight chain or branched chain alkyl group having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminoethyl, 2-diethylaminoethyl, 2-dimethylaminoethyl, (N-ethyl-N-propylamino)methyl, 2-(N-methyl-N-hexylamino)ethyl, and the like.

The "lower alkoxycarbonyl group" includes a straight chain or branched chain alkoxycarbonyl group having 1 to 6 carbon atoms in the alkoxy moiety, for example, methoxycarbonyl, ethoxycarbonyl, propoxycarbonyl, isopropoxycarbonyl, butoxycarbonyl, t-butoxycarbonyl, pentyloxycarbonyl, hexyoxycarbonyl, and the like.

The "lower alkanoyloxy-substituted lower alkyl group" includes a straight chain or branched chain alkyl group having 1 to 6 carbon atoms which is substituted by a straight chain or branched chain alkanoyloxy group having 2 to 6 carbon atoms, for example, acetyloxymethyl, 2-acetyloxyethyl, 3-propionyloxypropyl, 4-butyryloxybutyl, 5-isobutyryloxypentyl, 1,1-dimethyl-2-pentanoyloxyethyl, 5-hexanoyloxypentyl, 6-acetyloxyhexyl, 2-methyl-3-acetyloxypropyl, and the like.

The "lower alkylsulfonyloxy-substituted lower alkyl group" includes a straight chain or branched chain alkyl group having 1 to 6 carbon atoms which is substituted by a straight chain or branched chain alkylsulfonyloxy group having 1 to 6 carbon atoms, for example, methylsulfonyloxymethyl, 3-methylsulfonyloxypropyl, ethylsulfonyloxymethyl, 3-ethylsulfonyloxypropyl, 2-methylsulfonyloxyethyl, 4-ethylsulfonyloxybutyl, 5-isopropylsulfonyloxypentyl, 6-propylsulfonyloxyhexyl, 1,1-dimethyl-2-butylsulfonyloxyethyl, 2-methyl-3-t-butylsulfonyloxypropyl, 2-pentylsulfonyloxyethyl, hexylsulfonyloxymethyl, and the like.

The "phthalimide-substituted lower alkyl group" includes a straight chain or branched chain alkyl group having 1 to 6 carbon atoms which is substituted by a phthalimide group, for example, phthalimidomethyl, 2-phthalimidoethyl, 1-phthalimidoethyl, 3-phthalimidopropyl, 4-phthalimidobutyl, 5-phthalimidopentyl, 6-phthalimidohexyl, 1,1-dimethyl-2-phthalimidoethyl, 2-methyl-3-phthalimidopropyl, and the like.

The "imidazolyl-substituted lower alkyl group" includes a straight chain or branched chain alkyl group having 1 to 6 carbon atoms which is substituted by an imidazolyl group, for example, (1-imidazolyl)methyl, 2-(1 -imidazolyl)ethyl, 1-(2-imidazolyl)ethyl, 3-(4-imidazolyl)propyl, 4-(5-imidazolyl)butyl, 5-(1 -imidazolyl)pentyl, 6-(2-imidazolyl)hexyl, 1,1-dimethyl-2-(1 -imidazolyl)ethyl, 2-methyl-3-(1-imidazolyl)propyl, and the like.

The "1,2,4-triazolyl-substituted lower alkyl group" includes a straight chain or branched chain alkyl group having 1 to 6 carbon atoms which is substituted by a 1,2,4-triazolyl group, for example, (1,2,4-triazol-1-yl)methyl, 2 -(1,2,4-triazol-1-yl)ethyl, 1-(1,2,4-triazol-1-yl)ethyl, 3-(1,2,4-triazol-3-yl)propyl, 4-(1,2,4-triazol-5-yl)butyl, 5-(1,2,4-triazol-1 -yl)pentyl, 6-(1,2,4-triazol-3-yl)hexyl, 1,1-dimethyl-2-(1,2,4-triazol-5-yl)ethyl, 2-methyl-3-(1,2,4-triazol-1-yl)propyl, and the like.

The "imidazolyl-substituted lower alkoxy group" includes a straight chain or branched chain alkoxyl group having 1 to 6 carbon atoms which is substituted by an imidazolyl group, for example, (1-imidazolyl)methoxy, 2-(1-imidazolyl)ethoxy, 1-(2-imidazolyl)ethoxy, 3-(4-imidazolyl)propoxy, 4-(5 -imidazolyl)butoxy, 5-(1 -imidazolyl)pentyloxy, 6-(2-imidazolyl)hexyloxy, 1,1 -dimethyl-2-(1-imidazolyl)ethoxy, 2-methyl-3-(1-imidazolyl)propoxy, and the like.

The "amino-substituted lower alkanoyloxy group which may optionally have a lower alkyl substituent" includes a straight chain or branched chain alkanoyloxy group having 2 to 6 carbon atoms which is substituted by an amino group optionally being substituted by 1 to 2 straight chain or branched chain alkyl groups having 1 to 6 carbon atoms, for example, 2-aminoacetyloxy, 3-aminopropionyloxy, 2-aminopropionyloxy, 4-aminobutyryloxy, 5-aminopentanoyloxy, 6-aminohexanoyloxy, 2,2-dimethyl-3-aminopropionyloxy, 2 -methyl-3-aminopropionyloxy, 2-methylaminoacetyloxy, 2-ethylaminopropionyloxy, 3-propylaminopropionyloxy, 3-isopropylaminopropionyloxy, 4 -butylaminobutyryloxy, 5-pentylaminopentanoyloxy, 6-hexylaminohexanoyloxy, 2-dimethylaminoacetyloxy, 2-diethylaminoacetyloxy, 2-(N-ethyl-N-propylamino)acetyloxy, 3-(N-methyl-N-hexylamino)propionyloxyl, and the like.

The "an amino group which may optionally have a lower alkanoyl substituent" includes an amino group which may optionally have a substituent of a straight chain or branched chain alkanoyl group having 1 to 6 carbon atoms, for example, amino, acetylamino, propionylamino, isopropionylamino, butyrylamino, pentanoylamino, hexanoylamino, formylamino, and the like.

The "5- or 6-membered saturated heterocyclic group which is formed by combining the groups $R^{19}$ and $R^{20}$ with the nitrogen atom to which they bond, which may be intervened or not with nitrogen atom or oxygen atom" includes, for example, pyrrolidinyl, piperidinyl, piperazinyl, morpholino, and the like.

The "above mentioned heterocyclic groups which are substituted by an amino group optionally being substituted by a lower alkyl group or a lower alkanoyl group" includes, for example, the above mentioned heterocyclic groups which are substituted by 1 to 3 amino groups optionally being substituted by a straight chain or branched chain alkyl group having 1 to 6 carbon atoms, or a straight chain or branched chain alkanoyl group having 1 to carbon atoms, for example, 4-methylpiperazinyl, 3,4-dimethylpiperazinyl, 3 -ethylpyrrolidinyl, 2-propylpyrrolidinyl, 3,4,5-trimethylpiperidinyl, 4-butylpiperidinyl, 3-pentylmorpholino, 3-methyl-4-acetylaminopiperidinyl, 4 -hexylpiperazinyl, 4-acetylaminopiperidinyl, 4-aminopiperidinyl, 2-propionylaminopiperazinyl, 2-isopropionylaminopyrrolidinyl, 3-butyrylaminomorpholino, 4-methyl-3-acetylaminopiperazinyl, 3-pentanoylaminopiperazinyl, 4-hexanoylaminopiperidinyl, and the like.

The benzoheterocyclic compounds of the present invention can be prepared by the following processes.

Reaction Scheme-1

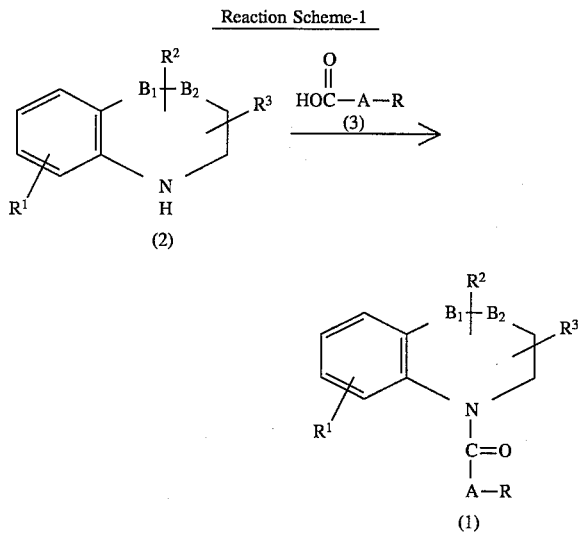

wherein $R, R^1, R^2, R^3, A, B_1$ and $B_2$ are the same as defined above.

The process of Reaction Scheme-1 is carried out by reacting a benzoheterocyclic compound (2) and a carboxylic acid compound (3) by the conventional amino bond producing reaction. The amido bond producing reaction can be carried out under the conditions for the conventional amino bond producing reaction, for example, (a) a mixed acid anhydride process, i.e. a process of reacting the carboxylic acid compound (3) with an alkyl halocarbonate ester to form a mixed acid anhydride and reacting the resultant with the amine compound (2), (b) an activated ester process, i.e. a process of converting the carboxylic acid compound (3) into an activated ester such as p-nitrophenyl ester, N-hydroxysuccinimide ester, 1-hydroxybenzotriazole ester, etc., and reacting the resultant with the amine compound (2), (c) a carbodiimide process, i.e. a process of condensing the carboxylic acid compound (3) and the amine compound (2) in the presence of an activating agent such as dicyclohexylcarbodiimide, carbonyldiimidazole, etc., (d) other processes, i.e. a process of converting the carboxylic acid compound (3) into a carboxylic anhydride by treating it with a dehydrating agent such as acetic anhydride, and reacting the resultant with the amine compound (2); a process of reacting an ester of the carboxylic acid compound (3) with a lower alcohol and the amine compound (2) at a high temperature under high pressure; a process of reacting an acid halide compound of the carboxylic acid compound (3), i.e. a carboxylic acid halide, with the amine compound (2), and the like.

The mixed acid anhydride used in the above mixed acid anhydride process (a) is obtained by the know Schötten-Baumann reaction, and the reaction product is used without isolating from the reaction mixture for the reaction with the amine compound (2) to give the desired compound (1) of the present invention. The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, dimethylaniline, N-methylmorpholine, 1,5-diazabicyclo[4.3.0]nonene-5 (DBN), 1,8-diazabicyclo [5.4.0]undecene-7 (DBU), 1,4-diazabicyclo[2.2.2]-octane (DABCO), and inorganic basic compounds such as potassium carbonate, sodium carbonate, potassium hydrogen carbonate, sodium hydrogen carbonate, etc. The reaction is usually carried out at a temperature from about $-20°$ C. to about $100°$ C., preferably at $0°$ C. to about $50°$ C., for about 5 minutes to about 10 hours, preferably for 5 minutes to about 2 hours.

The reaction between the mixed acid anhydride thus obtained and the amine compound (2) is usually carried out at $-20°$ C. to about $150°$ C., preferably at $10°$ C. to about $50°$ C., for 5 minutes to about 10 hours, preferably for 5 minutes to 5 hours. The mixed acid anhydride process is usually carried out in a solvent. The solvent may be any conventional solvents which are usually used in the mixed acid anhydride process and includes, for example, halogenated hydrocarbons (e.g. chloroform, dichloromethane, dichloroethane, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, acetonitrile, hexamethylphosphoric triamide, etc.), or a mixture of these solvents. The alkyl halocarbonate ester used in the mixed acid anhydride process includes, for example, methyl chloroformate, methyl bromoformate, ethyl chloroformate, ethyl bromoformate, isobutyl chloroformate, and the like. In said process, the carboxylic acid compound (3), the alkyl halocarbonate ester and the amine compound (2) are usually used in each equimolar amount, but preferably, the alkyl halocarbonate ester and the carboxylic acid compound (3) are used each in an amount of about 1 to 1.5 mole to 1 mole of the amine compound (2).

Among the above other processes (d), in case of the process of reacting the carboxylic acid halide with the amine compound (2), the reaction is usually carried out in the presence of a basic compound in an appropriate solvent. The basic compound is any conventional compounds and includes, for example, in addition to the basic compounds used for Schötten-Baumann reaction, sodium hydroxide, potassium hydroxide, sodium hydride, potassium hydride, and the like. The solvent includes, for example, in addition to the solvents used in the mixed acid anhydride process, alcohols (e.g. methanol, ethanol, propanol, butanol, 3-methoxy-1-butanol, ethylcellosolve, methylcellosolve, etc.), pyridine, acetone, water, and the like. The amount of the amine compound (2) and the carboxylic acid halide is not critical, but the carboxylic acid halide is usually used at least in equimolar amount, preferably about 1 to 5 moles to 1 mole of the amine compound (2). The reaction is usually carried out at a temperature from about $-20°$ C. to about $180°$ C., preferably at $0°$ C. to about $150°$ C., for about 5 minutes to about 30 hours.

The amido bond producing reaction in Reaction Scheme-1 may also be carried out by reacting the carboxylic acid compound (3) and the amine compound (2) in the presence of a condensing agent such as phosphorus compounds (e.g. triphenylphosphine, diphenylphosphonyl chloride, phenyl-N-phenylphosphoramide chloridate, diethyl chlorophosphate, diethyl cyanophosphate, diphenylphosphoric azide, bis(2-oxo-3-oxazolidinyl)phosphinic chloride, etc. The reaction is usually carried out in the presence of the solvent and the basic compound as used in the above reaction of the carboxylic acid halide and the amide compound (2) at a temperature from $-20°$ C. to $150°$ C., preferably from $0°$ C. to about $100°$ C., for about 5 minutes to about 30 hours. The condensing agent and the carboxylic acid compound (3) are used at least in equimolar amount, preferably about 1 to 2 moles, to 1 mole of the amine compound (2).

Reaction Scheme-2

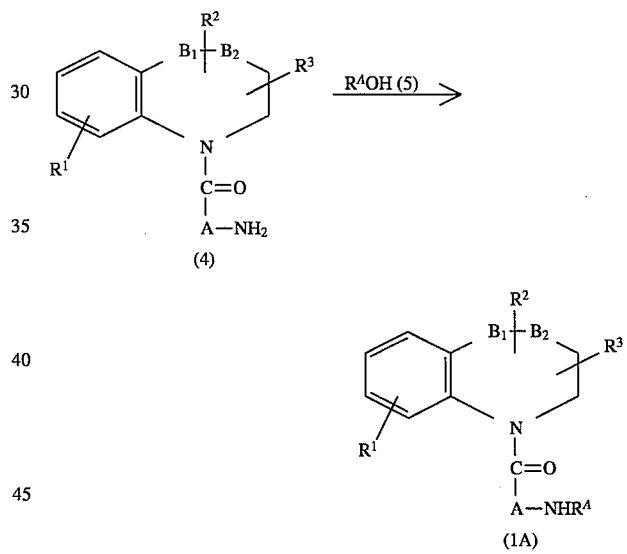

wherein
$R^4$, $R^1$, $R^2$, $R^3$, A, $B_1$ and $B_2$ are the same as defined above.

The reaction of the compound (4) and the compound (5) is carried out in the same conditions as in the reaction of the compound (2) and the compound (3) in Reaction Scheme-1.

Reaction Scheme-3

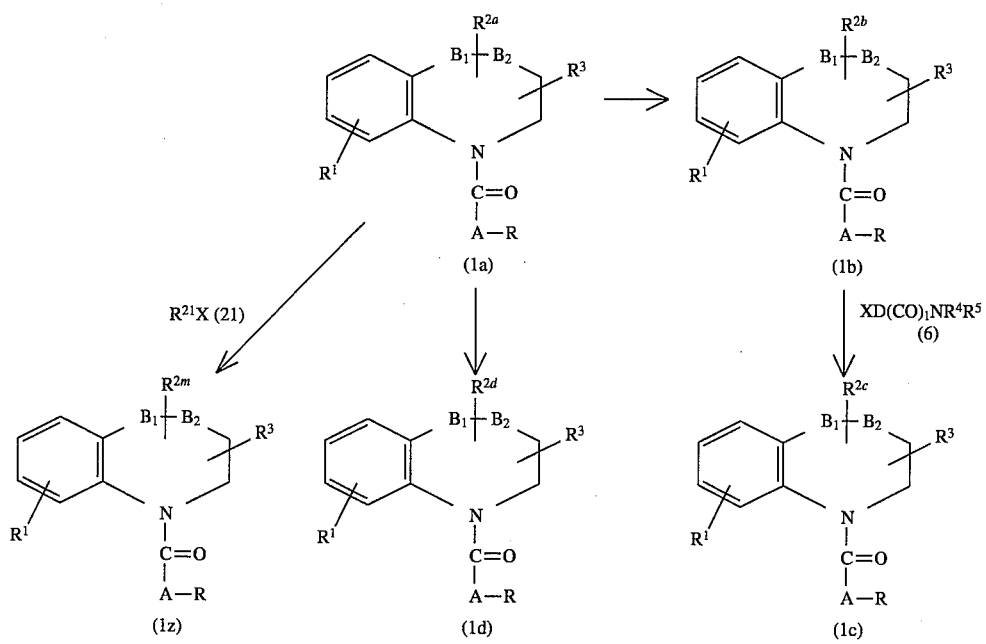

wherein

R, $R^1$, $R^3$, $R^4$, $R^5$, D, I, $B_1$, A and $B_2$ are the same as defined above, $R^{2a}$ is oxo group, $R^{2b}$ is hydroxy group, $R^{2c}$ is a group of the formula: —O—D(CO)$_I$NR$^4$R$^5$ (D, I, $R^4$ and $R^5$ are the same as defined above), $R^{2d}$ is a lower alkylidene group, $R^{2m}$ is a lower alkoxy group or a lower alkenyloxy group, $R^{21}$ is a lower alkyl group or a lower alkenyl group, and X is a halogen atom.

The reaction of converting the compound (1a) into the compound (1b) is carried out by subjecting the compound (1a) to reduction reaction. The reduction reaction is preferably carried out by using a hydrogenation agent. The hydrogenation agent includes, for example, lithium aluminum hydride, sodium borohydride, sodium trimethoxyborohydride, lithium borohydride, diborane, and the like. The hydrogenation agent is used at least in an equimolar amount, preferably 1 mole to 15 moles, to 1 mole of the starting compound. The reduction reaction is usually carried out in an appropriate solvent such as water, lower alcohols (e.g. methanol, ethanol, isopropanol, t-butanol, etc.), ethers (e.g. tetrahydrofuran, diethyl ether, diisopropyl ether, ethylene glycol dimethyl ether, diglyme, etc.), or a mixture thereof, at a temperature from –60° C. to 150° C., preferably at –30° C. to 100° C., for about 10 minutes to about 15 hours. In case that lithium aluminum hydride or diborane is used as a reducing agent, it is preferable to use an anhydrous solvent such as tetrahydrofuran, diethyl ether, diisopropyl ether, diglyme, and the like.

The reaction between the compound (1b) and the compound (6) is usually carried out in an appropriate inert solvent in the presence or absence of a basic compound. The inert solvent includes, for example, aromatic hydrocarbons (e.g. benzene, toluene, xylene, etc.), ethers (e.g. tetrahydrofuran, dioxane, diethylene glycol dimethyl ether, etc.), halogenated hydrocarbons (e.g. dichloromethane, chloroform, carbon tetrachloride, etc.), lower alcohols (e.g. methanol, ethanol, isopropanol, butanol, t-butanol, etc.), acetic acid, ethyl acetate, acetone, acetonitrile, pyridine, dimethyl sulfoxide, dimethylformamide, hexamethylphosphoric triamide, or a mixture thereof. The basic compound includes, for example, metal carbonates and metal hydrogen carbonates (e.g. sodium carbonate, potassium carbonate, sodium hydrogen carbonate, potassium hydrogen carbonate, etc.), metal hydroxides (sodium hydroxide, potassium hydroxide, etc.), sodium hydride, potassium, sodium, sodium amide, metal alcoholates (e.g. sodium methylate, sodium ethylate, etc.), organic basic compounds (e.g. pyridine, N-ethyldiisopropylamine, dimethylaminopyridine, triethylamine, 1,5-diazabicyclo[4.3.0]nonene-5 (DBN), 1,8-diazabicyclo[5.4.0]-undecene-7 (DBU), 1,4-diazabicyclo[2.2.2]octane (DABCO), and the like. The amount of the compound (1b) and the compound (6) is not critical, but the compound (6) is used at least in an equimolar molar, preferably in an amount of 1 mole to 10 moles, to 1 mole of the compound (1b). The reaction is usually carried out at a temperature from 0° C. to about 200° C., preferably 0° C. to about 170° C., for about 30 minutes to about 30 hours. An alkali metal halide such as sodium iodide, potassium iodide, etc. may be added to this reaction system.

The reaction of converting the compound (1a) into the compound (1d) is carried out in an appropriate solvent in the presence of a phosphonium salt and a basic compound. The phosphonium salt includes, for example, a phosphorus compound of the following formula.

wherein $R^9$ is phenyl group, $R^{10}$ is hydrogen atom or a lower alkyl group, and X is the same as defined above. The basic compound includes, for example, inorganic bases such as sodium, potassium, sodium hydride, sodium amide, sodium hydroxide, potassium hydroxide, sodium carbonate, potassium carbonate, sodium hydrogen carbonate, etc., and organic bases such as metal alcoholates (e.g. sodium methylate, sodium ethylate, potassium t-butoxide, etc.), alkyl lithium, aryl lithium or lithium amide (e.g. methyl lithium, n-butyl lithium, phenyl lithium, lithium diisopropylamide, etc.), pyridine, piperidine, quinoline, triethylamine, N,N-dimethylaniline, and the like. The solvent may be any one which does not affect the reaction, and includes, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), aprotic polar solvents (e.g. pyridine, N,N-dimethylaniline, N,N-dimethylformamide, dimethyl sulfoxide, hexamethylphosphoric triamide, etc.), alcohols (e.g. methanol, ethanol, isopropanol, etc.), and the like. The reaction is usually carried out at a temperature from −80° C. to 150° C., preferably at a temperature from −80° to about 120° C., for 0.5 to about 15 hours.

The reaction between the compound (1a) and the compound (21) can be carried out under the same conditions as those of the reaction between the compound (1b) and the compound (6).

The reaction of converting the compound (1e) into the compound (1f) is carried out by reacting with an oxidizing agent in the presence of a co-oxidizing agent in an appropriate solvent. The solvent used in the reaction with an oxidizing agent includes, for example, ethers (e.g. pyridine, dioxane, tetrahydrofuran, diethyl ether, etc.), aromatic hydrocarbons (e.g. benzene, toluene, xylene, etc.), halogenated hydrocarbons (e.g. dichloromethane, dichloroethane, chloroform, carbon tetrachloride, etc.), esters (e.g. ethyl acetate, etc.), water, alcohols (e.g. methanol, ethanol, isopropanol, t-butanol, etc.), or a mixture of these solvents. The co-oxidizing agent includes, N-oxides of organic amines such as pyridine N-oxide, N-ethyldiisopropylamine N-oxide, N-methylmorpholine N-oxide, trimethylamine N-oxide, triethylamine N-oxide, and the like. The oxidizing agent includes, for example, osmium tetraoxide, and the like. The oxidizing agent is used at least in equimolar amount, preferably in an amount of 1 mole to 5 moles, to 1 mole of the starting compound. The reaction is carried out at a temperature from about −20° C. to about 150° C., preferably at a temperature from room temperature to about 100° C., for 1 to about 10 hours.

Reaction Scheme-4

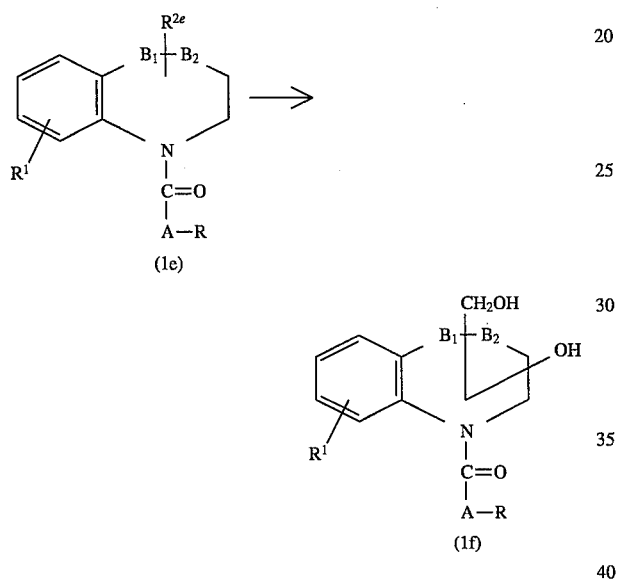

wherein

R, $R^1$, A, $B^1$ and $B^2$ are the same as defined above, and $R^{2e}$ is methylidene group.

Reaction Scheme-5

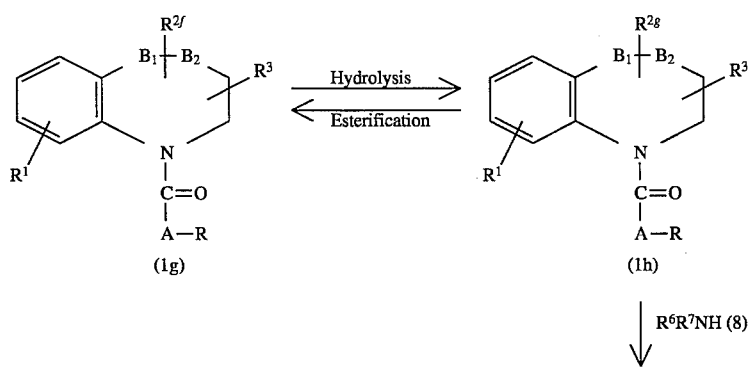

Reaction Scheme-5 -continued

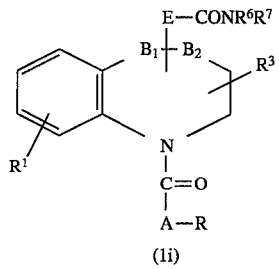

(1i)

wherein

R, $R^1$, $R^3$, $R^6$, $R^7$, E, $B_1$, A and $B_2$ are the same as defined above, $R^{2f}$ is a lower alkoxycarbonyl-substituted lower alkyl group, and $R^{2g}$ is a carboxy-substituted lower alkyl group.

The hydrolysis of the compound (1g) is carried out in the presence of an acid or a basic compound in an appropriate solvent or without a solvent. The solvent includes, for example, water, alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.) and organic acids (e.g. formic acid, acetic acid, aromatic sulfonic acid, etc.). The basic compound includes, for example, metal carbonates (e.g. sodium carbonate, potassium carbonate, etc.), metal hydroxides (e.g. sodium hydroxide, potassium hydroxide, calcium hydroxide, etc.), and the like. The reaction is usually carried out at a temperature from room temperature to about 200° C., preferably at a temperature from room temperature to about 150° C., for 10 minutes to about 25 hours.

The esterification of the compound (1h) is carried out by reacting the starting compound with an alcohol (e.g. methanol, ethanol, isopropanol, etc.) in the presence of a mineral acid (e.g. hydrochloric acid, sulfuric acid, etc.), or a halogenating agent (e.g. thionyl chloride, phosphorus oxychloride, phosphorus pentachloride, phosphorus trichloride) at a temperature from 0° C. to 150° C., preferably at a temperature from 50° C. to 100° C., for about 1 to about 10 hours.

The reaction between the compound (1h) and the compound (8) is carried out under the same conditions as those of the reaction between the compound (2) and the compound (3) in Reaction Scheme-1.

Reaction Scheme-6

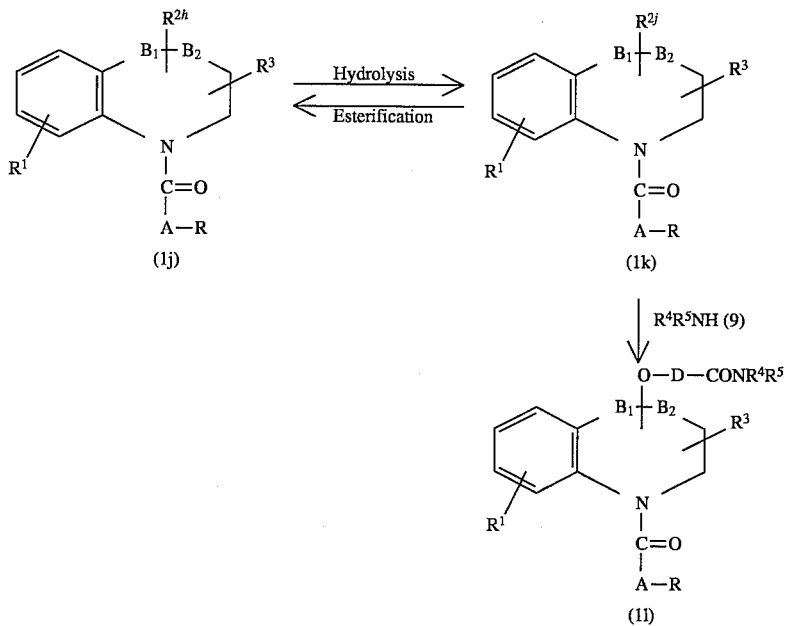

wherein

R, $R^1$, $R^3$, A, $B_1$, $B_2$, $R^4$, $R^5$ and D are the same as defined above, $R^{2h}$ is a lower alkoxycarbonyl-substituted lower alkoxy group, $R^{2i}$ is a carboxy-substituted lower alkoxy group.

The hydrolysis of the compound (1j) is carried out under the same conditions as those of the hydrolysis of the compound (1g) in Reaction Scheme-5.

The esterification of the compound (1k) is carried out under the same conditions as those of the esterification of the compound (1h) in Reaction Scheme-5.

The reaction between the compound (1k) and the compound (9) is carried out under the same conditions as those of the reaction between the compound (2) and the compound (3) in Reaction Scheme-1.

The reaction between the compound (1o) and the compound (11) is carried out under the same conditions as those

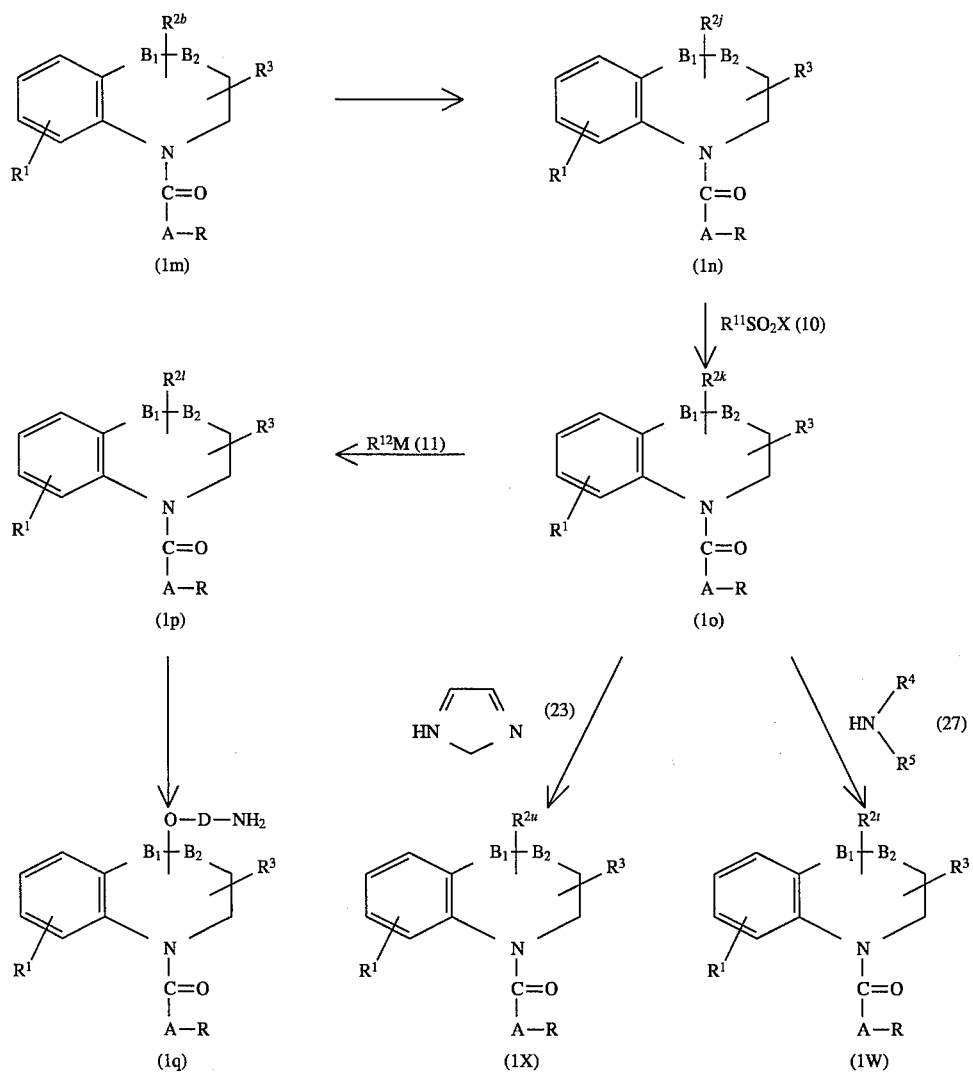

Reaction Scheme-7 wherein

R, $R^1$, $R^3$, $R^{2h}$, $R^4$, $R^5$, A, $B_1$, $B_2$, D and X are the same as defined above, $R^{2j}$ is a hydroxy-substituted lower alkoxy group, $R^{11}$ is a lower alkyl group, $R^{2k}$ is a lower alkylsulfonyloxy-substituted lower alkoxy group, $R^{2l}$ is a phthalimide-substituted lower alkoxy group, M is an alkali metal such as potassium, sodium, etc., $R^{2t}$ is a group of the formula: —O—D—$NR^4R^5$ (wherein D, $R^4$ and $R^5$ are the same as defined above), and $R^{2u}$ is an imidazolyl-substituted lower alkoxy group.

The reaction of converting the compound (1m) into the compound (1n) ia carried out under the same conditions as those of the reaction of converting the compound (1a) into the compound (1b) in Reaction Scheme-3.

The reaction between the compound (1n) and the compound (10) is carried out under the same conditions as those of the reaction between the compound (1b) and the compound (6) in Reaction Scheme-3.

of the reaction between the compound (1b) and the compound (6) in Reaction Scheme-3.

The reaction of converting the compound (1p) into the compound (1q) is carried out by reacting the compound (1p) with hydrazine, or by hydrolysis of the compound (1p), in an appropriate solvent. The solvent used in the reaction with hydrazine includes, for example, the solvents used for the reaction between the compound (2) and the compound (3) in Reaction Scheme-1 as well as water. The reaction is usually carried out at a temperature from 0° C. to about 120° C., preferably from 0° C. to about 100° C., for 0.5 to about 5 hours. Hydrazine is used at least in equimolar amount, preferably in an amount of 1 mole to 5 moles, to 1 mole of the compound (1p).

The above hydrolysis is carried out in the presence of an acid or a basic compound in an appropriate solvent or without a solvent. The solvent includes, for example, water, alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), and organic acids (e.g. formic acid, acetic acid, aromatic sulfonic acid, etc.). The basic compound includes, for example, metal carbonates (e.g. sodium carbonate, potassium carbonate, etc.), metal hydroxides (e.g. sodium hydroxide, potassium hydroxide, calcium hydroxide, etc.), and the like. The reaction is usually carried out at a temperature from room temperature to about 200° C., preferably at a temperature from room temperature to about 150° C., for 10 minutes to about 25 hours.

The reaction between the compound (1o) and the compound (27), and the reaction between the compound (1o) and the compound (23) can be carried out under the same conditions as those of the reaction between the compound (1b) and the compound (6) in Reaction Scheme-3.

example, formic acid, alkali metal salts of fatty acids (e.g. sodium formate, etc.), hydrogenation agents (e.g. sodium borohydride, sodium cyanoborohydride, lithium aluminum hydride, etc.), catalytic reducing agents (e.g. palladium-black, palladium-carbon, platinum oxide, platinum black, Ranney nickel, etc.), and the like.

When formic acid is used as a reducing agent, the reaction is usually carried out at a temperature from room temperature to about 200° C., preferably at about 50° C. to about 150° C., for about one to about 10 hours. Formic acid is used in an excess amount to the compound (1r).

When a hydrogenation agent is used, the reaction is usually carried out at a temperature from about −30° C. to about 100° C., preferably about 0° C. to about 70° C., for about 30 minutes to about 12 hours. The hydrogenation agent is used in an amount of 1 mole to 20 moles, preferably Reaction Scheme-8

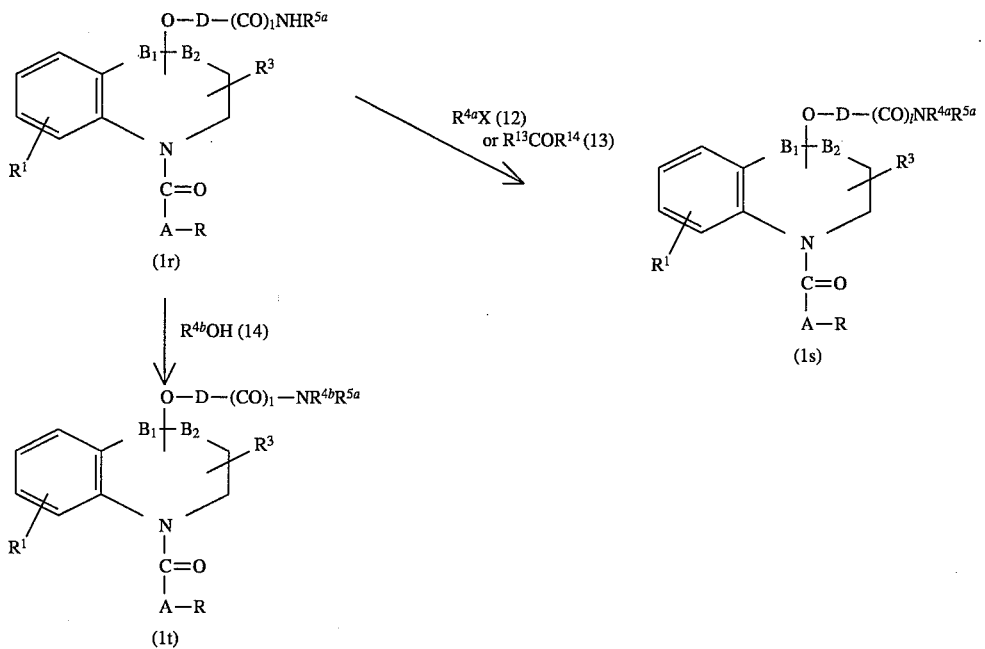

wherein

R, $R^1$, $R^3$, A, $B_1$, $B_2$ and X are the same as defined above, $R^{4a}$ is a lower alkyl group, a cycloalkyl group or an amino-substituted lower alkyl group which may optionally have a lower alkyl substituent, $R^{13}$ and $R^{14}$ are each hydrogen atom or a lower alkyl group, $R^{4b}$ is a lower alkanoyl group, and $R^{5a}$ is hydrogen atom, a lower alkyl group, a lower alkanoyl group, a cycloalkyl group or an amino-substituted lower alkyl group which may optionally have a lower alkyl substituent.

The reaction between the compound (1r) and the compound (12) is carried out under the same conditions as those of the reaction between the compound (1b) and the compound (6) in Reaction Scheme-3.

The reaction between the compound (1r) and the compound (13) is carried out in the presence of a reducing agent in an appropriate solvent or without a solvent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture thereof. The reducing agent includes, for in an amount of 1 mole to 6 moles, to 1 mole of the compound (1r). Especially, when lithium aluminum hydride is used as a reducing agent, the solvent is preferably ethers (e.g. diethyl ether, dioxane, tetrahydrofuran, diglyme, etc.) or aromatic hydrocarbons (e.g. benzene, toluene, xylene, etc.).

Moreover, when a reducing agent is used, the reaction is usually carried out under atmospheric pressure to 20 atms of hydrogen, preferably, under atmospheric pressure to 10 atms of hydrogen, or in the presence of a hydrogen donor such as formic acid, ammonium formate, cyclohexene, hydrazine hydrate, etc., at −30° C. to 100° C., preferably at 0° C. to 60° C., for about one to 12 hours. The reducing agent is usually used in an amount of 0.1 to 40% by weight, preferably 1 to 20% by weight to the amount of the compound (1r). The compound (13) is usually used at least in equimolar amount, preferably in equimolar to excess amount, to the compound (1r).

The reaction between the compound (1r) and the compound (14) is carried out under the same conditions as those of the reaction between the compound (2) and the compound (3) in Reaction Scheme-1.

Reaction Scheme-9

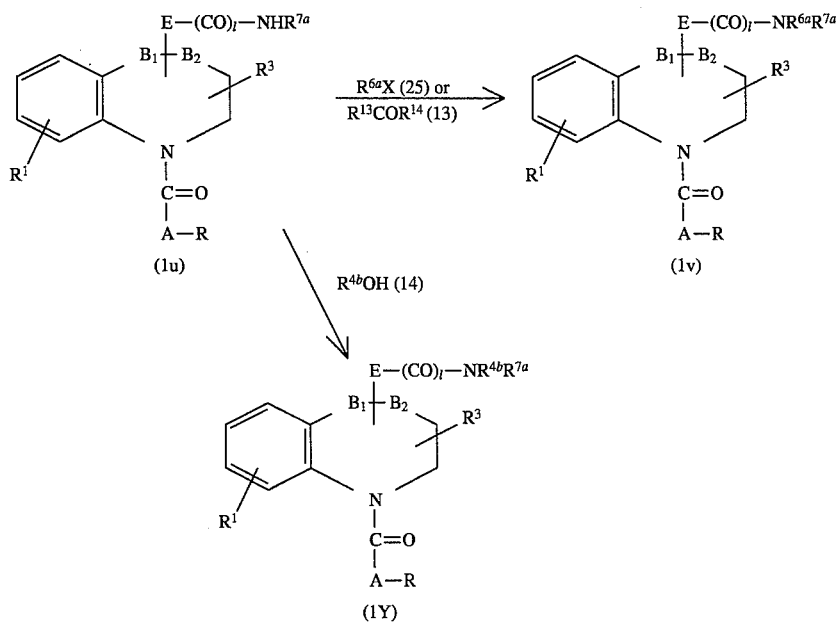

wherein

R, $R^1$, $R^3$, A, $B_1$, $B_2$, $R^{13}$, $R^{14}$, E, $R^{4b}$, l and X are the same as defined above, $R^{6a}$ is a lower alkyl group or an amino-substituted lower alkyl group which may optionally have a lower alkyl substituent, and $R^{7a}$ is hydrogen atom, a lower alkyl group, an amino-substituted lower alkyl group which may optionally have a lower alkyl substituent, or a lower alkanoyl group.

The reaction between the compound (1u) and the compound (25) is carried out under the same conditions as those of the reaction between the compound (1b) and the compound (6) in Reaction Scheme-3.

The reaction between the compound (1u) and the compound (13) is carried out under the same conditions as those of the reaction between the compound (1r) and the compound (13) in Reaction Scheme-8. The reaction between the compound (1u) and the compound (14) is carried out under the same conditions as those of the reaction between the compound (2) and the compound (3) in Reaction Scheme-1.

Reaction Scheme-10

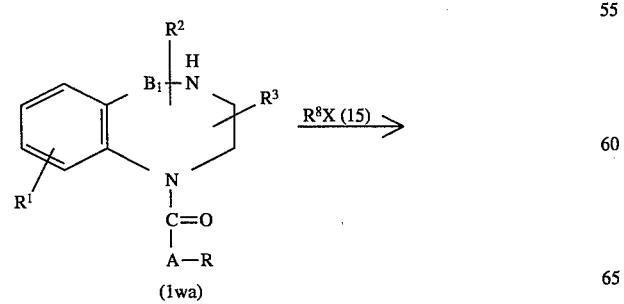

-continued
Reaction Scheme-10

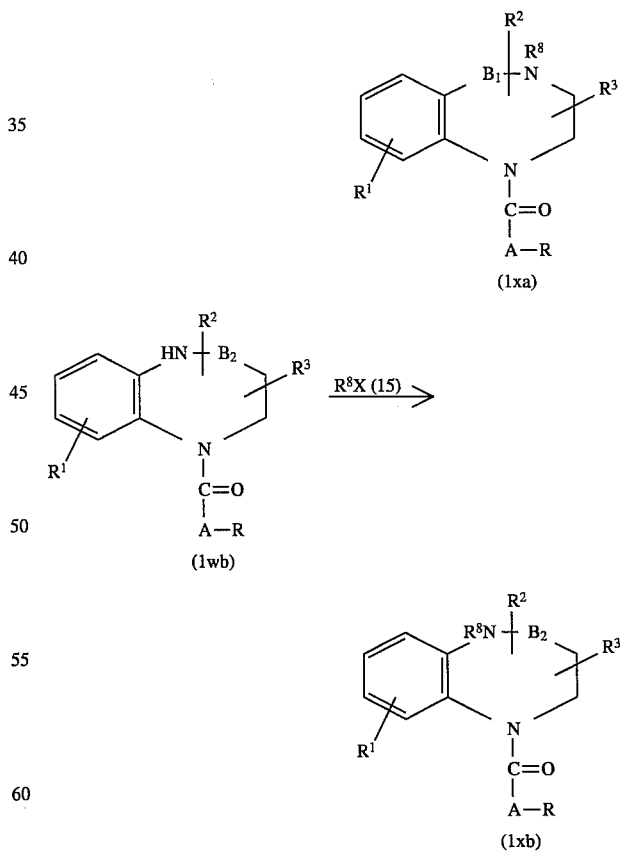

wherein

R, $R^1$, $R^2$, $R^3$, $B_1$, $B_2$, A, $R^8$ and X are the same as defined above.

The reaction between the compound (1wa) or the compound (1wb) and the compound (15) is carried out under the same conditions as those of the reaction between the compound (1b) and the compound (6) in Reaction Scheme-3.

Reaction Scheme-11

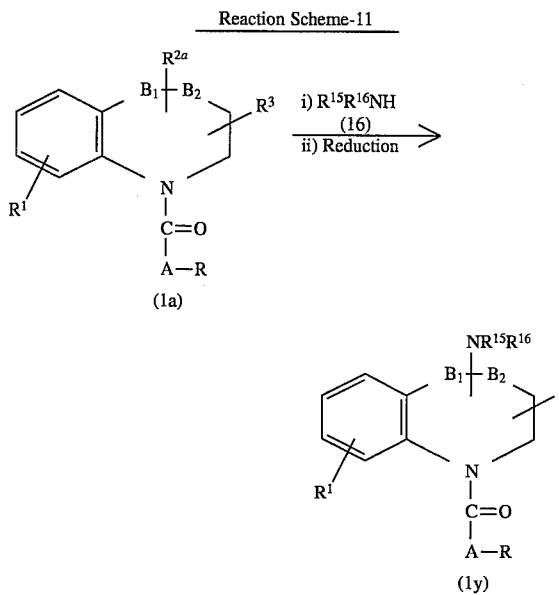

wherein

R, $R^1$, $R^{2a}$, $R^3$, A, $B_1$ and $B_2$ are the same as defined above, and $R^{15}$ and $R^{16}$ are the same or different and are hydrogen atom, a lower alkyl group or a cycloalkyl group.

The reaction of converting the compound (1a) into the compound (1y) is carried out in the presence or absence of a dehydrating agent in an appropriate solvent or without a solvent. The solvent includes, for example, alcohols (e.g. methanol, ethanol, isopropanol, etc.), aromatic hydrocarbons (e.g. benzene, toluene, xylene, etc.), halogenated hydrocarbons (e.g. dichloromethane, dichloroethane, chloroform, carbon tetrachloride, etc.), aprotic polar solvents (e.g. dimethylformamide, dimethylacetamide, N-methylpyrrolidone, etc.), or a mixture of these solvents. The dehydrating agent includes, for example, drying agents which are conventionally used for drying solvents (e.g. molecular sieve, etc.), mineral acids (e.g. hydrochloric acid, sulfuric acid, boron trifluoride, etc.), organic acids (e.g. p-toluenesulfonic acid, etc.), or a mixture thereof. The reaction is usually carried out at a temperature from room temperature to 250° C., preferably at a temperature from about 50° C. to about 200° C., for one to about 48 hours. The amount of the compound (16) is not critical, but it is used at least in equimolar amount, preferably 1 mole to excess amount, to 1 mole of the compound (1a). The dehydrating agent is used in an excess amount when a drying agent is used, and when an acid is used as a dehydrating agent, it is used in a catalytic amount.

The subsequent reduction is carried out by various reduction reactions, for example, by catalytic hydrogenation in the presence of a catalyst in an appropriate solvent. The solvent includes, for example, water, acetic acid, alcohols (e.g. methanol, ethanol, isopropanol, etc.), hydrocarbons (e.g. hexane, cyclohexane, etc.), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. dimethylformamide, etc.), or a mixture of these solvents. The catalyst is, for example, palladium, palladium-black, palladium-carbon, platinum, platinum oxide, copper chromite, Ranney nickel, and the like. The catalyst is usually used in an amount of 0.02 to 1 mole to 1 mole of the starting compound. The reaction is usually carried out at a temperature from −20° C. to about 100° C., preferably at a temperature from 0° C. to about 70° C., under a pressure of 1 atm to 10 atms of hydrogen, for 0.5 to 20 hours.

The above mentioned conditions for reduction can be employed in the present reduction, but the reduction using a hydrogenation agent is more preferable. The hydrogenation agent includes, for example, lithium aluminum hydride, sodium borohydride, diboran, etc., and is used at least in equimolar amount, preferably in an amount of 1 mole to 10 moles, to 1 mole of the compound (1a). The reduction is carried out in an appropriate solvent such as water, lower alcohols (e.g. methanol, ethanol, isopropanol, etc.), ethers (e.g. tetrahydrofuran, diethyl ether, diglyme, etc.), dimethylformamide, or a mixture of these solvents, at a temperature of about −60° C. to about 50° C., preferably at a temperature from −30° C. to room temperature, for about 10 minutes to about 15 hours. When lithium aluminum hydride or diboran is used as a reducing agent, anhydrous solvent such as diethyl ether, tetrahydrofuran, diglyme, etc., is preferably used.

When at least one of $R^{15}$ and $R^{16}$ in the compound (1y) is hydrogen atom, the compound is converted into the compound (1y) wherein at least one of $R^{15}$ and $R^{16}$ is a lower alkyl group by reacting it with the compound (12) or the compound (13) under the same conditions as those of the reaction between the compound (1r) and the compound (12) or the compound (13) in Reaction Scheme-8.

The starting compound (3) or (4) can be prepared by the following processes.

Reaction Scheme-12

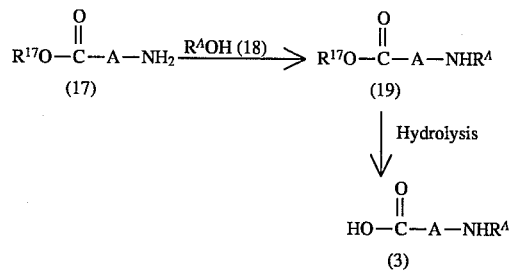

wherein $R^{17}$ is a lower alkyl group, and $R^A$ and A are the same as defined above.

The reaction between the compound (17) and the compound (18) is carried out under the same conditions as those of the reaction between the compound (2) and the compound (3) in Reaction Scheme-1.

The hydrolysis of the compound (19) is carried out under the same conditions as those of the hydrolysis of the compound (1g) in Reaction Scheme-5.

Reaction Scheme-13

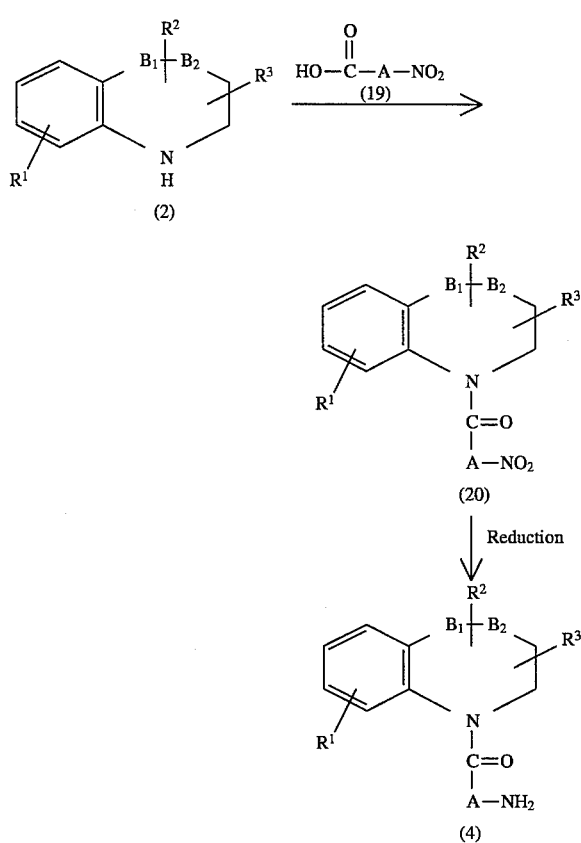

ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvents (e.g. N,N-dimethylformamide, etc.), or a mixture of these solvents. The reducing catalyst includes, for example, palladium, palladium-black, palladium-carbon, platinum, platinum oxide, copper chromite, Ranney nickel, and the like. The catalyst is usually used in an amount of 0.02 to 1 mole to 1 mole of the starting compound. The reaction is usually carried out at a temperature from about −20° C. to about 150° C., preferably at a temperature from 0° C. to 100° C., under a pressure of 1 atm to 10 atms of hydrogen, for 0.5 to about 10 hours. An acid (e.g. hydrochloric acid) may be added to the reaction system.

When the method (ii) is employed, there is used as a reducing agent a mixture of iron, zinc, tin or stannous chloride and a mineral acid (e.g. hydrochloric acid, sulfuric acid, etc.), or a mixture of iron, iron sulfide, zinc or tin and an alkali metal hydroxide (e.g. sodium hydroxide, etc.), sulfide (e.g. ammonium sulfide, etc.), aqueous ammonia, ammonium salt (e.g. ammonium chloride, etc.). The inert solvent includes, for example, water, methanol, ethanol, dioxane, acetic acid, and the like. The conditions for reduction can be selected according to the kinds of the reducing agent to be used. For example, when a mixture of iron and hydrochloric acid is used as a reducing agent, the reaction is preferably carried out at a temperature from 0° C. to about 100° C., for 0.5 to about 10 hours. The reducing agent may be used at least in equimolar amount, usually in an amount of 1 mole to 20 moles to 1 mole of the starting compound.

Reaction Scheme-14

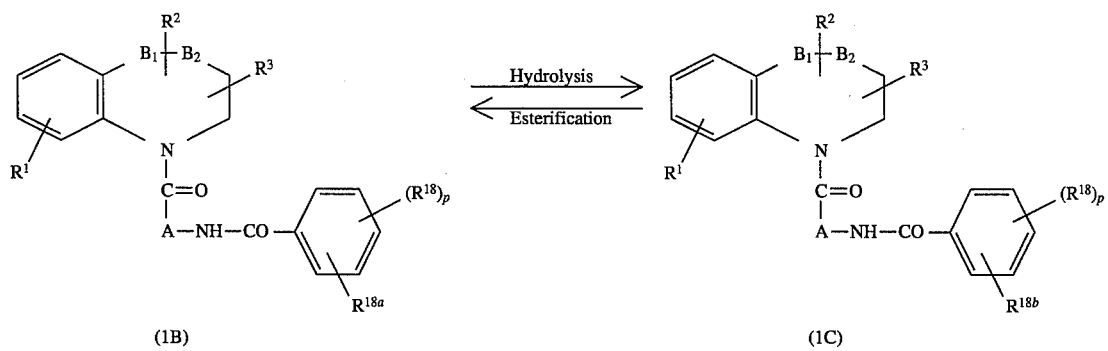

wherein $R^1$, $R^2$, $R^3$, A, $B_1$ and $B_2$ are the same as defined above.

The reaction between the compound (2) and the compound (19) is carried out under the same conditions as those of the reaction between the compound (2) and the compound (3) in Reaction Scheme-1.

The reduction of the compound (20) is carried out, for example, (i) by using a reducing catalyst in an appropriate solvent, or (ii) by using a mixture of a metal or a metal salt and an acid, or a mixture of a metal or a metal salt and an alkali metal hydroxide, sulfide, ammonium salt, etc., as a reducing agent in an inert solvent.

When the method (i) is employed, the solvent includes, for example, water, acetic acid, alcohols (e.g. methanol, wherein $R^1$, $R^2$, $R^3$, $R^{18}$, $B_1$ and $B_2$ are the same as defined above, p is 0, 1 or 2, $R^{18a}$ is a lower alkoxycarbonyl group, and $R^{18b}$ is carboxy group.

The hydrolysis of the compound (1B) is carried out under the same conditions as those of the hydrolysis of the compound (1g) in Reaction Scheme-5. The esterification of the compound (1C) is carried out under the same conditions as those of the esterification of the compound (1h) in Reaction Scheme-5.

Reaction Scheme-15

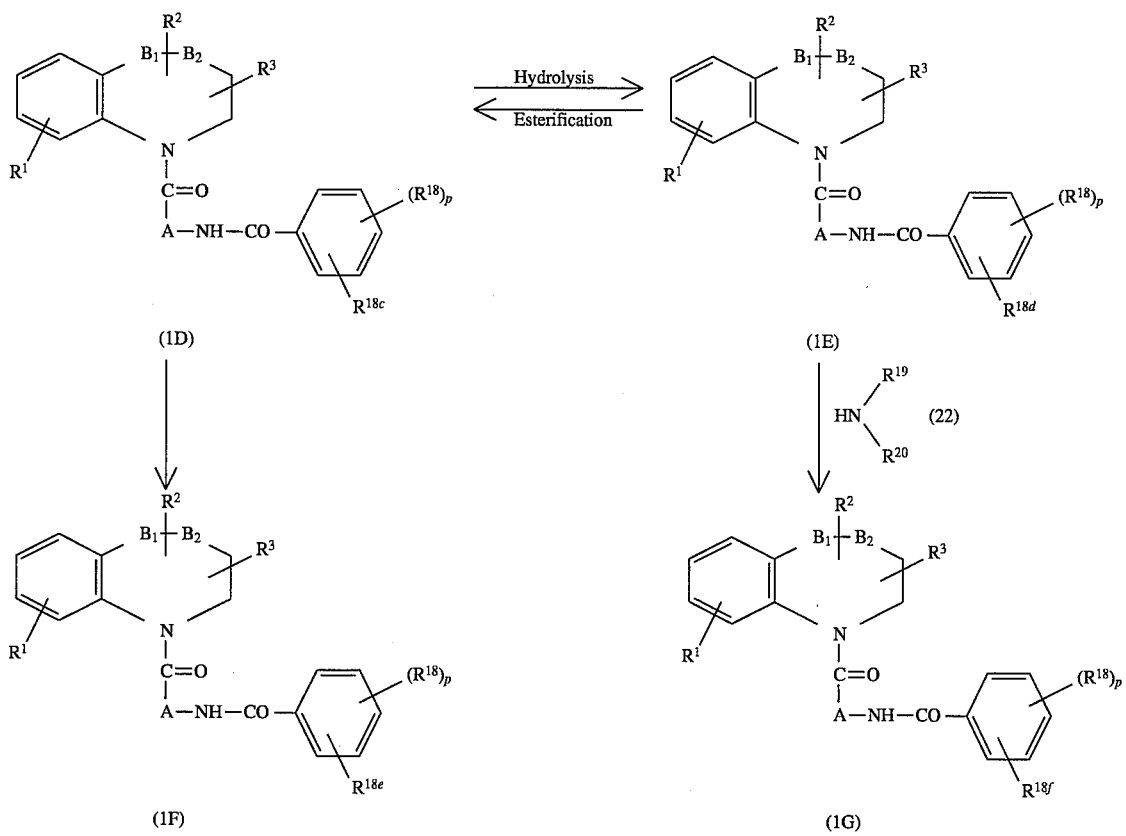

wherein

R$^1$, R$^2$, R$^3$, R$^{18}$, R$^{19}$, R$^{20}$, p, B$_1$ and B$_2$ are the same as defined above, R$^{18c}$ is a lower alkoxycarbonyl-substituted lower alkoxy group, R$^{18d}$ is a carboxy-substituted lower alkoxy group, R$^{18e}$ is a hydroxy-substituted lower alkoxy group, and R$^{18f}$ is a group of the formula: —O—E—CO—NR$^{19}$R$^{20}$ (E, R$^{19}$ and R$^{20}$ are the same as defined above).

The hydrolysis of the compound (1D) is carried out under the same conditions as those of the hydrolysis of the compound (1g) in Reaction Scheme-5. The esterification of the compound (1E) is carried out under the same conditions as those of the esterification of the compound (1h) in Reaction Scheme-5.

The reaction of the compound (1E) with the compound (22) is carried out under the same conditions as those of the reaction between the compound (2) and the compound (3) in Reaction Scheme-1.

The reaction of converting the compound (1D) into the compound (1F) is carried out under the same conditions as those of the reaction of converting the compound (1a) into the compound (1b) in Reaction Scheme-3.

Reaction Scheme-16

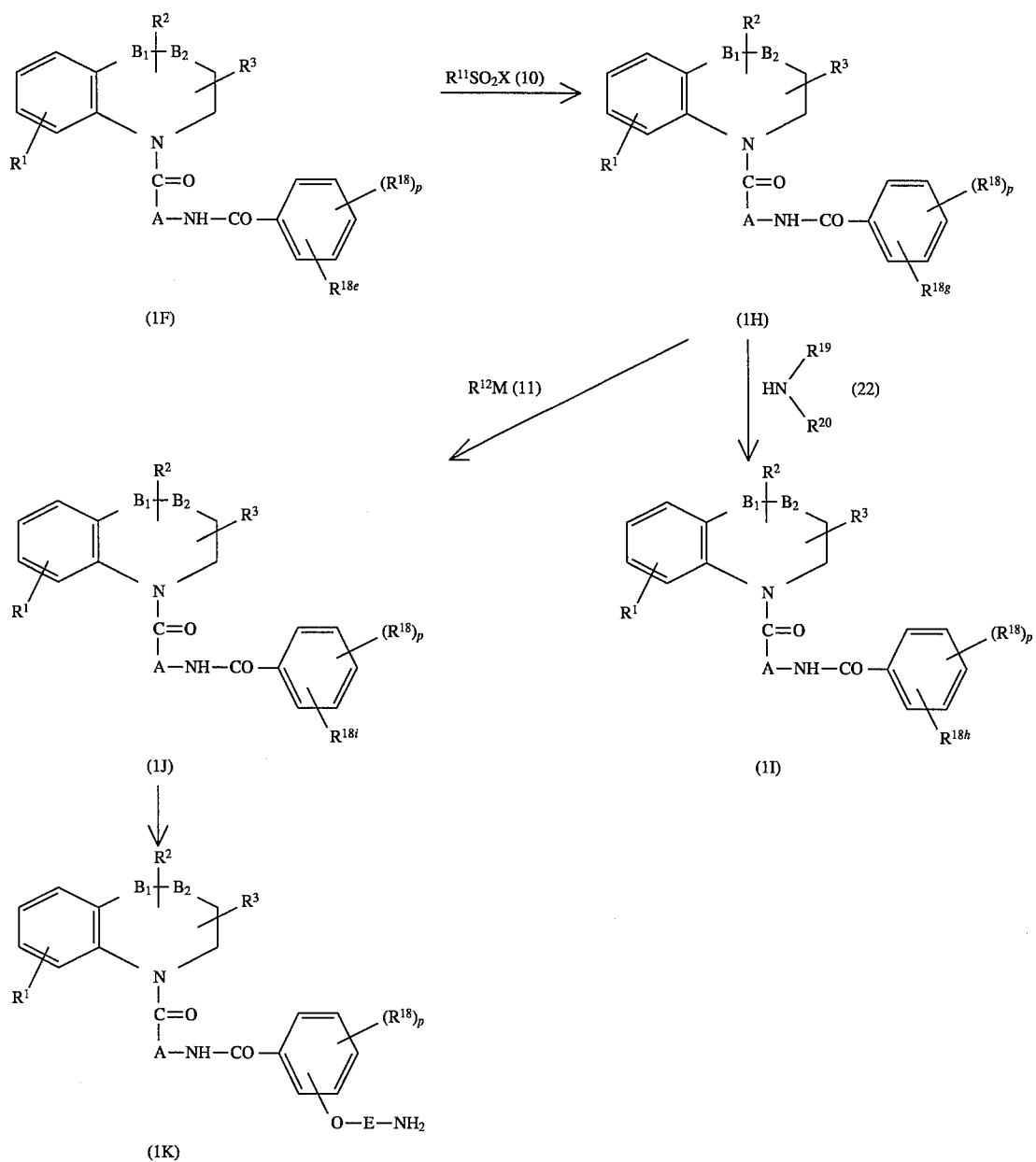

wherein
R$^1$, R$^2$, R$^{18}$, p, R$^{18e}$, R$^{11}$, X, E, R$^{12}$, R$^{19}$, R$^{20}$ and M are the same as defined above.

The reaction of the compound (1F) with the compound (10) is carried out under the same conditions as those of the reaction between the compound (1n) and the compound (10) in Reaction Scheme-7.

The reaction of the compound (1H) with the compound (22) is carried out under the same conditions as those of the reaction between the compound (1n) and the compound (10) in Reaction Scheme-7.

The reaction of the compound (1H) with the compound (11) is carried out under the same conditions as those of the reaction of the compound (1o) with the compound (11) in Reaction Scheme-7.

The reaction of converting the compound (1J) into the compound (1K) is carried out under the same conditions as those of the reaction of converting the compound (1p) into the compound (1q) in Reaction Scheme-7.

In this reaction, there may optionally be obtained a compound of the formula:

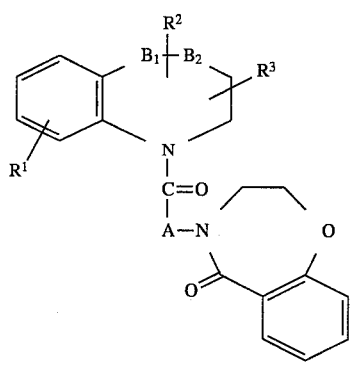

but which can easily be removed from the desired compounds.

Reaction Scheme-17

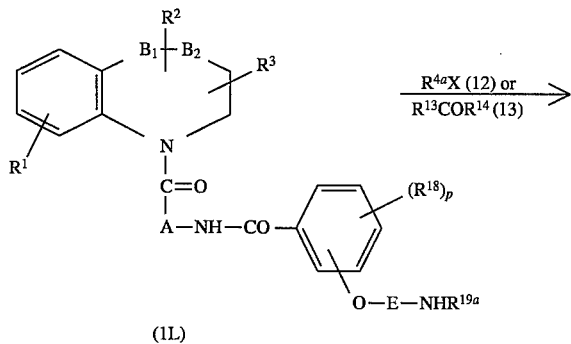

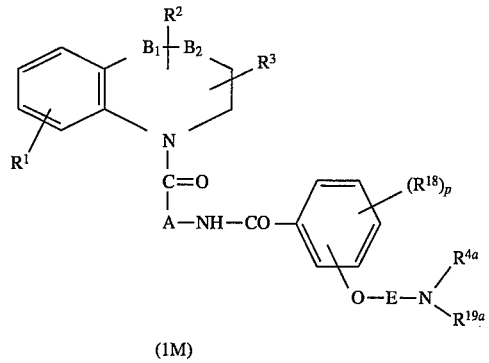

wherein

R$^1$, R$^2$, R$^3$, R$^{18}$, X, p, E, R$^{4a}$, R$^{13}$ and R$^{14}$ are the same as defined above, and R$^{19a}$ is hydrogen atom or a lower alkyl group.

The reaction of the compound (1L) with the compound (12) is carried out under the same conditions as those of the reaction between the compound (1r) and the compound (12) in Reaction Scheme-8. The reaction of the compound (1L) with the compound (13) is carried out under the same conditions as those of the reaction between the compound (1r) and the compound (13) in Reaction Scheme-8.

Reaction Scheme-18

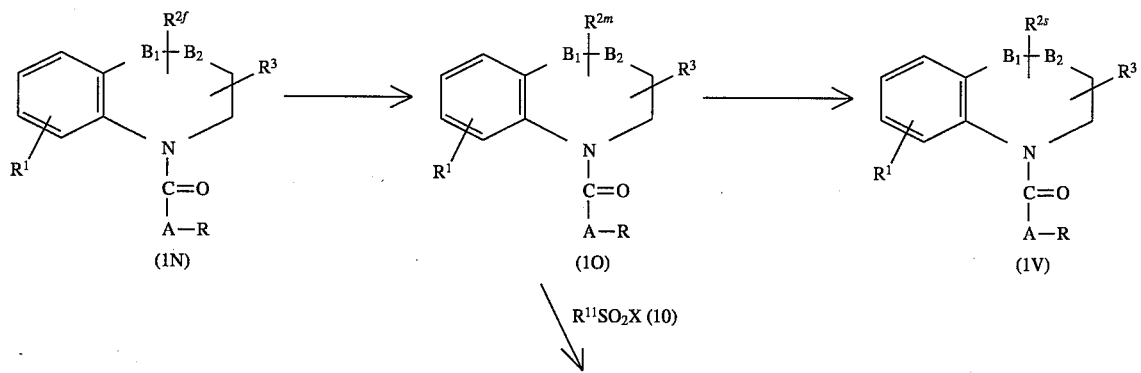

-continued
Reaction Scheme-18

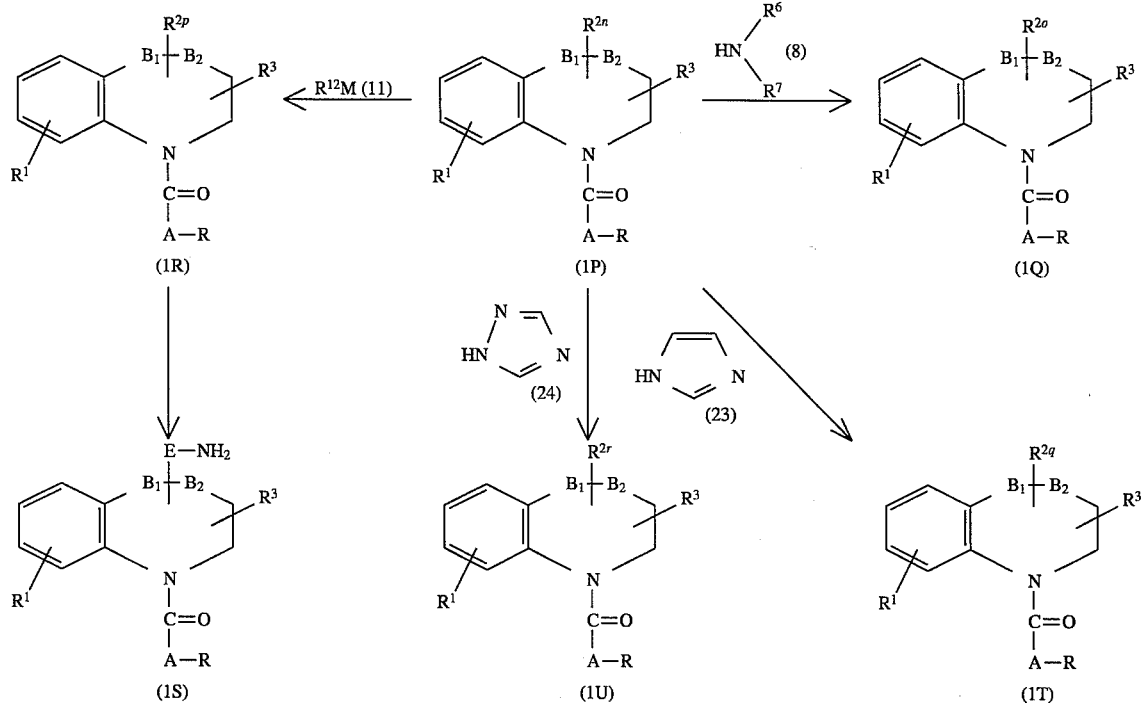

wherein

R, $R^1$, $R^{2f}$, $B_1$, $B_2$, $R^3$, $R^{11}$, X, $R^{12}$, M, $R^6$ and $R^7$ are the same as defined above, $R^{2m}$ is a hydroxy-substituted lower alkyl group, $R^{2n}$ is a lower alkylsuflonyloxy-substituted lower alkyl group, $R^{2o}$ is a group of the formula: —E—$NR^6R^7$ (E, $R^6$ and $R^7$ are the same as defined above), $R^2P$ is a phthalimide-substituted lower alkyl group, $R^{2q}$ is an imidazolyl-substituted lower alkyl group, $R^{2r}$ is a 1,2,4-triazolyl-substituted lower alkyl group, and $R^{2s}$ is a lower alkanoyloxy-substituted lower alkyl group.

The reaction of converting the compound (1N) into the compound (1O) is carried out under the same conditions as those of the reaction of converting the compound (1m) into the compound (1n) in Reaction Scheme-7. The reaction between the compound (1P) and the compound (8), the reaction of the compound (1P) with the compound (23) and the reaction of the compound (1P) with the compound (24) are carried out under the same conditions as those of the reaction of the compound (1n) with the compound (10) in Reaction Scheme-7.

The reaction of the compound (1P) with the compound (11) is carried out under the same conditions as those of the reaction of the compound (1o) with the compound (11) in Reaction Scheme-7.

The reaction of converting the compound (1R) into the compound (1S) is carried out under the same conditions as those of the reaction of converting the compound (1p) into the compound (1s) in Reaction Scheme-7.

The reaction of converting the compound (1O) into the compound (1V) is carried out by lower-alkanoylating the compound (1O) by using a compound of the formulae: $(R^{22})_2O$ (26) or $R^{22}X$ (27) [wherein $R^{22}$ is a lower alkanoyl group, and X are the same as defined above]. This lower-alkanoylating reaction is carried out in the presence or absence of a basic compound. The basic compound includes, for example, alkali metals (e.g. sodium, potassium, etc.), hydroxides, carbonates, hydrogen carbonates of these alkali metals, or organic bases such as N,N-dimethylaminopyridine, pyridine, piperidine, and the like. The reaction can proceed either without a solvent, or in a solvent. The solvent includes, for example, ketones (e.g. acetone, methyl ethyl ketone, etc.), ethers (e.g. diethyl ether, dioxane, etc.), aromatic hydrocarbons (e.g. benzene, toluene, xylene, etc.), water, pyridine, and the like. The compounds (7) and (8) are used at least in equimolar amount to the starting compound, but they are preferably used in an amount of 1 mole to excess amount to 1 mole of the starting compound. The above reaction is carried out at a temperature from 0° to 200° C., preferably at about 0° C. to about 150° C., for 5 minutes to about 5 days.

Among the desired compounds (1) of the present invention, the compound (1) wherein the groups of $R^6$ and $R^7$ form a piperazine ring being substituted by a lower alkoxycarbonyl group at 4-position, can be hydrolyzed under the same conditions as those of the hydrolysis of the compound (1g) in Reaction Scheme-5, and converted into the compound (1) wherein the substituent at 4-position of said piperazine ring is hydrogen atom.

Among the compounds (1), the compound (1) wherein both $R^2$ and $R^3$ are a lower alkoxy group, and they bond at the same position, can be hydrolyzed under the same conditions as those of the hydrolysis of the compound (1g) in Reaction Scheme-5, and converted into the compound (1) wherein $R^2$ is oxo group.

Among the desired compounds (1) of the present invention, the compounds having an acidic group can easily be converted into salts by treating with a pharmaceutically acceptable basic compound. The basic compound includes, for example, metal hydroxides (e.g. sodium hydroxide, potassium hydroxide, lithium hydroxide, calcium hydroxide, etc.), alkali metal carbonates or hydrogen carbonates (e.g. sodium carbonate, sodium hydrogen carbonate, etc.) and alkali metal alcoholates (e.g. sodium methylate, potassium ethylate, etc.). Besides, among the desired compounds (1) of the present invention, the compounds having a basic group can easily be converted into acid addition salts thereof by treating with a pharmaceutically acceptable acid. The acid includes, for example, inorganic acids (e.g. sulfuric acid, nitric acid, hydrochloric acid, hydrobromic acid, etc.), and organic acids (e.g. acetic acid, p-tolunesulfonic acid, ethanesulfonic acid, oxalic acid, maleic acid, fumaric acid, citric acid, succinic acid, benzoic acid, etc.). These salts show as well excellent vasopressin antagonistic activity as the desired compounds (1).

In addition, the compounds (1) of the present invention include stereoisomers and optical isomers, and these isomers are also useful as vasopressin antagonist.

The compounds of the present invention thus obtained can easily be isolated and purified by conventional isolation methods. The isolation methods are, for example, distillation method, recrystallization method, column chromatography, ion exchange chromatography, gel chromatography, affinity chromatography, preparative thin layer chromatography, extraction with a solvent, and the like.

The desired compounds (1) of the present invention and salts thereof are useful as a vasopressin antagonist, and are used in the form of a conventional pharmaceutical preparation. The preparation is prepared by using conventional diluents or carriers such as fillers, thickening agents, binders, wetting agent, disintegrators, surfactants, lubricants, and the like. The pharmaceutical preparations can be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starch, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of the present invention and the above carriers into hard gelatin capsules or soft capsules in usual manner. In the preparation of injections, the solutions, emulsions and suspensions are sterilized and are preferably made isotonic with the blood. In the preparation of these solutions, emulsions and suspensions, there are used conventional diluents, such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agent, preservatives, perfumes, flavors, sweeting agents, and other medicaments, if required.

The amount of the desired compound of the present invention to be incorporated into the vasopressin antagonist is not specified but may be selected from a broad range, but usually, it is preferably in the range of 1 to 70 by weight, more preferably 5 to 50% by weight.

The vasopressin antagonist containing as an active ingredient the compounds (1) of the present invention and a salt thereof may be administered in any method, and suitable method for administration may be determined in accordance with various forms of preparations, ages, sexes and other conditions of the patients, the degree of severity of diseases, and the like. For example, tablets, pills, solutions, suspensions, emulsions, granules and capsules are administered orally. The injections are intravenously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the vasopressin antagonist of the present invention may be selected in accordance with the usage, ages, sexes and other conditions of the patients, the degree of severity of the diseases, and the like, but it is usually in the range of about 0.6 to 50 mg of the active compound of the present invention per 1 kg of body weight of the patient per day. The active compound is preferably contained in an amount of about 10 to about 1000 mg per the dosage unit.

BEST MODE FOR CARRYING OUT THE INVENTION

Examples

The present invention is illustrated in more detail by the following Preparations of vasopressin antagonist, Reference Examples of processes for preparing the starting compounds to be used for preparing the desired compounds of the present invention, and Examples of processes for preparing the desired compounds, and Experiments of the activities of the desired compounds of the present invention.

PREPARATION 1

Film coated tablets are prepared from the following compounds.

| Components | Amount |
| --- | --- |
| 5-Hydroxy-7-chloro-1-[6-(2-methylbenzoyl-amino)nicotinoyl]-2,3,4,5-tetrahydro-1H-benzazepine | 150 g |
| Avicel (trade name of microcrystalline cellulose manufactured by Asahi Chemical Industry, Co., Ltd. Japan) | 40 g |
| Corn starch | 30 g |
| Magnesium stearate | 2 g |

-continued

| Components | Amount |
|---|---|
| Hydroxypropyl methylcellulose | 10 g |
| Polyethylene glycol-6000 | 3 g |
| Castor oil | 40 g |
| Ethanol | 40 g |

The active compound of the present invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

PREPARATION 2

Tablets are prepared from the following components.

| Components | Amount |
|---|---|
| 5-Hydroxy-7-chloro-1-[2-(5-methylbenzoylamino)-thenoyl]-2,3,4,5-tetrahydro-1H-benzazepine | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of the present invention, citric acid, lactose, dicalcium phosphate, Pullonic F-68 and sodium laurylsulfate are mixed. The mixture is screened with No. 60 screen and is granulated with an alcohol solution containing polyvinylpyrrolidone, Carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

PREPARATION 3

An injection preparation is prepared from the following components.

| Components | Amount |
|---|---|
| 5-Hydroxy-7-chloro-1-[2-(2-methylbenzoylamino)-5-thiazolylcarbonyl]-2,3,4,5-tetrahydro-1H-benzazepine | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved with stirring in distilled water of half volume of the above with stirring at 80° C. The solution thus obtained is cooled to 40° C., and the active compound of the present invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

REFERENCE EXAMPLE 1

To 6-nitronicotinic acid (3.5 g) is added thionyl chloride (50 ml), and the mixture is refluxed for three hours, and evaporated to remove thionyl chloride to give 6-nitronicotinoyl chloride, which is added with stirring to a solution of 7-chloro-5-oxo-2,3,4,5-tetrahydro-1H-benzazepine (3.4 g) in pyridine (50 ml) under ice-cooling. The mixture is stirred at room temperature overnight. To the reaction mixture is added water, and the mixture is extracted with ethyl acetate. The extract is washed successively with 0.1N aqueous hydrochloric acid and water, and dried over magnesium sulfate. The resultant is evaporated under reduced pressure to remove the solvent, and the residue is purified by silica gel column chromatography to give 7-chloro-5-oxo-1-(6-nitronicotinoyl)-2,3,4,5-tetrahydro-1H-benzazepine (4.9 g) as colorless amorphous.

$^1$H-NMR (CDCl$_3$)δ:1.85–2.60 (2H, m), 2.75–2.95 (2H, m), 3.10–4.00 (1H, m), 4.20–5.20 (1H, m), 6.55–6.75 (1H, m), 7.15–7.30 (1H, m), 7.75–7.90 (2H, m), 8.12 (1 H, d, J=8.3 Hz), 8.46 (1 H, s).

REFERENCE EXAMPLE 2

2N Hydrochloric acid (50 ml) is added to reduced iron (23.5 g), and the mixture is allowed to stand for 10 minutes. The mixture is filtered, and washed with water and acetone, and then, dried. To 7-chloro-5-oxo-1-(6-nitronicotinoyl)-2,3,4,5-1H-tetrahydro-benzazepine (9.4 g) is added acetic acid (100 ml), and thereto is added gradually the above reduced iron at 80° C. The mixture is stirred at the same temperature for 30 minutes, and filtered on Celite. The filtrate is neutralized with sodium hydrogen carbonate, and extracted with dichloromethane. The extract is washed with water, and dried over magnesium sulfate. The resultant is evaporated under reduced pressure to remove the solvent, and the residue is purified by silica gel column chromatography, and further recrystallized from dichloromethane-diethyl ether to give 7-chloro-5-oxo-1-(6-aminonicotinoyl)-2,3,4,5-tetrahydro-1H-benzazepine (6.5 g) as white powder.

M.p. 210°–213° C.

REFERENCE EXAMPLE 3

Using the suitable starting compounds, the following compounds are obtained in the same manner as in Reference Example 1.

7-Chloro-5-methoxycarbonylmethyl-1-(6-nitronicotinoyl)-2,3,4,5-tetrahydro-1H-benzazepine
White powder
M.p. 162°–165° C. (recrystallized from dichloromethane-diethyl ether).

7-Chloro-5-methoxycarbonylmethoxy-1-(6-nitronicotinoyl)-2,3,4,5-tetrahydro-1H-benzazepine
White powder
M.p. 154°–157° C. (recrystallized from dichloromethane-diethyl ether).

7-Chloro-1-(6-nitronicotinoyl)-2,3,4,5-tetrahydro-1H-benzazepine
White powder
M.p. 171°–174° C. (recrystallized from dichloromethane-diethyl ether).

7-Chloro-4-methyl-1-(6-nitronicotinoyl)-2,3,4,5-tetrahydro-1H-1,4-benzodiazepine
Colorless amorphous
$^1$H-NMR (CDCl$_3$)δ:2.44 (3H, s), 3.00–3.30 (3H, m), 3.73 (1H, d, J=14.1 Hz), 4.02 (1H, d, J=14.1 Hz), 4.80–4.95 (1H, m), 6.56 (1 H, d, J= 8.3 Hz), 7.00 (1 H, dd, J=2.4, 8.3 Hz), 7.15–7.60 (1 H, m), 7.92 (1 H, dd, J=2.1, 8.3 Hz), 8.14 (1H, d, J=8.2 Hz), 8.36 (1H, d, J=1.7 Hz).

7-Chloro-5-oxo-1-(5-nitrothenoyl)-2,3,4,5-tetrahydro-1H-benzazepine
White powder
M.p. 166°–169° C. (recrystallized from dichloromethane-diethyl ether).

7-Chloro-5-oxo-1-(5-nitro-2-furoyl)-2,3,4,5-tetrahydro-1H-benzazepine
White powder
M.p. 124°–126° C. (recrystallized from dichloromethane-diethyl ether).

7-Chloro-5-oxo-1-(5-nitro-2-thiazolyl)-2,3,4,5-tetrahydro-1H-benzazepine
White powder
M.p. 149°–152° C. (recrystallized from dichloromethane-diethyl ether).

7-Chloro-5-oxo-1-(5-nitro-1-pyridylcarbonyl)-2,3,4,5-tetrahydro-1H-benzazepine
Yellow powder
$^1$H-NMR (CDCl$_3$)δ:1.70–2.75 (2H, m), 2.80–3.70 (3H, m), 4.60–5.30 (1 H, m), 6.59 (1 H, d, J=8.3 Hz), 7.15 (1 H, dd, J=2.4, 8.3 Hz), 7.89 (1H, d, J=2.4 Hz), 7.94 (1 H, d, J=8.6 Hz), 8.52 (1 H, dd, J=2.4, 8.5 Hz), 9.02 (1 H, d, J=2.4 Hz).

7-Chloro-5-methyl-1-(6-nitronicotinoyl)-2,3,4,5-tetrahydro-1H-1,5-benzodiazepine
Orange powder
M.p. 162.5°–164° C. (recrystallized from dichloromethane-diethyl ether).

REFERENCE EXAMPLE 4

Using the suitable starting compounds, the following compounds are obtained in the same manner as in Reference Example 2.

7-Chloro-5-methoxycarbonylmethyl-1-(6-aminonicotinoyl)-2,3,4,5-tetrahydro-1H-benzazepine
White powder
M.p. 201°–204° C. (recrystallized from dichloromethane-diethyl ether).

7-Chloro-5-methoxycarbonylmethoxy-1-(6-aminonicotinoyl)-2,3,4,5-tetrahydro-1H-benzazepine
Colorless amorphous
$^1$H-NMR (CDCl$_3$)δ:1.60–2.60 (4H, m), 2.60–3.00 (1H, m), 3.77 (3H, s), 4.05–4.45 (2H, m), 4.50–5.20 (2H, m), 4.70 (2H, s), 6.30 (1 H, d, J=8.6 Hz), 6.60–6.75 (1H, m), 7.05 (1H, d, J=2.4, 8.3 Hz), 7.10–7.70 (2H, m), 7.80–8.15 (1H, m).

7-Chloro-1-(6-aminonicotinoyl)-2,3,4,5-tetrahydro-1H-benzazepine
White powder
M.p. 228°–231° C. (recrystallized from dichloromethane-diethyl ether).

7-Chloro-4-methyl-1-(6-aminonicotinoyl)-2,3,4,5-tetrahydro-1H-1,4-benzodiazepine
Colorless amorphous
$^1$H-NMR (CDCl$_3$)δ:2.41 (3H, s), 3.00 (3H, s), 3.67 (1 H, d, J=14 Hz), 3.99 (1H, d, J=14 Hz), 4.68 (2H, s), 4.80 -5.10 (1H, m), 6.28 (1 H, d, J= 8.6 Hz), 6.66 (1 H, d, J=8.4 Hz), 7.02 (1 H, dd, J=2.4, 8.4 Hz), 7.29 (1 H, d, J=2.3 Hz), 7.32 (1 H, dd, J=2.3, 8.6 Hz), 7.90 (1 H, d, J=2.3 Hz).

7-Chloro-5-oxo-1-(5-aminothenoyl)-2,3,4,5-tetrahydro-1H-benzazepine
Yellow powder
$^1$H-NMR (CDCl$_3$)δ:2.00–2.25 (2H, m), 2.65–2.85 (2H, m), 3.75–4.70 (4H, m), 5.83 (1H, d, J=4.1 Hz), 6.40 (1H, d, J=4.1 Hz), 7.16 (1H, d, J=8.4 Hz), 7.42 (1 H, dd, J=2.5, 8.4 Hz), 7.87 (1 H, d, J=2.5 Hz).

7-Chloro-5-oxo-1-(5-amino-2-furoyl)-2,3,4,5-tetrahydro-1H-benzazepine
Green powder
M.p. 151°–154° C. (recrystallized from dichloromethane-diethyl ether).

7-Chloro-5-oxo-1-(5-amino-2-thiazolyl)-2,3,4,5-tetrahydro-1H-benzazepine
Yellow powder
M.p. 142°–144.5° C. (recrystallized from dichloromethane-diethyl ether).

7-Chloro-5-oxo-1-(5-amino-2-pyridylcarbonyl)-2,3,4,5-tetrahydro-1H-1,5-benzazepine
Yellow powder
M.p. 143°–144.5° C. (recrystallized from dichloromethane-diethyl ether).

7-Chloro-5-methyl-1-(6-aminonicotinoyl)-2,3,4,5-tetrahydro-1H-1,5-benzodiazepine
White powder
M.p. 191°–193° C. (recrystallized from dichloromethane-diethyl ether).

REFERENCE EXAMPLE 5

To a solution of 6-aminonicotinic acid methyl ester (4 g) in pyridine (40 ml) is added with stirring 2-methylbenzoyl chloride (6.73 g) under ice-cooling, and the mixture is stirred at room temperature overnight. To the reaction solution is added water, and the precipitated crystals are collected by filtration, and dried to give 6-(2-methylbenzoylamino)nicotinic acid methyl ester (5.7 g) as white powder.
M.p. 167°–169° C.

REFERENCE EXAMPLE 6

To a solution of 6-(2-methylbenzoylamino)nicotinic acid methyl ester (2.1 g) in methanol (30 ml) is added 5% aqueous sodium hydroxide solution (24 ml), and the mixture is refluxed for two hours. To the reaction solution is added water, and the mixture is made weak acidic with 1N aqueous hydrochloric acid solution, and then, extracted with diethyl ether. The extract is dried over magnesium sulfate, and evaporated under reduced pressure to remove the solvent to give 6-(2-methylbenzoylamino)nicotinic acid (2.1 g) as white powder.
M.p. 235°–238° C.

REFERENCE EXAMPLE 7

Using the suitable starting compounds, there are obtained the following compounds in the same manner as in Reference Example 1.

7-Chloro-5-methoxy-1-(6-nitronicotinoyl)-2,3,4,5-tetrahydro-1H-benzazepine

Yellow powder

M.p. 173°–175° C. (recrystallized from dichloromethane-diethyl ether).

7-Chloro-5-allyloxy-1-(6-nitronicotinoyl)-2,3,4,5-tetrahydro-1H-benzazepine

Yellow powder

M.p. 116°–120° C. (recrystallized from dichloromethane-diethyl ether).

REFERENCE EXAMPLE 8

Using the suitable starting compounds, there are obtained the following compounds in the same manner as in Reference Example 2.

7-Chloro-5-methoxy-1-(6-aminonicotinoyl)-2,3,4,5-tetrahydro-1H-benzazepine

Colorless amorphous $^1$H-NMR (CDCl$_3$)δ:1.40–2.55 (4H, m), 2.55–3.00 (1 H, m), 3.30–3.60 (3H, m), 4.20–5.20 (2H, m), 4.66 (2H, brs), 6.30 (1H, d, J=8.5 Hz), 6.66 (1H, d, J=8.4 Hz), 7.03 (1H, dd, J=2.4, 8.3 Hz), 7.30–7.65 (2H, m), 7,80–8.10 (1H, m).

7-Chloro-5-allyloxy-1-(6-aminonicotinoyl)-2,3,4,5-tetrahydro-1H-benzazepine

Colorless amorphous $^1$H-NMR (CDCl$_3$)δ:1.50–2.60 (4H, m), 2.60–3.00 (1 H, m), 4.00–4.30 (2H, m), 4.40–4.80 (4H, m), 5.00–5.50 (2H, m), 5.80–6.20 (1H, m), 6.29 (1H, d, J=8,4 Hz), 6.65 (1H, d, J=8.3 Hz), 7.03 (1H, dd, J=2.3, 8.3 Hz), 7.10–7.70 (2H, m), 7.80–8.10 (1H, m).

EXAMPLE 1

To a solution of 7-chloro-5-oxo-1-(6-aminonicotinoyl)-2,3,4,5-tetrahydro-1H-benzazepine (0.25 g) in pyridine (2 ml) is added with stirring 2-methylbenzoyl chloride (0.18 g) under ice-cooling, and the mixture is stirred at room temperature for one hour. To the reaction solution is added water, and the mixture is extracted with ethyl acetate. The extract is washed successively with 0.1N aqueous hydrochloric acid solution and water, and dried over magnesium sulfate. The resultant is evaporated under reduced pressure to remove the solvent, and the residue is purified by silica gel column chromatography to give 7-chloro-5-oxo-1-[6-(2-methylbenzoylamino)nicotinoyl] -2,3,4,5-tetrahydro-1H-benzazepine (0.3 g) as colorless amorphous.

$^1$H-NMR (CDCl$_3$)δ:2.0–2.4 (2H, m), 2.50 (3H, s), 2.89 (2H, t, J=6.2 Hz), 3.2–5.0 (2H, br), 6.72 (1H, d, J=8.4 Hz), 7.20–7.51 (5H, m), 7.60 (1H, dd, J=2.3, 8.7 Hz), 7.86 (1H, d, J=2.5 Hz), 8.09 (1H, d, J=1.7 Hz), 8.24 (1H, d, J=8.7 Hz), 8.50 (1 H, s).

EXAMPLE 2

To a solution of 7-chloro-5-oxo-1-[6-(2-methylbenzoylamino)nicotinoyl] -2,3,4,5-tetrahydro-1H-benzazepine (0.3 g) in methanol (5 ml) is added with stirring sodium borohydride (0.05 g) under ice-cooling, and the mixture is stirred at room temperature for one hour. To the reaction solution is added water, and the mixture is extracted with dichloromethane. The extract is washed with water, and dried over magnesium sulfate. The resultant is evaporated under reduced pressure to remove the solvent, and the residue is purified by silica gel column chromatography to give 7-chloro-5-hydroxy-1-[6 -(2-methylbenzoylamino)nicotinoyl]-2,3,4,5-tetrahydro-1H-benzazepine (0.2 g) as colorless amorphous.

$^1$H-NMR (CDCl$_3$)δ:1.60–2.60 (4H, m), 2.46 (3H, s), 2.70–2.95 (1 H, m), 3.73 (1 H, s), 4.65–5.65 (2H, m), 6.57 (1 H, d, J=8.1 Hz), 7.00 (1 H, d, J=6.5 Hz), 7.15–8.40 (8H, m), 8.70–8.90 (1H, m).

EXAMPLE 3

To a suspension of methyltriphenylphosphonium bromide (0.86 g) in tetrahydrofuran (20 ml) is added with stirring potassium t-butoxide (0.23 g) at –5° C., and the mixture is stirred at –5° C. for one hour. To the mixture is added 7-chloro-5-oxo-1-[6-(2-methylbenzoylamino)nicotinoyl]-2, 3,4,5-tetrahydro-1H-benzazepine (0.58 g) at the same temperature, and the mixture is stirred at room temperature for one hour. The reaction mixture is poured into ice-water, and extracted with ethyl acetate. The extract is washed with water, dried over magnesium sulfate, and evaporated under reduced pressure to remove the solvent. The residue is purified by silica gel column chromatography to give 7-chloro-5-methylidene-1-[6-(2-methylbenzoylamino)nicotinoyl]-2,3,4,5 -tetrahydro-1H-benzazepine (0.28 g) as yellow amorphous.

$^1$H-NMR (CDCl$_3$)δ:1.85–2.20 (2H, m), 2.30–3.30 (3H, m), 2.50 (3H, s), 4.75–5.15 (1 H, m), 5.20–5.35 (2H, m), 6.61 (1 H, d, J=8.3 Hz), 7.01 (1 H, dd, J=2.5, 8.4 Hz), 7.20–7.60 (6H, m), 8.06 (1 H, d, J=2 Hz), 8.19 (1 d, J=8.7 Hz), 8.34 (1 H, s).

EXAMPLE 4

To a solution of 7-chloro-5-methylidene-1-[6-(2-methylbenzoylamino)nicotinoyl] -2,3,4,5-tetrahydro-1H-benzazepine (0.28 g) in t-butanol (3 ml), pyridine (0.2 ml) and water (1.2 ml) is added 4% aqueous osmium tetraoxide solution (0.2 ml), and further thereto is added 4-methylmorpholine N-oxide (0.1 g). The mixture is refluxed for 5 hours, and cooled. Saturated aqueous sodium hydrogen sulfite solution is added to the reaction mixture, and the mixture is stirred at room temperature for 30 minutes. Water is added to the reaction solution, and the mixture is extracted with a mixture of ethyl acetate and tetrahydrofuran. The extract is washed with water, dried over magnesium sulfate, and evaporated under reduced pressure to remove the solvent. The residue is purified by silica gel column chromatography to give 7-chloro-5 -hydroxymethyl-5-hydroxy-1-[6-(2-methylbenzoylamino)nicotinoyl]-2,3,4,5 -tetrahydro-1H-benzazepine (0.14 g) as colorless amorphous.

$^1$H-NMR (CDCl$_3$)δ:1.50–2.60 (3H, m), 2.45 (3H, s), 2.60–2.95 (1H, m), 3.60–4.25 (4H, m), 4.70–5.10 (1H, m), 6.54 (1H, d, J=8.3 Hz), 6.99 (1H, dd, J=2.3, 8.3 Hz), 7.10–7.70 (5H, m), 7.82 (1 H, d, J=2.3 Hz), 8.10–8.30 (2H, m), 8.83 (1H, s).

EXAMPLE 5

To a suspension of 7-chloro-5-methoxycarbonylmethyl-1-[6-(2 -methylbenzoylamino)nicotinoyl]-2,3,4,5-tetrahydro-1H-benzazepine (1.6 g) in ethanol (20 ml) is added 5N aqueous sodium hydroxide solution (4 ml), and the mixture is stirred at room temperature for 4 hours. Water is added to the reaction solution, and the mixture is made weak acidic with diluted hydrochloric acid, and extracted with dichloromethane. The extract is washed with water, dried over magnesium sulfate, and evaporated under reduced pressure to remove the solvent. The residue is crystallized from diethyl ether, and further recrystallized from diethyl ether to give 7-chloro-5-carboxymethyl-1-[6-(2 -methylbenzoylamino)nicotinoyl]-2,3,4,5-tetrahydro-1H-benzazepine (1.5 g) as white powder.

M.p. 187°–190° C.

EXAMPLE 6

To a solution of 7-chloro-5-carboxymethyl-1-[6-(2-methylbenzoylamino)nicotinoyl] -2,3,4,5-tetrahydro-1H-benzazepine (0.35 g) in dichloromethane (10 ml) is added with stirring N,N-bis(2-oxo-3-oxazolydinyl)phosphinic chloride (0.24 g) under ice-cooling, and the mixture is stirred at room temperature for 15 minutes. To the mixture are added with stirring dimethylamine hydrochloride (0.078 g) and triethylamine (0.31 ml) under ice-cooling, and the mixture is stirred at room temperature overnight. Water is added to the reaction solution, and the mixture is extracted with dichloromethane. The extract is washed successively with diluted aqueous sodium hydroxide solution and water, dried over magnesium sulfate, and evaporated under reduced pressure to remove the solvent. The residue is purified by silica gel column chromatography, and recrystallized from dichloromethane-diethyl ether to give 7-chloro-5-dimethylaminocarbonylmethyl-1-[6-(2-methylbenzoylamino)nicotinoyl]-2,3,4,5-tetrahydro-1H-benzazepine (0.29 g) as white powder.

M.p. 197°–198.5° C.

EXAMPLE 7

To a suspension of 7-chloro-5-methoxycarbonylmethoxy-1-[6-(2 -methylbenzoylamino)nicotinoyl]-2,3,4,5-tetrahydro-1H-benzazepine (0.4 g) in ethanol (5 ml) is added 5N aqueous sodium hydroxide solution (1 ml), and the mixture is stirred at room temperature for 4 hours. Water is added to the reaction mixture, and the mixture is made weak acidic by adding thereto diluted hydrochloric acid, and extracted with dichloromethane. The extract is washed with water, dried over magnesium sulfate, and evaporated under reduced pressure to remove the solvent. The residue is crystallized from diethyl ether to give 7-chloro-5-carboxymethoxy-1-[6-(2-methylbenzoylamino)nicotinoyl] -2,3,4,5-tetrahydro-1H-benzazepine (0.38 g) as white powder.

M.p. 220°–222° C.

EXAMPLE 8

To a solution of 7-chloro-5-carboxymethoxy-1-[6-(2-methylbenzoylamino)nicotinoyl] -2,3,4,5-tetrahydro-1H-benzazepine (0.3 g) in dichloromethane (10 ml) is added with stirring N,N-bis(2-oxo-3-oxazolidinyl)phosphinic chloride (0.2 g) under ice-cooling, and the mixture is stirred at room temperature for 15 minutes. Subsequently, to the mixture are added with stirring N-methylpiperazine (0.09 ml) and triethylamine (0.17 ml) under ice-cooling, and the mixture is stirred at room temperature overnight. Water is added to the reaction solution, and the mixture is extracted with dichloromethane. The extract is washed with water, dried over magnesium sulfate, and evaporated under reduced pressure to remove the solvent. The residue is purified by silica gel column chromatography to give 7-chloro-5-[(4-methyl-1 -piperazinyl)carbonylmethoxy]-1-[6-(2-methylbenzoylamino)nicotinoyl]-2,3,4,5 -tetrahydro-1H-benzazepine (0.23 g) as colorless amorphous.

$^1$H-NMR (CDCl$_3$)δ:1.60–2.60 (8H, m), 2.29, 2.32 (3H, s), 2.50 (3H, s), 2.70–3.05 (1H, m), 3.40–3.80 (4H, m), 4.10–4.50 (2H, m), 4.55–5.20 (2H, m), 6.60–6.75 (1H, m), 7.00–7.15 (1H, m), 7.15–7.85 (6H, m), 8.10–8.40 (3H, m).

EXAMPLE 9

To a solution of 7-chloro-5-methoxycarbonylmethoxy-1-[6-(2 -methylbenzoylamino)nicotinoyl]-2,3,4,5-tetrahydro-1H-benzazepine (1.2 g) in tetrahydrofuran (15 ml) is added with stirring lithium borohydride (0.1 g) under ice-cooling, and the mixture is stirred at room temperature overnight. Water is added to the reaction solution, and the mixture is extracted with ethyl acetate. The extract is washed with water, dried over magnesium sulfate, and evaporated under reduced pressure to remove the solvent. The residue is purified by silica gel column chromatography to give 7-chloro-5-(2-hydroxyethoxy)- 1-[6-(2-methylbenzoylamino)nicotinoyl]-2,3,4,5-tetrahydro-1H-benzazepine (0.73 g) as colorless amorphous.

$^1$H-NMR (CDCl$_3$)δ:1.50–2.60 (4H, m), 2.51 (3H, s), 2.70–3.05 (1 H, m), 3.50–4.05 (4H, m), 4.50–5.15 (2H, m), 6.60–6.75 (1H, m), 7.00–7.15 (1H, m), 7.20–7.85 (6H, m), 8.10–8.40 (3H, m).

EXAMPLE 10

To a solution of 7-chloro-5-(2-hydroxyethoxy)-1-[6-(2-methylbenzoylamino)nicotinoyl] -2,3,4,5-tetrahydro-1H-benzazepine (0.6 g) in pyridine (5 ml) is added with stirring methanesulfonyl chloride (0.11 ml) under ice-cooling, and the mixture is stirred at room temperature for two hours. Water is added to the reaction solution, and the mixture is extracted with dichloromethane. The extract is washed with water, dried over magnesium sulfate, and evaporated under reduced pressure to remove the solvent. The residue is purified by silica gel column chromatography to give 7-chloro-5-(2-methanesulfonyloxyethoxyl)-1-[6-(2-methylbenzoylamino)nicotinoyl]-2,3,4,5-tetrahydro-1H-benzazepine (0.55 g) as colorless amorphous.

$^1$H-NMR (CDCl$_3$)δ:1.50–2.60 (4H, m), 2.50 (3H, s), 2.70–3.20 (1 H, m), 2.93, 3.13 (3H, s), 3.70–4.05 (2H, m), 4.20–5.20 (4H, m), 6.64 (1H, d, J=8.1 Hz), 7.00–7.10 (1H, m), 7.20–7.85 (6H, m), 8.05–8.40 (3H, m).

EXAMPLE 11

To a solution of 7-chloro-5-(2-methanesulfonyloxyethoxy)-1-[6-(2 -methylbenzoylamino)nicotinoyl]-2,3,4,5-tetrahydro-1H-benzazepine (0.55 g) in dimethylformamide (10 ml) is added potassium phthalimide (0.2 g), and the mixture is stirred at 110° C. for one hour. The reaction solution is poured into ice-water, and the mixture is extracted with dichloromethane. The extract is washed with water, dried over magnesium sulfate, and evaporated under reduced pressure to remove the solvent. The residue is purified by silica gel column chromatography to give 7-chloro-5-(2-phthalimidoethoxy)-1-[6-(2 -methylbenzoylamino)nicotinoyl]-2,3,4,5-tetrahydro-1H-benzazepine (0.4 g) as colorless amorphous.

$^1$H-NMR (CDCl$_3$)δ:1.45–2.55 (4H, m), 2.51 (3H, s), 2.60–2.95 (1H, m), 3.70–4.20 (2H, m), 4.50–5.15 (2H, m), 6.58 (1H, d, J=8.2 Hz), 6.99 (1d, J=8.5 Hz), 7.20–8.50 (15H, m).

EXAMPLE 12

To a solution of 7-chloro-5-(2-phthalimidoethoxy)-1-[6-(2-methylbenzoylamino)nicotinoyl]-2,3,4,5-tetrahydro-1H-benzazepine (0.26 g) in ethanol (10 ml) is added hydrazine hydrate (0.04 ml), and the mixture is refluxed for 2 hours, and cooled. Water is added to the reaction solution, and the mixture is made acidic with diluted hydrochloric acid, and washed with diethyl ether. Aqueous sodium hydroxide solution is added to the aqueous layer in order to make it basic, and the mixture is extracted with dichloromethane. The extract is washed with water, dried over magnesium sulfate, and evaporated under reduced pressure to remove the solvent. The residue is purified by silica gel column chromatography to give 7-chloro-5-(2-aminoethoxy)-1-[6-(2-methylbenzoylamino)nicotinoyl]-2,3,4,5-tetrahydro-1H-benzazepine (0.26 g) as colorless amorphous.

$^1$H-NMR (CDCl$_3$)δ:1.50–2.60 (4H, m), 2.50 (3H, s), 2.65–3.20 (3H, m), 3.40–3.80 (2H, m), 4.45–5.15 (2H, m), 6.62 (1 H, d, J=8.1 Hz), 7.04 (1H, d, J=8.1 Hz), 7.15–7.85 (6H, m), 8.10–8.50 (3H, m).

EXAMPLE 13

To a solution of 7-chloro-5-(2-aminoethoxy)-1-[6-(2-methylbenzoylamino)nicotinoyl]-2,3,4,5-tetrahydro-1H-benzazepine (0.16 g) in methanol (3 ml) are added 37% formaldhyde (0.3 ml) and sodium cyanoborohydride (0.06 g), and further thereto is added with stirring acetic acid (0.25 ml) at 10° C. The mixture is stirred at room temperature for 3 hours, and poured into ice-water. The mixture is made basic with potassium carbonate, and extracted with dichloromethane. The extract is washed with water, dried over magnesium sulfate, and evaporated under reduced pressure to remove the solvent. The residue is purified by silica gel column chromatography to give 7-chloro-5-(2-dimethylaminoethoxy)-1-[6-(2-methylbenzoylamino)nicotinoyl]-2,3,4,5-tetrahydro-1H-benzazepine (58 mg) as colorless amorphous.

$^1$H-NMR (CDCl$_3$)δ:1.50–3.00 (13H, m), 2.50 (3H, s), 3.40–3.85 (2H, m), 4.45–5.15 (2H, m), 6.60 (1H, d, J=8.1 Hz), 7.00–7.10 (1H, m), 7.20–7.90 (6H, m), 8.05–8.60 (3H, m).

EXAMPLE 14

To a solution of 7-chloro-5-(2-aminoethoxyl)-1-[6-(2-methylbenzoylamino)nicotinoyl]-2,3,4,5-tetrahydro-1H-benzazepine (0.14 g) in dichloromethane (5 ml) are added with stirring triethylamine (0.08 ml) and acetyl chloride (0.03 ml) under ice-cooling. The mixture is stirred at room temperature for 30 minutes, and thereto is added water, and the mixture is extracted with dichloromethane. The extract is washed with water, dried over magnesium sulfate, and evaporated under reduced pressure to remove the solvent. The residue is purified by silica gel column chromatography to give 7-chloro-5-(2-acetylaminoethoxy)-1-[6-(2-methylbenzoylamino)nicotinoyl]-2,3,4,5-tetrahydro-1H-benzazepine (85 mg) as colorless amorphous.

$^1$H-NMR (CDCl$_3$)δ:1.60–2.70 (6H, m), 2.50 (3H, s), 2.70–3.00 (1 H, m), 3.00–3.20 (1H, m), 3.40–3.80 (4H, m), 4.50–5.10 (2H, m), 5.95–6.15 (1H, m), 6.65–6.80 (1 H, m), 7.00–7.20 (1 H, m), 7.20–7.80 (6H, m), 8.05–8.50 (3H, m).

EXAMPLE 15

To a suspension of 7-chloro-5-oxo-1-[5-(2-methylbenzoylamino)thenoyl]-2,3,4,5-tetrahydro-1H-benzazepine (1 g) in methanol (40 ml) are added molecular sieve 4A (2 g) and 40% methylamine methanol solution (10 ml), and the mixture is refluxed for 6 hours, and cooled. To the mixture is added with stirring sodium borohydride (0.13 g) at room temperature, and the mixture is stirred at the same temperature overnight. The reaction solution is filtered on Celite, and to the filtrate is added water, and the mixture is extracted with dichloromethane. The extract is washed with water, dried over magnesium sulfate, and evaporated under reduced pressure to remove the solvent. The residue is purified by silica gel column chromatography, and recrystallized from dichloromethane-diethyl ether to give 7-chloro-5-methylamino-1-[5-(2-methylbenzoylamino)thenoyl]-2,3,4,5-tetrahydro-1H-benzazepine (0.93 g) as white powder.

M.p. 213°–216° C. (recrystallized from dichloromethane-diethyl ether).

EXAMPLE 16

To a solution of 7-chloro-5-methylamino-1-[5-(2-methylbenzoylamino)thenoyl]-2,3,4,5-tetrahydro-1H-benzazepine (0.5 g) in methanol (10 ml) are added 37% formaldehyde (0.8 ml) and sodium cyanoborohydride (0.1 g), and further thereto is added dropwise acetic acid (0.6 ml) at a temperature below 10° C. The mixture is stirred at room temperature for one hour, and poured into ice-water. The mixture is made basic with potassium carbonate, and extracted with dichloromethane. The extract is washed with water, dried over magnesium sulfate, and evaporated under reduced pressure to remove the solvent. The residue is purified by silica gel column chromatography to give 7-chloro-5-dimethylamino-1-[5-(2-methylbenzoylamino)thenoyl]-2,3,4,5-tetrahydro-1H-benzazepine (0.41 g) as colorless amorphous.

$^1$H-NMR (CDCl$_3$)δ:1.20–2.60 (10H, m), 2.44 (3H, s), 3.15–3.65 (2H, m), 4.00–5.00 (1H, m), 6.50 (2H, s), 6.90–7.50 (6H, m), 7.67 (1 H, s), 8.73 (1H, s).

EXAMPLE 17

To a suspension of 6-(2-methylbenzoylamino)nicotinic acid (0.3 g) in dimethylformamide (0.5 ml) and dichloromethane (2.5 ml) is added dropwise oxazolyl chloride (0.2 ml), and the mixture is stirred at room temperature for 2 hours. The mixture is evaporated under reduced pressure to remove the solvent to give 6-(2-methylbenzoylamino)nicotinoyl chloride.

To a solution of 7-chloro-5-oxo-2,3,4,5-tetrahydro-1H-benzazepine (0.15 g) in pyridine (5 ml) is added with stirring the above obtained 6-(2-methylbenzoylamino)nicotinoyl chloride, and the mixture is stirred at room temperature for 4 hours. Water is added to the reaction solution, and the mixture is extracted with ethyl acetate. The extract is washed with water, dried over magnesium sulfate, and evaporated under reduced pressure to remove the solvent. The residue is purified by silica gel column chromatography to give 7-chloro-5-oxo-1-[6-(2-methylbenzoylamino)nicotinoyl]-2,3,4,5-tetrahydro-1H-benzazepine (0.16 g) as colorless amorphous.

$^1$H-NMR (CDCl$_3$)δ:2.0–2.4 (2H, m), 2.50 (3H, s), 2.89 (2H, t, J=6.2 Hz), 3.2–5.0 (2H, br), 6.72 (1H, d, J=8.4 Hz), 7.20–7.51 (5H, m), 7.60 (1H, dd, J=2.3, 8.7 Hz), 7.86 (1H, d, J=2.5 Hz), 8.09 (1H, d, J=1.7 Hz), 8.24 (1H, d, J=8.7 Hz), 8.50 (1H, s).

EXAMPLES 18–148

Using the suitable starting compounds, the following compounds listed in Table 1 are obtained in the same manner as in Examples 1 and 17. Table 2 shows the NMR analysis

TABLE 1

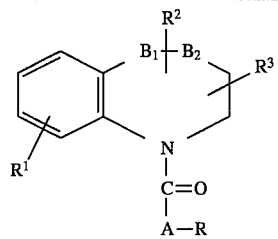

Example 18

Structure:

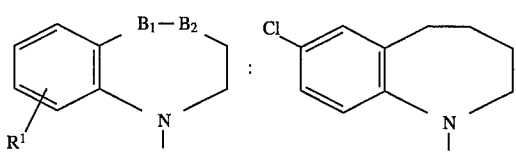

R²: =O (5-position)
R³: H

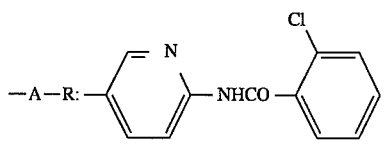

Crystalline form: White powder
Recrystallization solvent: Methanol
Melting point: 172–174.5° C.
Form: Free

Example 19

Structure:

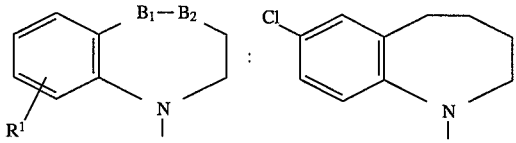

R²: =O (5-position)
R³: H

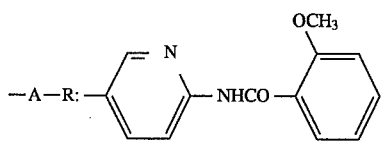

Crystalline form: White powder
Recrystallization solvent: Dichloromethane-diethyl ether
Melting point: 234–237° C.
Form: Free

Example 20

Structure:

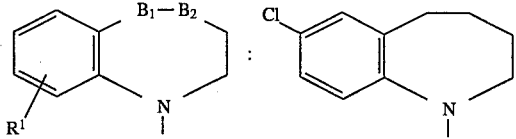

R²: =O (5-position)

TABLE 1-continued

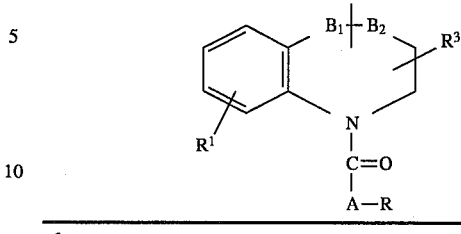

R³: H

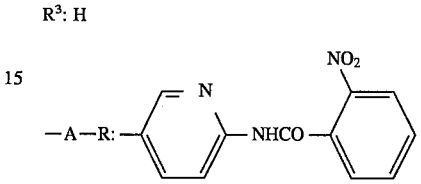

Crystalline form: White powder
Recrystallization solvent: Dichloromethane-diethyl ether
Melting point: 194–196° C.
From: Free

Example 21

Structure

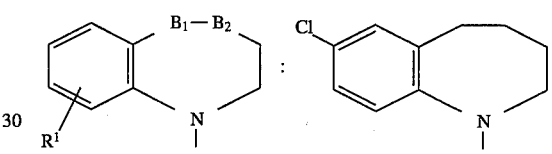

R²: =O (5-position)
R³: H

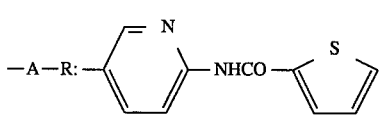

Crystalline form: White powder
Recrystallization solvent: Methanol
Melting point: 206–207° C.
From: Free

Example 22

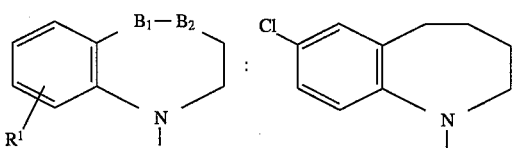

R²: =O (5-position)
R³: H

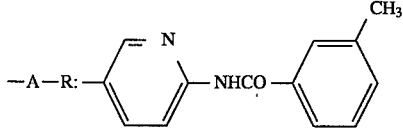

Crystalline form: White powder
Recrystallization solvent: Methanol
Melting point: 169.5–171.5° C.
From: Free

Example 23

Structure:

TABLE 1-continued

[Structure diagram with R², B₁, B₂, R³, R¹, N, C=O, A—R]

| [diagram: B₁—B₂, R¹, N] | : | [diagram: Cl-substituted benzazepine] |

R²: =O (5-position)
R³: H

—A—R: [pyridine]—NHCO—[phenyl]—CH₃

Crystalline form: White powder
Recrystallization solvent: Methanol
Melting point: 169.5–172.5° C.
Form: Free Example 24

Structure:

[diagram: B₁—B₂, R¹, N] : [diagram: Cl-substituted benzazepine, N]

R²: =O (5-position)
R³: H

—A—R: [pyridine]—NHCO—[cyclohexyl]

Crystalline form: White powder
Recrystallization solvent: Methanol
Melting point: 173–174° C.
Form: Free Example 25

Structure:

[diagram: B₁—B₂, R¹, N] : [diagram: Cl-substituted benzazepine, N]

R²: —OH (5-position)
R³: H

—A—NR: [pyridine]—NHCO—[phenyl with o-CH₃]

TABLE 1-continued

[Structure diagram with R², B₁, B₂, R³, R¹, N, C=O, A—R]

Crystalline form: Colorless amorphous
NMR analysis: 1)
Form: Free

Example 26

Structure:

[diagram: B₁—B₂, R¹, N] : [diagram: Cl-substituted benzazepine, N]

R²: —OH (5-position)
R³: H

—A—R: [pyridine]—NHCO—[phenyl with m-CH₃]

Crystalline form: Colorless amorphous
NMR analysis: 2)
Form: Free

Example 27

Structure:

[diagram: B₁—B₂, R¹, N] : [diagram: Cl-substituted benzazepine, N]

R²: —OH (5-position)
R³: H

—A—R: [pyridine]—NHCO—[phenyl]—CH₃

Crystalline form: Colorless amorphous
NMR analysis: 3)
Form: Free

Example 28

Structure:

[diagram: B₁—B₂, R¹, N] : [diagram: Cl-substituted benzazepine, N]

R²: —OH (5-position)
R³: H

TABLE 1-continued

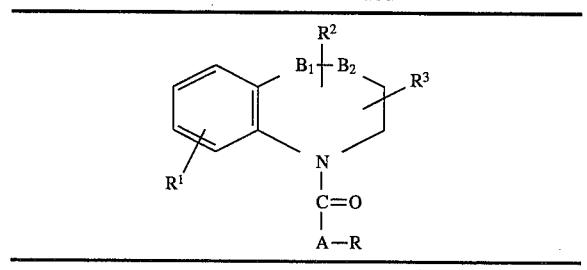

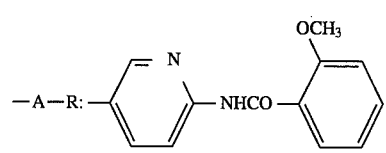

Crystalline form: Colorless amorphous
NMR analysis 4)
Form: Free
Example 29

Structure:

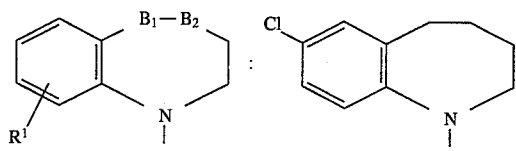

$R^2$: —OH (5-position)
$R^3$: H

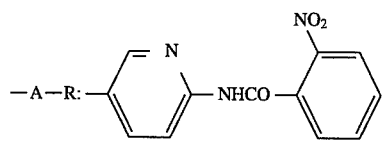

Crystalline form: Colorless amorphous
NMR analysis: 5)
Form: Free
Example 30

Structure:

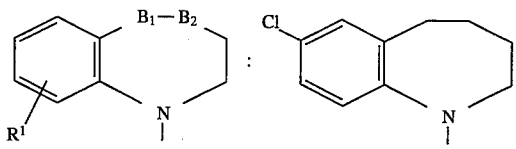

$R^2$: —OH (5-position)
$R^3$: H

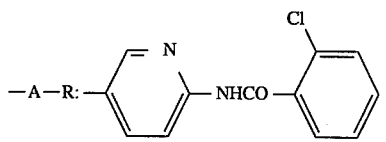

Crystalline form: Colorless amorphous
NMR analysis: 6)
Form: Free
Example 31

Structure:

TABLE 1-continued

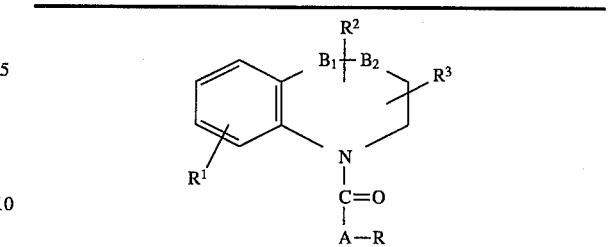

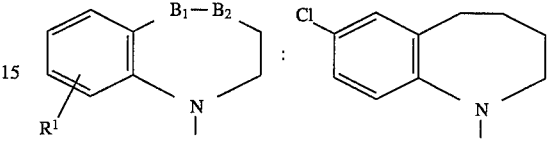

$R^2$: —OH (5-position)
$R^3$: H

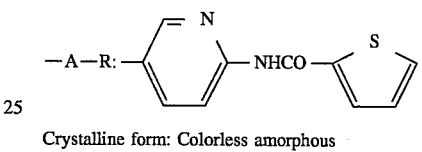

Crystalline form: Colorless amorphous
NMR analysis 7)
Form: Free
Example 32

Structure:

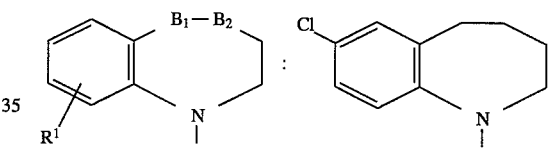

$R^2$: —OH (5-position)
$R^3$: H

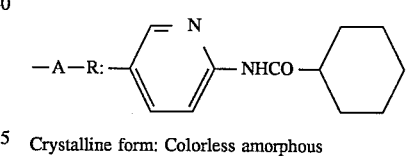

Crystalline form: Colorless amorphous
NMR analysis: 8)
Form: Free
Example 33

Structure:

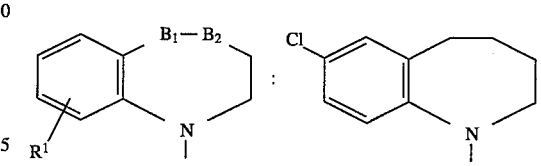

$R^2$: —OH (5-position)
$R^3$: H

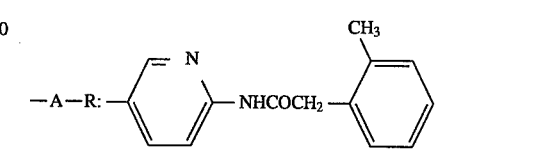

Crystalline form: Colorless amorphous

TABLE 1-continued

[Structure header: phenyl ring with R¹, R², B₁–B₂–R³ chain, N–C(=O)–A–R]

NMR analysis: 9)
Form: Free

Example 34

Structure:

[Structure: phenyl(R¹)(B₁–B₂)–N– : 7-chloro-2,3,4,5-tetrahydro-1H-1-benzazepine]

R²: —OH (5-position)
R³: —CH₂OH (5-position)

—A—R: 4-(pyridin-2-yl)-NHCO-(2-methylphenyl)

Crystalline form: Colorless amorphous
NMR analysis 10)
Form: Free

Example 35

Structure:

[Structure: phenyl(R¹)(B₁–B₂)–N– : 7-chloro-2,3,4,5-tetrahydro-1H-1-benzazepine]

R²: —OCH₂CO—N(piperazine)N—CH₃
(5-position)
R³: H

—A—R: 4-(pyridin-2-yl)-NHCO-(2-methylphenyl)

Crystalline form: Colorless amorphous
NMR analysis: 11)
Form: Free

Example 36

Structure:

TABLE 1-continued

[Structure header: phenyl ring with R¹, R², B₁–B₂–R³ chain, N–C(=O)–A–R]

[Structure: phenyl(R¹)(B₁–B₂)–N– : 7-chloro-2,3,4,5-tetrahydro-1H-1-benzazepine]

R²: —OCH₂CH₂OH (5-position)
R³: H

—A—R: 4-(pyridin-2-yl)-NHCO-(2-methylphenyl)

Crystalline form: Colorless amorphous
NMR analysis: 12)
Form: Free

Example 37

Structure:

[Structure: phenyl(R¹)(B₁–B₂)–N– : 7-chloro-2,3,4,5-tetrahydro-1H-1-benzazepine]

R²: —OCH₂CH₂N(CH₃)₂ (5-position)
R³: H

—A—R: 4-(pyridin-2-yl)-NHCO-(2-methylphenyl)

Crystalline form: Colorless amorphous
NMR analysis 13)
Form: Free

Example 38

Structure:

[Structure: phenyl(R¹)(B₁–B₂)–N– : 7-chloro-2,3,4,5-tetrahydro-1H-1-benzazepine]

R²: —OCH₂CH₂NHCOCH₃ (5-position)
R³: H

TABLE 1-continued $$\text{[Structure with R}^1\text{, R}^2\text{, R}^3\text{, B}_1\text{, B}_2\text{, A—R, C=O]}$$

−A—R: [pyridine-NHCO-(2-methylphenyl)]

Crystalline form: Colorless amorphous
NMR analysis: 14)
Form: Free
Example 39

Structure:

[Structure: phenyl-B₁—B₂-ethylene-N / 7-chloro-2,3,4,5-tetrahydro-1H-1-benzazepine]

R²: —CH₂COOH (5-position)
R³: H

−A—R: [pyridine-NHCO-(2-methylphenyl)]

Crystalline form: White powder
Recrystallization solvent: Dichloromethane-diethyl ether
Melting point: 187–190° C.
Form: Free
Example 40

Structure:

[Structure: phenyl-B₁—B₂-ethylene-N / 7-chloro-2,3,4,5-tetrahydro-1H-1-benzazepine]

R²: —CH₂CONH₂ (5-position)
R³: H

−A—R: [pyridine-NHCO-(2-methylphenyl)]

Crystalline form: White powder
Recrystallization solvent: Dichloromethane-diethyl ether
Melting point: 141–144° C.
Form: Free
Example 41

Structure:

TABLE 1-continued $$\text{[Structure with R}^1\text{, R}^2\text{, R}^3\text{, B}_1\text{, B}_2\text{, A—R, C=O]}$$

[Structure: phenyl-B₁—B₂-ethylene-N / 7-chloro-2,3,4,5-tetrahydro-1H-1-benzazepine]

R²: —CH₂CON(CH₃)₂ (5-position)
R³: H

−A—R: [pyridine-NHCO-(2-methylphenyl)]

Crystalline form: White powder
Recrystallization solvent: Dichloromethane-diethyl ether
Melting point: 197–198.5° C.
Form: Free
Example 42

Structure:

[Structure: phenyl-B₁—B₂-ethylene-N / 7-chloro-2,3,4,5-tetrahydro-1H-1-benzazepine]

R²: —CH₂CO—N(piperazine)N—CH₃
   (5-position)

R³: H

−A—R: [pyridine-NHCO-(2-methylphenyl)]

Crystalline form: Colorless amorphous
NMR analysis: 15)
Form: Free
Example 43

Structure:

[Structure: phenyl-B₁—B₂-ethylene-N / 7-chloro-2,3,4,5-tetrahydro-1H-1-benzazepine]

R²: H
R³: H

TABLE 1-continued

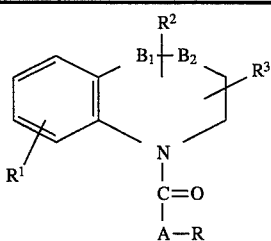

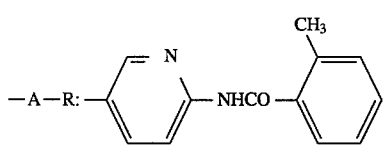

Crystalline form: White powder
Recrystallization solvent: Dichloromethane-diethyl ether
Melting point: 194–197° C.
Form: Free Example 44

Structure:

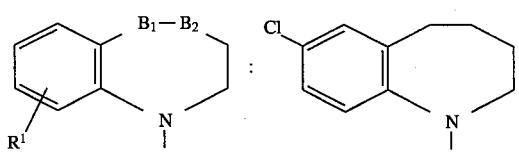

$R^2$: H
$R^3$: H

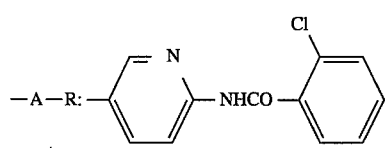

Crystalline form: White powder
Recrystallization solvent: Dichloromethane-diethyl ether
Melting point: 193–195° C.
Form: Free Example 45

Structure:

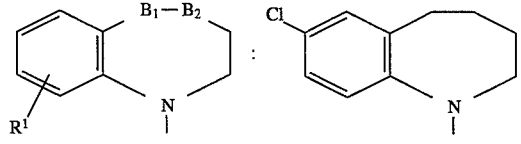

$R^2$: H
$R^3$: H

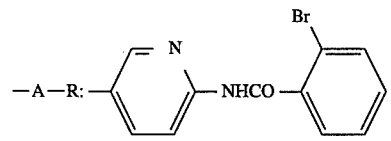

Crystalline form: Yellow powder
Recrystallization solvent: Dichloromethane-diethyl ether
Melting point: 205.5–208.5° C.
Form: Free TABLE 1-continued

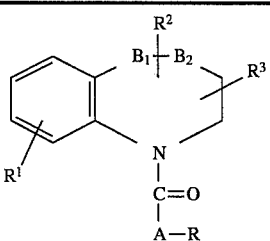

Example 46

Structure:

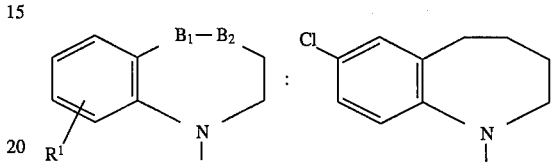

$R^2$: H
$R^3$: H

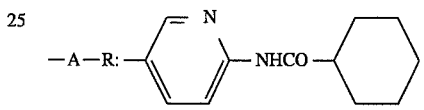

Crystalline form: White powder
Recrystallization solvent: Dichloromethane-diethyl ether
Melting point: 182–183.5° C.
Form: Free Example 47

Structure:

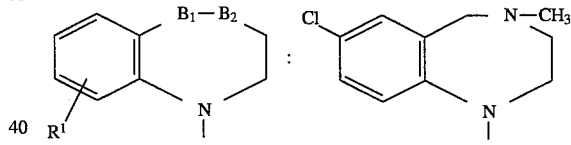

$R^2$: H
$R^3$: H

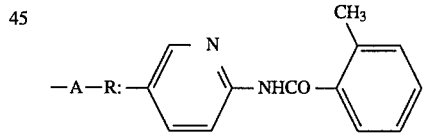

Crystalline form: Colorless amorphous
NMR analysis: 16)
Form: Free

Example 48

Structure:

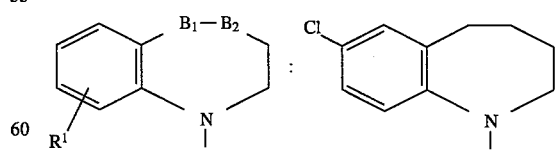

$R^2$: —OH (5-position)
$R^3$: H

TABLE 1-continued

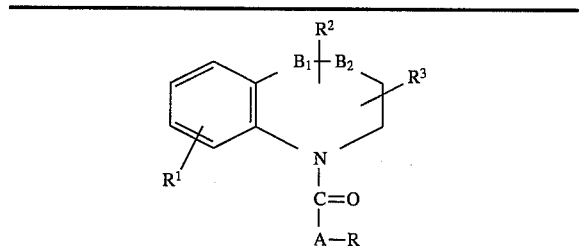

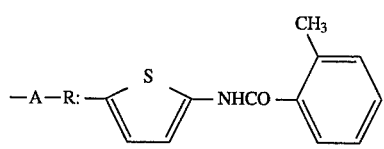

Crystalline form: White powder
Recrystallization solvent: Dichloromethane-diethyl ether
Melting point: 238.5–240° C.
Form: Free
Example 49

Structure:

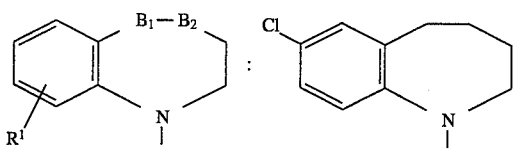

R²: —OH (5-position)
R³: H

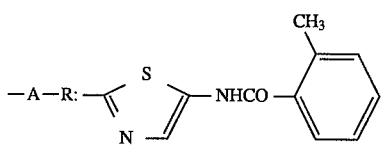

Crystalline form: White powder
Recrystallization solvent: Dichloromethane-diethyl ether
Melting point: 235–237° C.
Form: Free
Example 50

Structure:

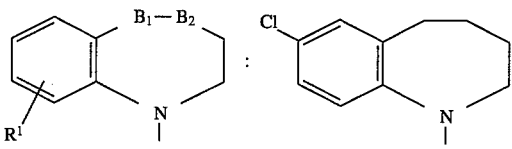

R²: —OH (5-position)
R³: H

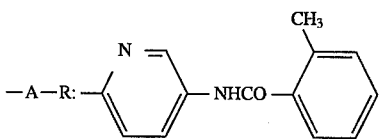

Crystalline form: White powder
Recrystallization solvent: Dichloromethane-diethyl ether
Melting point: 196–199° C.
Form: Free
Example 51

TABLE 1-continued

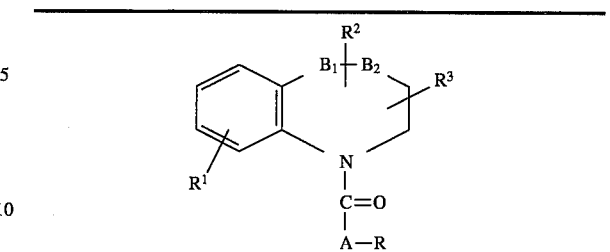

Structure:

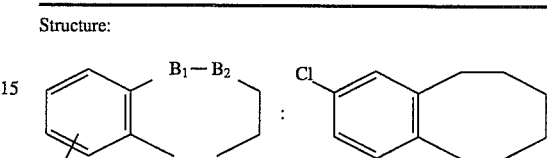

R²: —OH (5-position)
R³: H

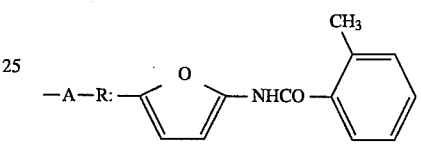

Crystalline form: White powder
Recrystallization solvent: Dichloromethane-diethyl ether
Melting point: 180–183° C.
Form: Free
Example 52

Structure:

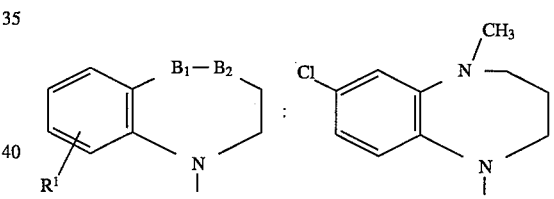

R²: H
R³: H

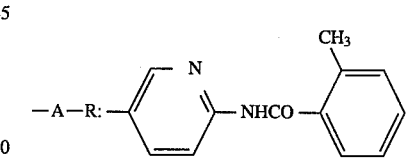

Crystalline form: White powder
Recrystallization solvent: Dichloromethane-diethyl ether
Melting point: 167–169.5° C.
Form: Free
Example 53

Structure:

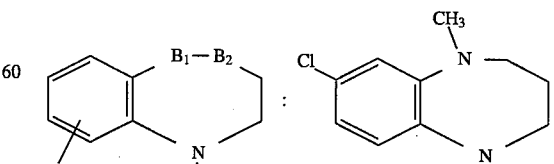

R²: H

TABLE 1-continued

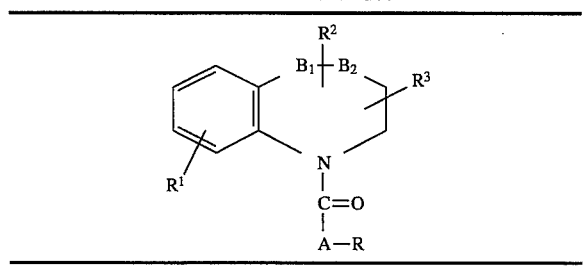

R³: H

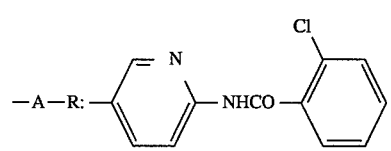

Crystalline form: Colorless amorphous
NMR analysis: 17)
Form: Free
Example 54

Structure:

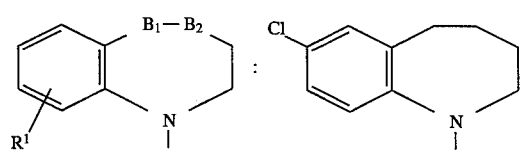

R²: —NHCH₃ (5-position)
R³: H

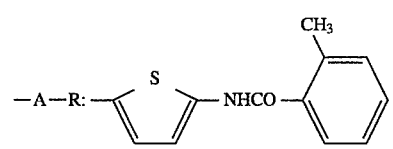

Crystalline form: White powder
Recrystallization solvent: Dichloromethane-diethyl ether
Melting point: 213–216° C.
Form: Free
Example 55

Structure:

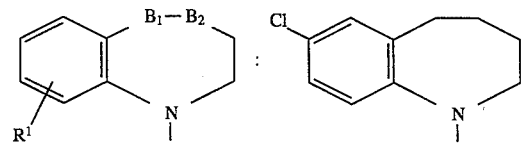

R²: —N(CH₃)₂ (5-position)
R³: H

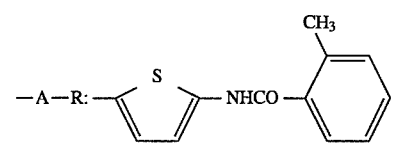

Crystalline form: Colorless amorphous
NMR analysis: 18)
Form: Free
Example 56

Structure:

TABLE 1-continued

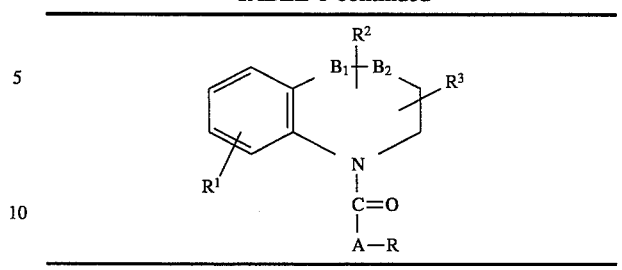

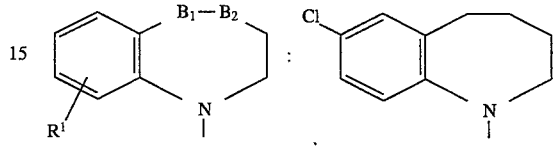

R²: =CH₂ (5-position)
R³: H

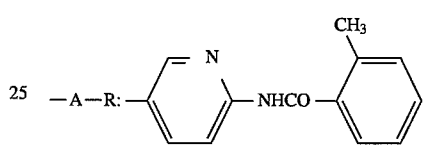

Crystalline form: Yellow amorphous
NMR analysis: 19)
Form: Free
Example 57

Structure:

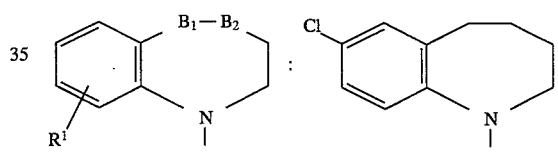

R²: =O (5-position)
R³: H

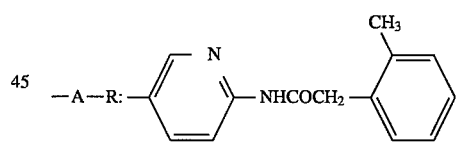

Crystalline form: Colorless amorphous
NMR analysis: 20)
Form: Free
Example 58

Structure:

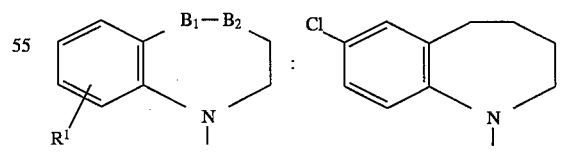

R²: —CH₂CO₂CH₃ (5-position)
R³: H

TABLE 1-continued

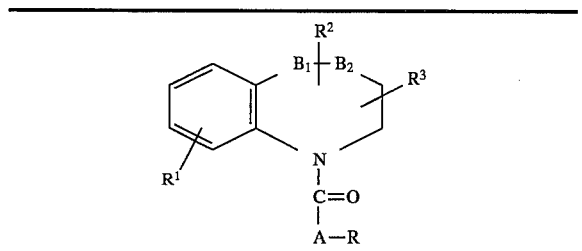

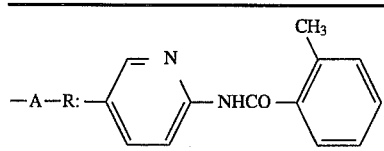

Crystalline form: White powder
NMR analysis: 21)
Form: Free
Example 59

Structure:

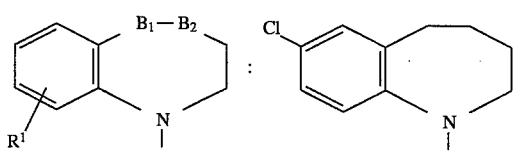

$R^2$: —OCH$_2$CO$_2$CH$_3$ (5-position)
$R^3$: H

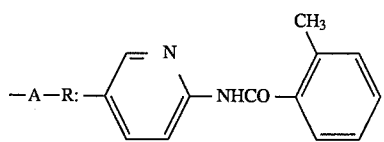

Crystalline form: White powder
Recrystallization solvent: Dichloromethane-diethyl ether
Melting point: 182–184° C.
Form: Free
Example 60

Structure:

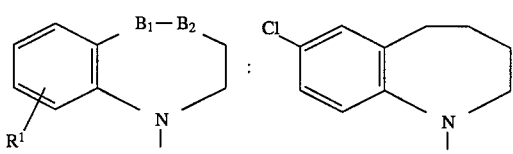

$R^2$: —OCH$_2$COOH (5-position)
$R^3$: H

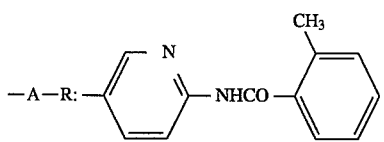

Crystalline form: White powder
Recrystallization solvent: Diethyl ether
Melting point: 220–222° C.
Form: Free
Example 61

Structure:

TABLE 1-continued

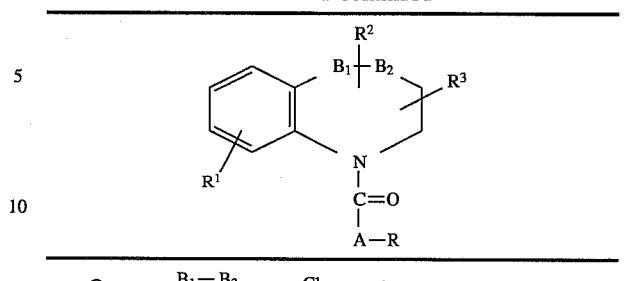

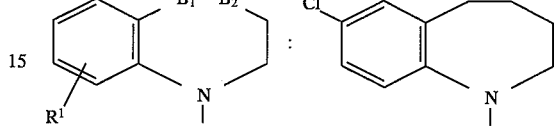

$R^2$: —OCH$_2$CH$_2$OSO$_2$CH$_3$ (5-position)
$R^3$: H

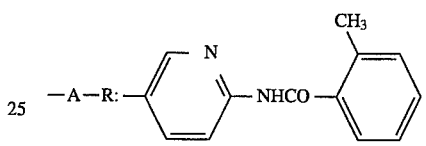

Crystalline form: Colorless amorphous
NMR analysis: 22)
Form: Free
Example 62

Structure:

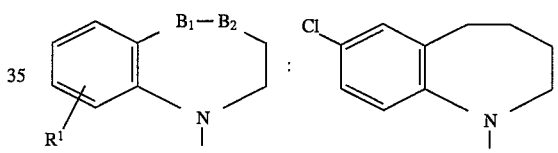

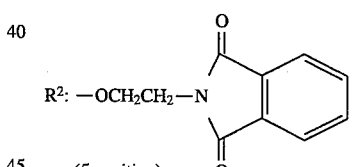

$R^3$: H

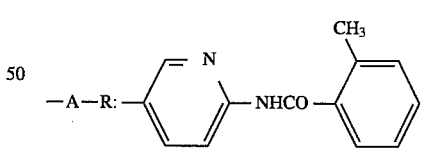

Crystalline form: Colorless amorphous
NMR analysis: 23)
Form: Free
Example 63

Structure:

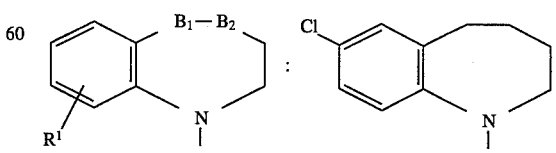

$R^2$: —OCH$_2$CH$_2$NH$_2$ (5-position)

TABLE 1-continued

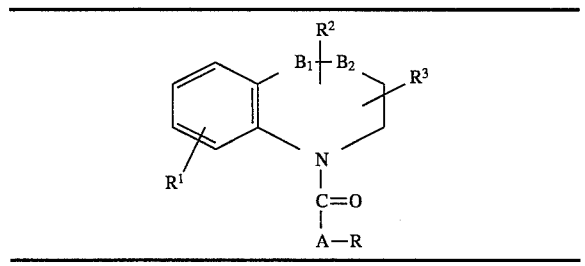

R³: H

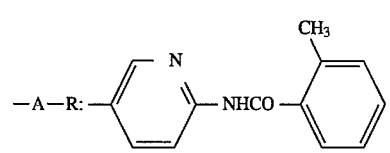

Crystalline form: Colorless amorphous
NMR analysis: 24)
Form: Free
Example 64

Structure:

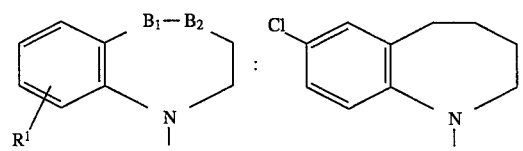

R²: =O (5-position)
R³: H

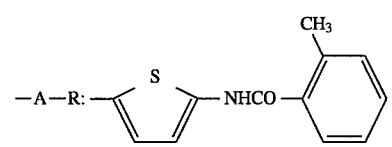

Crystalline form: White powder
Recrystallization solvent: Dichloromethane-diethyl ether
Melting point: 207–210° C.
Form: Free
Example 65

Structure:

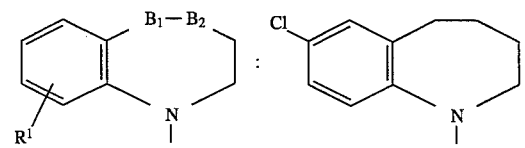

R²: =O (5-position)
R³: H

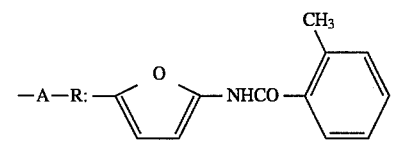

Crystalline form: Yellow powder
Recrystallization solvent: Dichloromethane-diethyl ether
Melting point: 225–228° C.
Form: Free
Example 66

Structure:

TABLE 1-continued

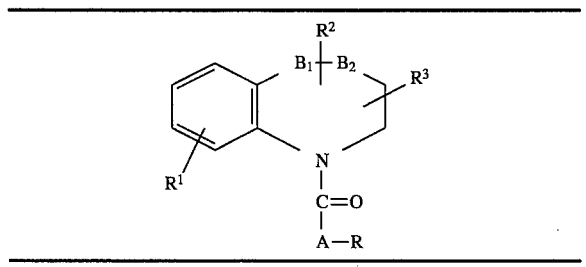

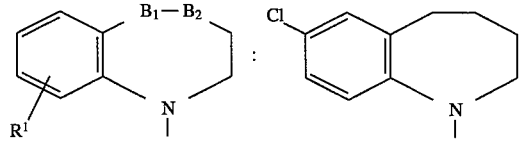

R²: =O (5-position)
R³: H

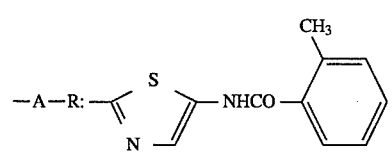

Crystalline form: Yellow powder
Recrystallization solvent: Dichloromethane-diethyl ether
Melting point: 182.5–185.5° C.
Form: Free
Example 67

Structure:

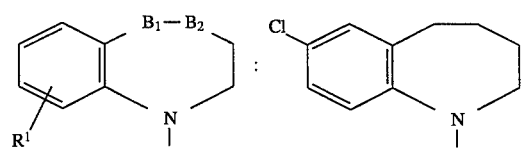

R²: =O (5-position)
R³: H

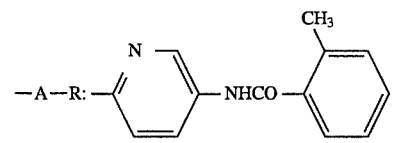

Crystalline form: White powder
Recrystallization solvent: Dichloromethane-diethyl ether
Melting point: 183–184.5° C.
Form: Free
Example 68

Structure:

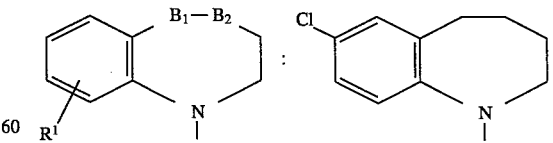

R²: =O (5-position)
R³: H

TABLE 1-continued

[Structure: phenyl ring with B₁-B₂-R³ chain, N-C(=O)-A-R, R¹, R²]

−A−R:
[pyridine-NHCO-phenyl-COOCH₃]

Crystalline form: White powder
Recrystallization solvent: Dichloromethane-diethyl ether
Melting point: 160–162° C.
Form: Free

Example 69

Structure:

[B₁-B₂ benzazepine : chloro-benzazepine]

R²: −OH (5-position)
R³: H

−A−R:
[pyridine-NHCO-phenyl-COOCH₃]

Crystalline form: Colorless amorphous
NMR analysis: 25)
Form: Free

Example 70

Structure:

[B₁-B₂ benzazepine : chloro-benzazepine]

R²: −OH (5-position)
R³: H

−A−R:
[pyridine-NHCO-phenyl-COOH]

Crystalline form: White powder
Recrystallization solvent: Dichloromethane - methanol
Melting point: 153–155° C.
Form: Free

Example 71

Structure:

[B₁-B₂ benzazepine : chloro-benzazepine]

R²: −OCH₃ (5-position)
R³: H

−A−R:
[pyridine-NHCO-phenyl-CH₃]

Crystalline form: White powder
Recrystallization solvent: Dichloromethane-diethyl ether
Melting point: 171–174° C.
Form: Free

Example 72

Structure:

[B₁-B₂ benzazepine : chloro-benzazepine]

R²: −OCH₃ (5-position)
R³: H

−A−R:
[pyridine-NHCO-phenyl-Cl]

Crystalline form: White powder
Recrystallization solvent: Dichloromethane-diethyl ether
Melting Point: 176–178° C.
Form: Free

Example 73

Structure:

[B₁-B₂ benzazepine : chloro-benzazepine]

R²: −OCH₃ (5-position)
R³: H

TABLE 1-continued

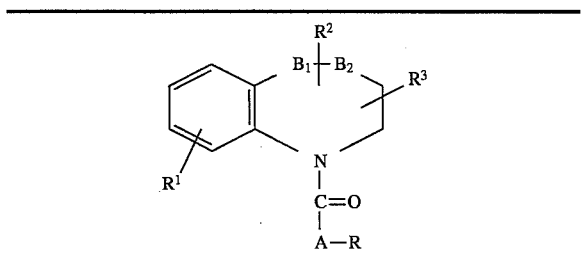

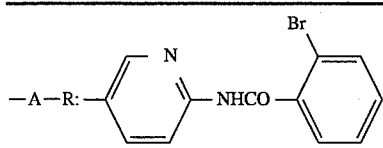

Crystalline form: White powder
Recrystallization solvent: Dichloromethane-diethyl ether
Melting point: 184–186° C.
Form: Free
Example 74

Structure:

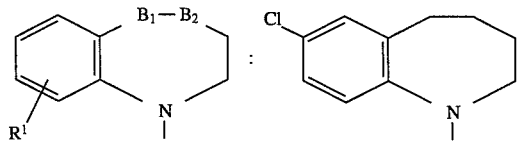

$R^2$: —OCH$_2$CH=CH$_2$ (5-position)
$R^3$: H

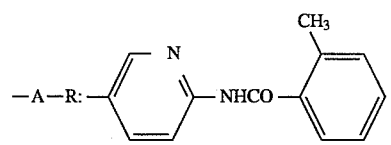

Crystalline form: White powder
NMR analysis: 54)
Form: Free
Example 75

Structure:

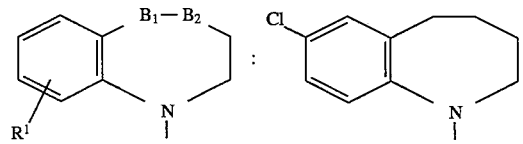

$R^2$: —OCH$_2$CH=CH$_2$ (5-position)
$R^3$: H

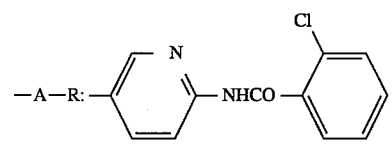

Crystalline form: White powder
Recrystallization solvent: Dichloromethane-diethyl ether
Melting Point: 152–154° C.
Form: Free
Example 76

Structure:

TABLE 1-continued

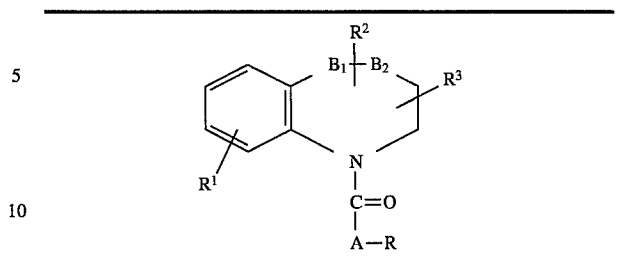

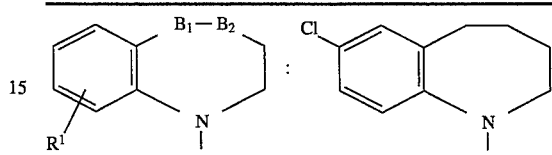

$R^2$: —OCH$_2$CH=CH$_2$ (5-position)
$R^3$: H

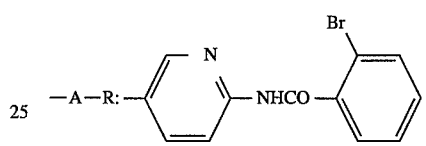

Crystalline form: White powder
Recrystallization solvent: Dichloromethane-diethyl ether
Melting point: 183–186° C.
Form: Free
Example 77

Structure:

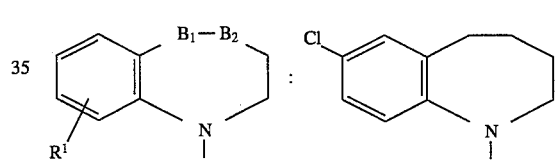

$R^2$: —NH—◁
(5-position)

$R^3$: H

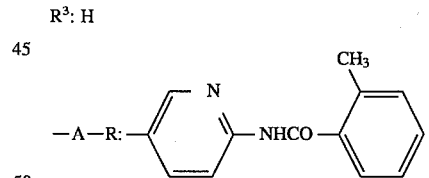

Crystalline form: White powder
NMR analysis: 55)
Form: Free
Example 78

Structure:

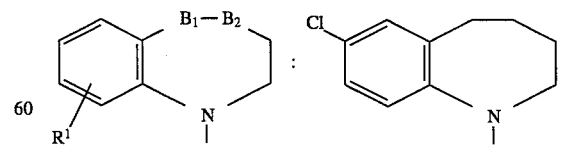

$R^2$: —NH—◁
(5-position)

TABLE 1-continued

[Structure diagram: phenyl ring with R¹, B₁-B₂, R², R³, N-C(=O)-A-R]

R³: H

—A—R: [pyridine-NHCO-(2-chlorophenyl)]

Crystalline form: White powder
Recrystallization solvent: Dichloromethane-diethyl ether
Melting Point: 162–165° C.
Form: Free Example 79

Structure:

[Structure diagram: benzazepine fragment with R¹, B₁-B₂ : 7-chloro-tetrahydrobenzazepine]

R²: —NHCH₃ (5-position)
R³: H

—A—R: [pyridine-NHCO-(2-methylphenyl)]

Crystalline form: White powder
Recrystallization solvent: Dichloromethane-diethyl ether
Melting point: 172–175° C.
Form: Free Example 80

Structure:

[Structure diagram: benzazepine fragment with R¹, B₁-B₂ : 7-chloro-tetrahydrobenzazepine]

R²: —NHCH₃ (5-position)
R³: H

—A—R: [pyridine-NHCO-(2-chlorophenyl)]

Crystalline form: White powder
Recrystallization solvent: Dichloromethane-diethyl ether
Melting point: 162–165° C.
Form: Free TABLE 1-continued

[Structure diagram: phenyl ring with R¹, B₁-B₂, R², R³, N-C(=O)-A-R]

Example 81

Structure:

[Structure diagram: benzazepine fragment with R¹, B₁-B₂ : 7-chloro-tetrahydrobenzazepine]

R²: —N(CH₃)₂ (5-position)
R³: H

—A—R: [pyridine-NHCO-(2-methylphenyl)]

Crystalline form: White powder
Recrystallization solvent: Dichloromethane-diethyl ether
Melting Point: 200–202° C.
Form: Free Example 82

Structure:

[Structure diagram: benzazepine fragment with R¹, B₁-B₂ : 7-chloro-tetrahydrobenzazepine]

R²: H
R³: H

—A—R: [pyridine-NHCO-(2-OCH₂CO₂C₂H₅-phenyl)]

Crystalline form: White powder
Recrystallization solvent: Dichloromethane-diethyl ether
Melting point: 187–189° C.
Form: Free Example 83

Structure:

[Structure diagram: benzazepine fragment with R¹, B₁-B₂ : 7-chloro-tetrahydrobenzazepine]

TABLE 1-continued

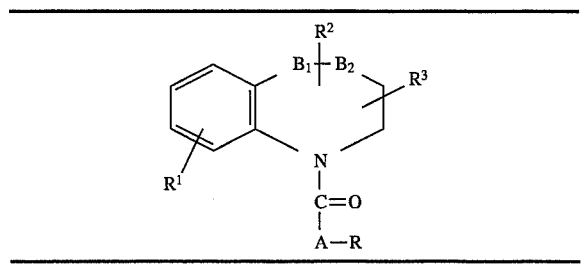

R²: H
R³: H

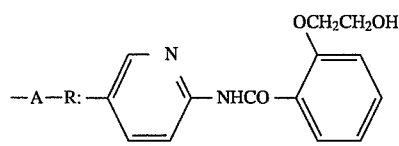

Crystalline form: White powder
Recrystallization solvent: Dichloromethane-diethyl ether
Melting point: 213–216° C.
Form: Free Example 84

Structure:

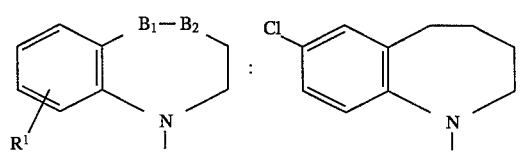

R²: H
R³: H

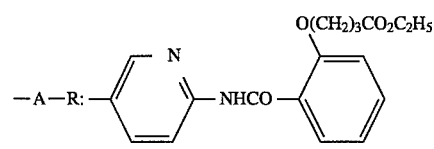

Crystalline form: White powder
Recrystallization solvent: Dichloromethane-diethyl ether
Melting Point: 122–125° C.
Form: Free Example 85

Structure:

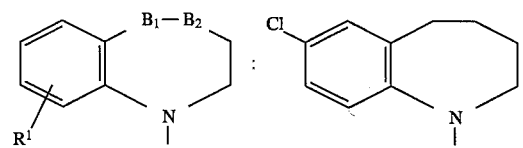

R²: H
R³: H

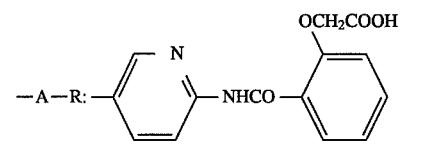

Crystalline form: White powder
Recrystallization solvent: Dichloromethane -diethyl ether
Melting point: 155–157° C.
Form: Free TABLE 1-continued

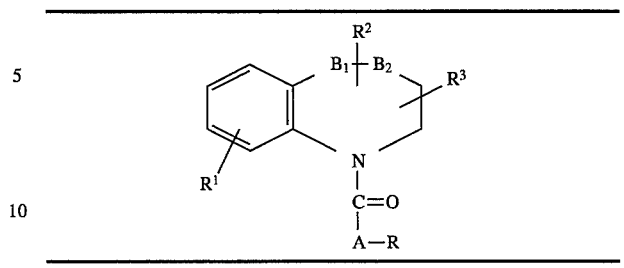

Example 86

Structure:

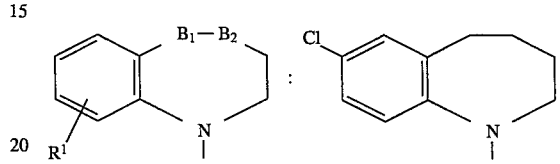

R²: H
R³: H

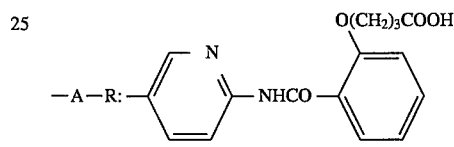

Crystalline form: White powder
Recrystallization solvent: Dichloromethane-diethyl ether
Melting point: 182–184° C.
Form: Free Example 87

Structure:

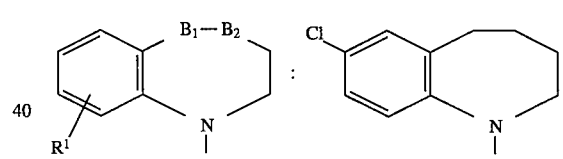

R²: H
R³: H

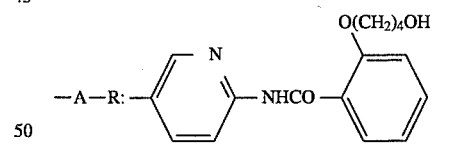

Crystalline form: White powder
Recrystallization solvent: Dichloromethane-diethyl ether
Melting Point: 157–158.5° C.
Form: Free Example 88

Structure:

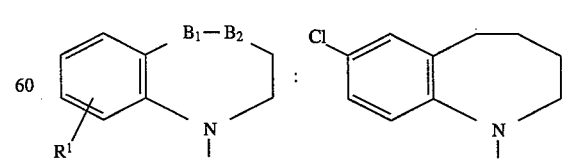

R²: H

TABLE 1-continued

[Structure diagram: benzene ring fused system with R¹, R², R³, B₁, B₂, N-C(=O)-A-R substituents]

R³: H

—A—R:
[pyridine ring connected via NHCO to benzene ring with OCH₂CO—N(piperazine)N—CH₃ substituent]

Crystalline form: White powder
Recrystallization solvent: Dichloromethane-diethyl ether
Melting point: 111–114° C.
Form: Free Example 89

Structure:

[Bicyclic structure with B₁—B₂, R¹, N, and Cl-substituted benzazepine linked]

R²: H
R³: H

—A—R:
[pyridine ring connected via NHCO to benzene ring with O(CH₂)₃CO—N(piperazine)N—CH₃ substituent]

Crystalline form: White powder
Recrystallization solvent: Dichloromethane-diethyl ether
Melting point: 127–130° C.
Form: Free Example 90

Structure:

[Bicyclic structure with B₁—B₂, R¹, N, and Cl-substituted benzazepine linked]

R²: H
R³: H

—A—R:
[pyridine ring connected via NHCO to benzene ring with O(CH₂)₂OSO₂CH₃ substituent]

TABLE 1-continued

[Structure diagram: benzene ring fused system with R¹, R², R³, B₁, B₂, N-C(=O)-A-R substituents]

Crystalline form: White powder
NMR analysis: 26)
Form: Free

Example 91

Structure:

[Bicyclic structure with B₁—B₂, R¹, N, and Cl-substituted benzazepine linked]

R²: H
R³: H

—A—R:
[pyridine ring connected via NHCO to benzene ring with O(CH₂)₂NHCH(CH₃)₂ substituent]

Crystalline form: White powder
NMR analysis: 27)
Form: 2 HCl

Example 92

Structure:

[Bicyclic structure with B₁—B₂, R¹, N, and Cl-substituted benzazepine linked]

R²: H
R³: H

—A—R:
[pyridine ring connected via NHCO to benzene ring with O(CH₂)₂—N(piperidine)—NHCOCH₃ substituent]

Crystalline form: White powder
Recrystallization solvent: Dichloromethane-diethyl ether
Melting point: 159–162° C.
Form: Free Example 93

Structure:

TABLE 1-continued

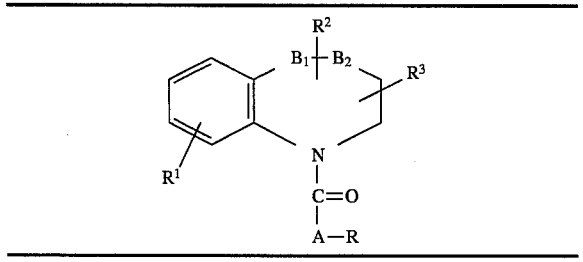

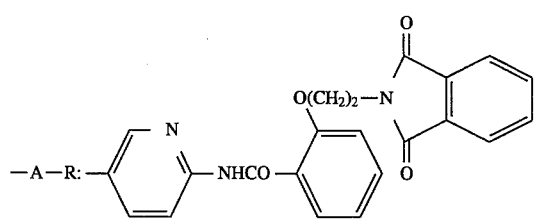

R²: H
R³: H

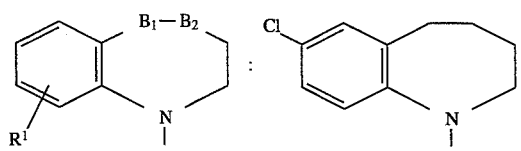

Crystalline form: White powder
NMR analysis: 28)
Form: Free
Example 94

Structure:

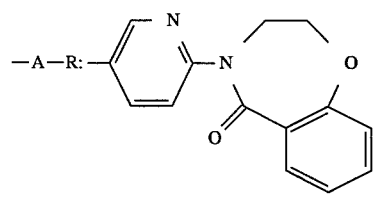

R²: H
R³: H

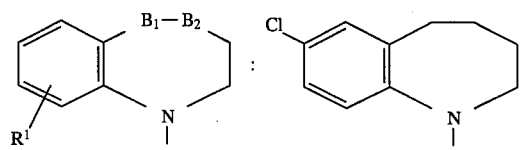

Crystalline form: White powder
Recrystallization solvent: Ethyl acetate
Melting point: 176–179° C.
Form: Free
*)This compound is obtained only by the process of Example 17.
Example 95

Structure:

TABLE 1-continued

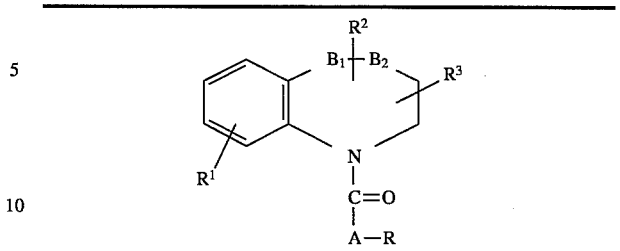

R²: H
R³: H

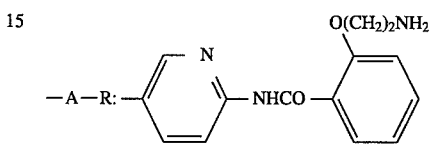

Crystalline form: White powder
NMR analysis: 29)
Form: Free
Example 96

Structure:

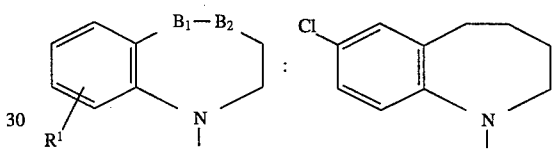

R²: H
R³: H

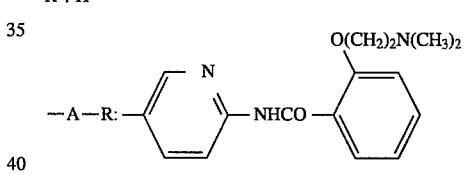

Crystalline form: White powder
NMR analysis: 30)
Form: 2 HCl
Example 97

Structure:

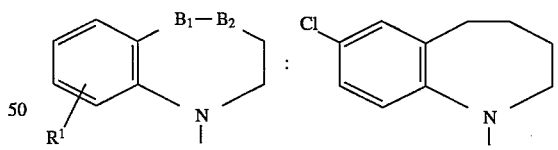

R²: H
R³: H

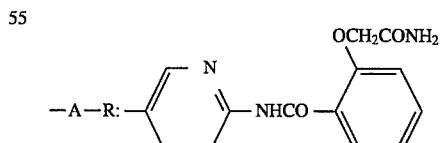

Crystalline form: White powder
Recrystallization solvent: Dichloromethane-diethyl ether
Melting point: 204–207° C.
Form: Free
Example 98

Structure:

TABLE 1-continued

[Structure with R², B₁-B₂, R³, R¹, N, C=O, A-R]

B₁—B₂: —CH₂CH₂CH₂— (phenyl ring on left with R¹); Right: 7-chloro-2,3,4,5-tetrahydro-1H-1-benzazepine R²: —CH₂CO₂CH₃ (5-position)
R³: H —A—R: pyridine-N—NHCO—(2-chlorophenyl)

Crystalline form: White powder
Recrystallization solvent: Dichloromethane-diethyl ether
Melting point: 167–170° C.
Form: Free
Example 99

Structure:

[Structure]

R²: —CH₂COOH (5-position)
R³: H

—A—R: pyridine-N—NHCO—(2-chlorophenyl)

Crystalline form: White powder
Recrystallization solvent: Dichloromethane-diethyl ether
Melting Point: 224–227° C.
Form: Free
Example 100

Structure:

[Structure]

R²: —CH₂COOCH₃ (5-position)
R³: H

—A—R: pyridine-N—NHCO—(2-bromophenyl)

Crystalline form: White powder
Recrystallization solvent: Dichloromethane-diethyl ether
Melting point: 185–188° C.
Form: Free
Example 101

Structure:

[Structure]

R²: —CH₂COOH (5-position)
R³: H

—A—R: pyridine-N—NHCO—(2-bromophenyl)

Crystalline form: White powder
Recrystallization solvent: Ethyl acetate-diethyl ether
Melting point: 221–223° C.
Form: Free
Example 102

Structure:

[Structure]

R²: —CH₂CONHCH₃ (5-position)
R³: H

—A—R: pyridine-N—NHCO—(2-methylphenyl)

Crystalline form: White powder
Recrystallization solvent: Dichloromethane-diethyl ether
Melting Point: 134–137° C.
Form: Free
Example 103

Structure:

TABLE 1-continued

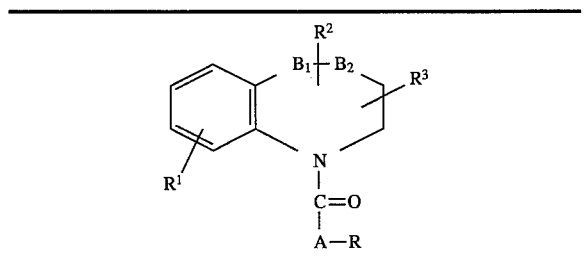

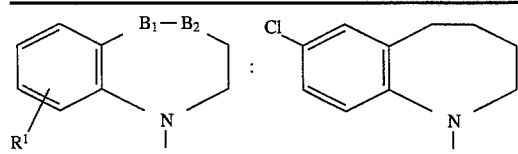

R²: —CH₂CONHC₂H₅ (5-position)
R³: H

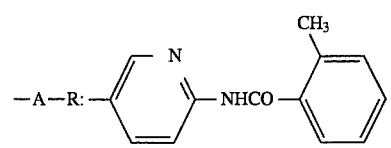

Crystalline form: White powder
Recrystallization solvent: Dichloromethane-diethyl ether
Melting point: 196–199° C.
Form: Free
Example 104

Structure:

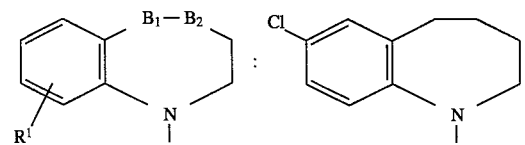

R²: 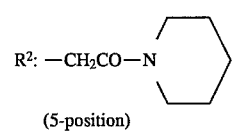

(5-position)
R³: H

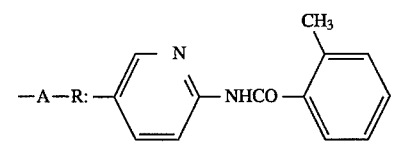

Crystalline form: White powder
Recrystallization solvent: Dichloromethane-diethyl ether
Melting point: 254–256° C.
Form: Free
Example 105

Structure:

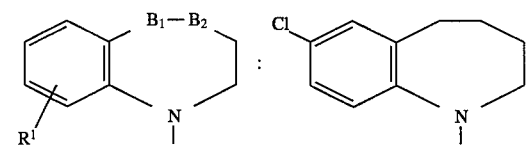

TABLE 1-continued

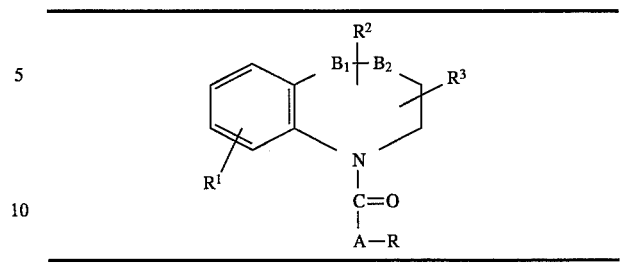

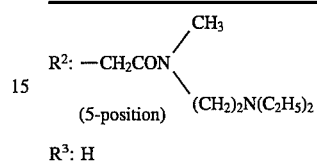

R³: H

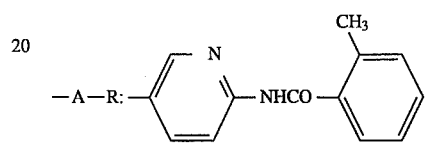

Crystalline form: White powder
Recrystallization solvent: Dichloromethane-diethyl ether
Melting Point: 156–158° C.
Form: Free
Example 106

Structure:

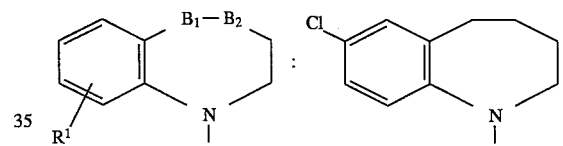

R²: —CH₂CONH(CH₂)₂—
 —N(CH₃)₂
 (5-position)
R³: H

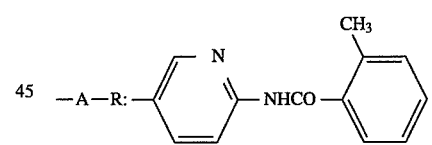

Crystalline form: Colorless amorphous
NMR analysis: 31)
Form: Free
Example 107

Structure:

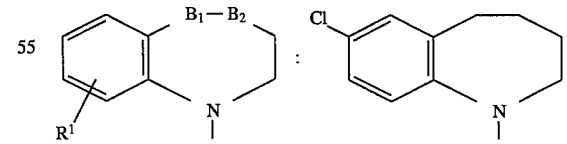

R²: 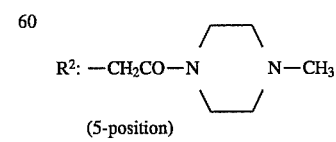

(5-position)
R³: H

TABLE 1-continued

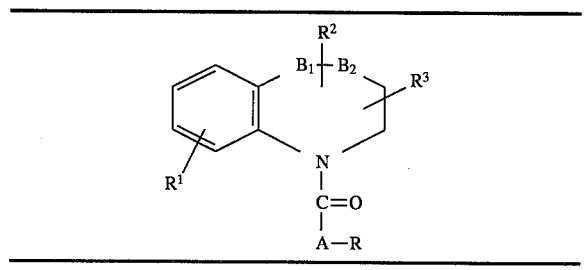

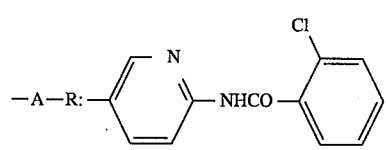

Crystalline form: White powder
Recrystallization solvent: Dichloromethane-diethyl ether
Melting point: 222–225° C.
Form: Free
Example 108

Structure:

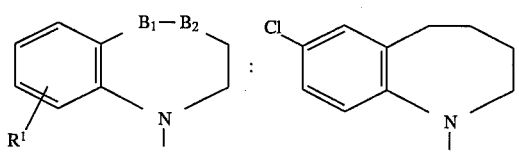

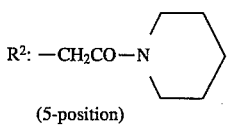

(5-position)

$R^3$: H

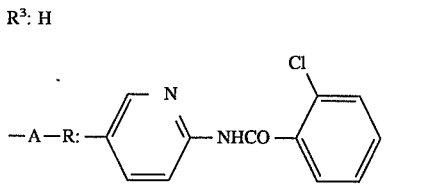

Crystalline form: White powder
Recrystallization solvent: Dichloromethane-diethyl ether
Melting Point: 229–232° C.
Form: Free
Example 109

Structure:

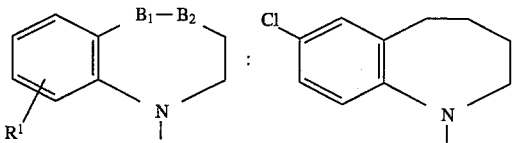

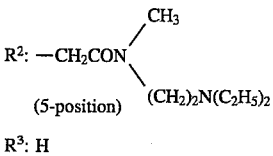

(5-position)

$R^3$: H

TABLE 1-continued

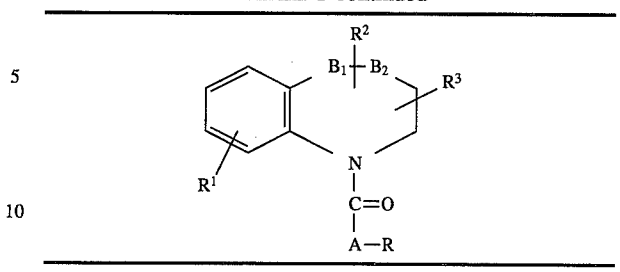

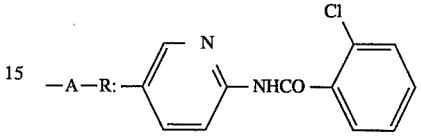

Crystalline form: White powder
Recrystallization solvent: Dichloromethane-diethyl ether
Melting point: 152–154° C.
Form: Free
Example 110

Structure:

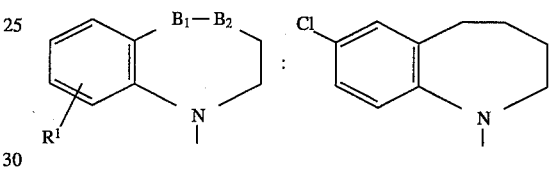

$R^2$: —CH$_2$CON(CH$_3$)$_2$ (5-position)
$R^3$: H

...NHCO...

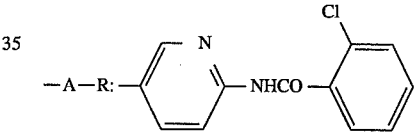

Crystalline form: White powder
Recrystallization solvent: Dichloromethane-diethyl ether
Melting point: 216–217° C.
Form: Free
Example 111

Structure:

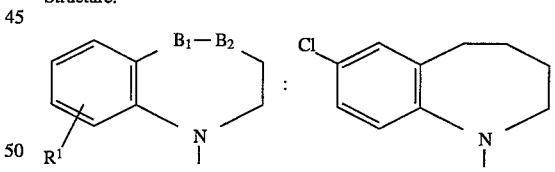

$R^2$: —CH$_2$CONHCH$_3$ (5-position)
$R^3$: H

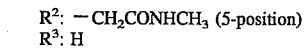

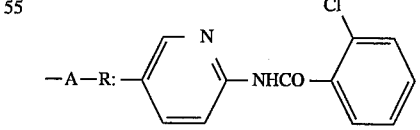

Crystalline form: White powder
NMR analysis: 56)
Form: Free
Example 112

Structure:

TABLE 1-continued

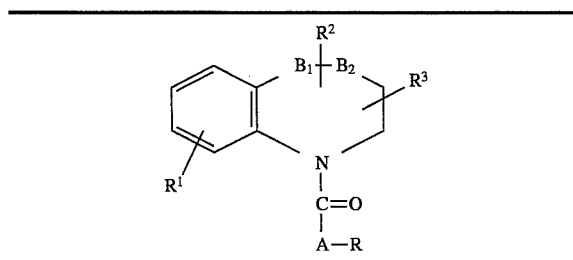

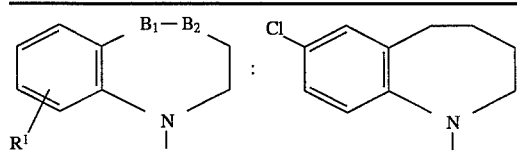

R²: —CH₂CONHC₂H₅ (5-position)
R³: H

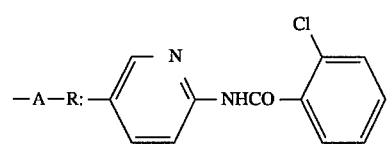

Crystalline form: White powder
Recrystallization solvent: Dichloromethane-diethyl ether
Melting point: 203–205° C.
Form: Free
Example 113

Structure:

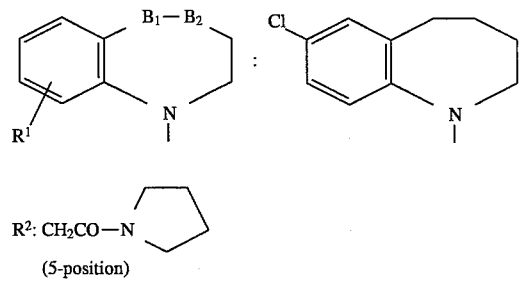

R³: H

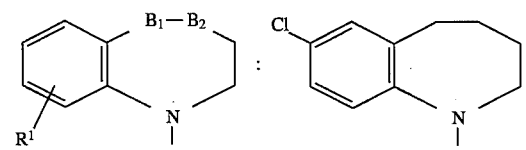

Crystalline form: White powder
Recrystallization solvent: Dichloromethane-diethyl ether
Melting point: 191–193.5° C.
Form: Free
Example 114

Structure:

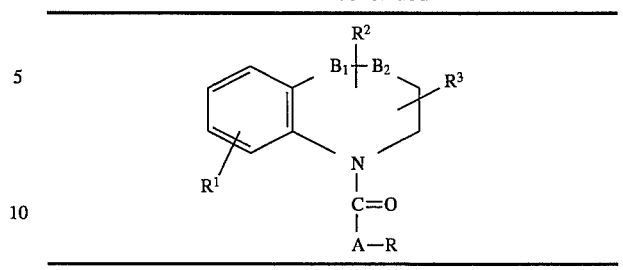

R²: CH₂CO—N⟨pyrrolidine⟩
(5-position)
R³: H

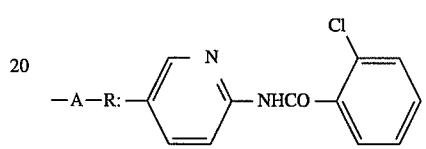

Crystalline form: White powder
Recrystallization solvent: Dichloromethane-diethyl ether
Melting Point: 191–193° C.
Form: Free
Example 115

Structure:

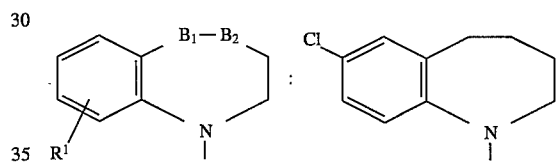

R²: —CH₂CO—N⟨piperazine⟩N—COC(CH₃)₃
(5-position)
R³: H

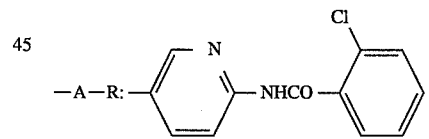

Crystalline form: Colorless amorphous
NMR analysis: 32)
Form: Free
Example 116

Structure:

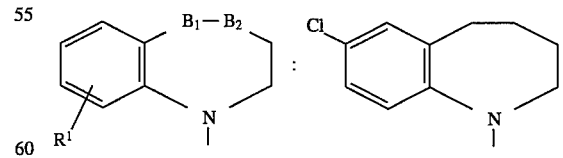

R²: —CH₂CO—N⟨piperazine⟩NH
(5-position)

TABLE 1-continued

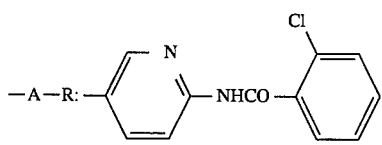

R³: H

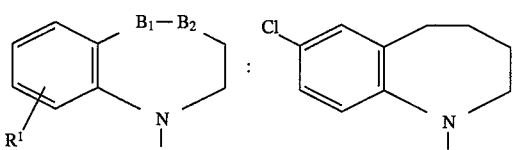

Crystalline form: White powder
Recrystallization solvent: Ethyl acetate - diethyl ether
Melting point: 157–160° C.
Form: Free
Example 117

Structure:

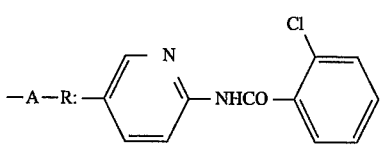

R²: —CH₂CONH₂ (5-position)
R³: H

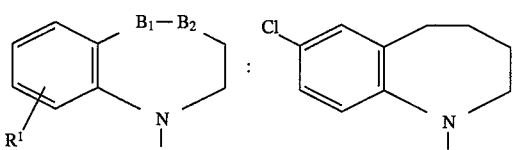

Crystalline form: White powder
Recrystallization solvent: Dichloromethane-diethyl ether
Melting Point: 242–244° C.
Form: Free
Example 118

Structure:

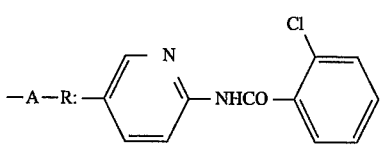

R²: —CH₂CO—N◯N—CH₃
(5-position)
R³: H

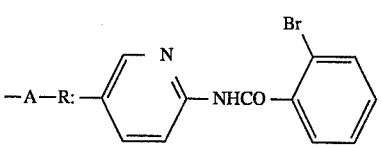

TABLE 1-continued

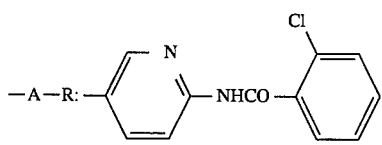

Crystalline form: White powder
Recrystallization solvent: Dichloromethane-diethyl ether
Melting point: 223–225.5° C.
Form: Free
Example 119

Structure:

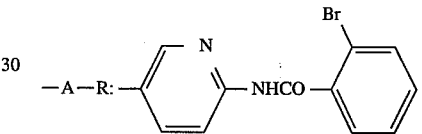

R²: —CH₂CON(CH₃)₂ (5-position)
R³: H

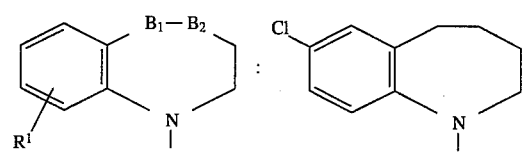

Crystalline form: White powder
Recrystallization solvent: Dichloromethane-diethyl ether
Melting point: 224–225° C.
Form: Free
Example 120

Structure:

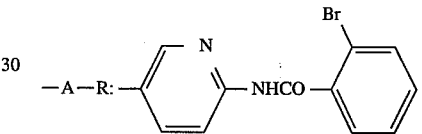

R²: —CH₂CON(CH₃)((CH₂)₂N(C₂H₅)₂)
(5-position)
R³: H

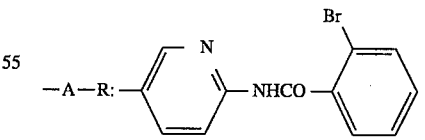

Crystalline form: White powder
Recrystallization solvent: Dichloromethane-diethyl ether
Melting Point: 145–147° C.
Form: Free
Example 121

Structure:

TABLE 1-continued

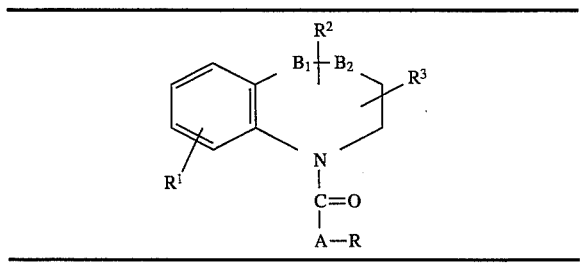

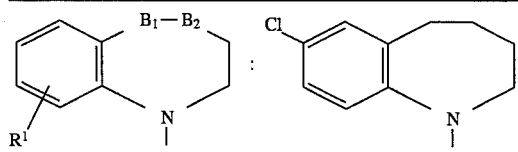

R²: —(CH₂)₂OH (5-position)
R³: H

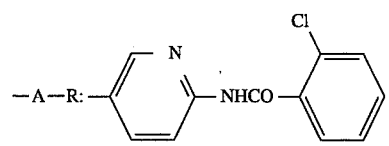

Crystalline form: White powder
Recrystallization solvent: Dichloromethane-diethyl ether
Melting point: 161–163° C.
Form: Free
Example 122

Structure:

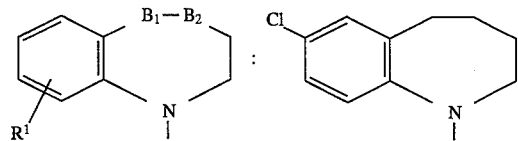

R²: —(CH₂)₂OCOCH₃ (5-position)
R³: H

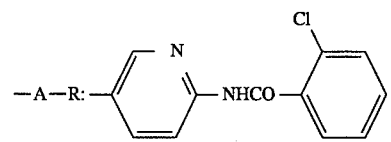

Crystalline form: White powder
Recrystallization solvent: Dichloromethane-diethyl ether
Melting point: 151–153° C.
Form: Free
Example 123

Structure:

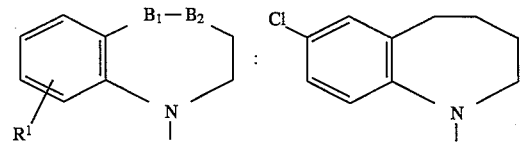

R²: —(CH₂)₂OH (5-position)
R³: H

TABLE 1-continued

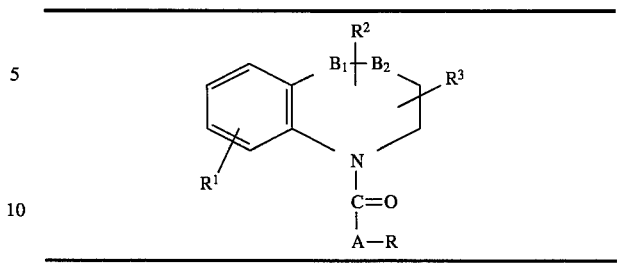

Crystalline form: White powder
Recrystallization solvent: Dichloromethane-diethyl ether
Melting Point: 168–170° C.
Form: Free
Example 124

Structure:

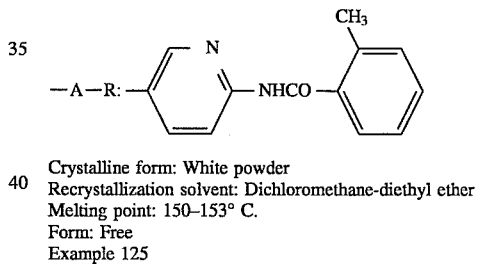

R²: —(CH₂)₂OCOCH₃ (5-position)
R³: H

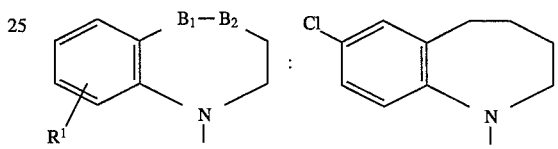

Crystalline form: White powder
Recrystallization solvent: Dichloromethane-diethyl ether
Melting point: 150–153° C.
Form: Free
Example 125

Structure:

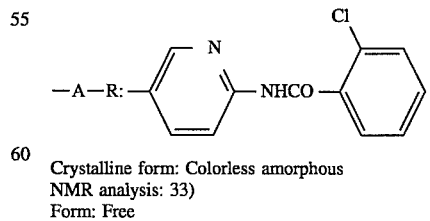

R²: —(CH₂)₂OSO₂CH₃ (5-position)
R³: H

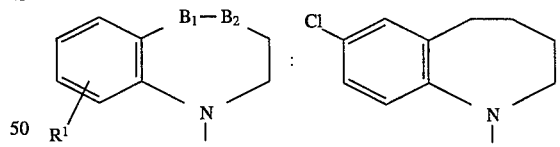

Crystalline form: Colorless amorphous
NMR analysis: 33)
Form: Free
Example 126

Structure:

TABLE 1-continued

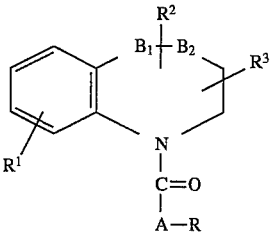

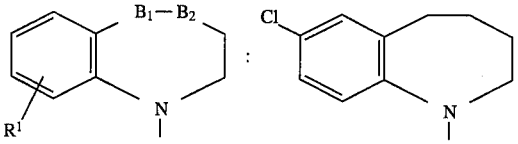

R²: —(CH₂)₂—N(pyrrolidine) (5-position)

R³: H

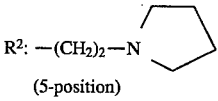

Crystalline form: Colorless amorphous
NMR analysis: 34)
Form: Free
Example 127

Structure:

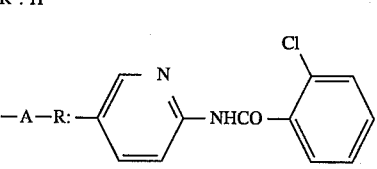

R²: —(CH₂)₂—N(morpholine)O (5-position)

R³: H

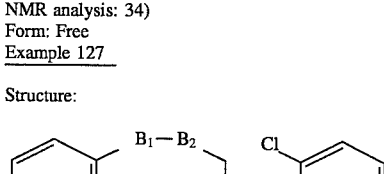

Crystalline form: Yellow amorphous
NMR analysis: 35)
Form: Free
Example 128

Structure:

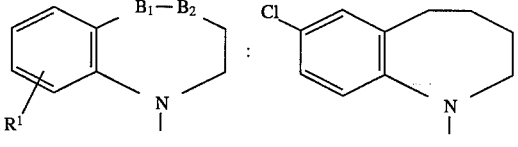

TABLE 1-continued

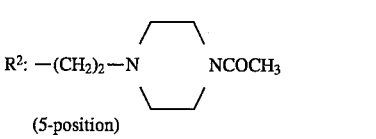

R²: —(CH₂)₂—N(piperazine)NCOCH₃ (5-position)

R³: H

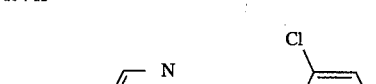

Crystalline form: Yellow amorphous
NMR analysis: 36)
Form: Free
Example 129

Structure:

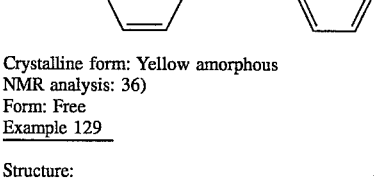

R²: —(CH₂)₂—N(imidazole)N (5-position)

R³: H

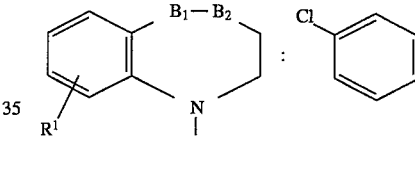

Crystalline form: White powder
Recrystallization solvent: Dichloromethane-diethyl ether
Melting Point: 201–204° C.
Form: Free
Example 130

Structure:

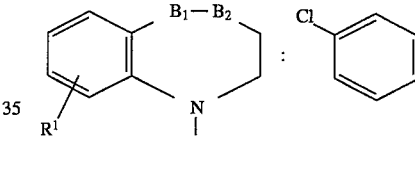

R²: —(CH₂)₂NHCH(CH₃)₂ (5-position)
R³: H

TABLE 1-continued

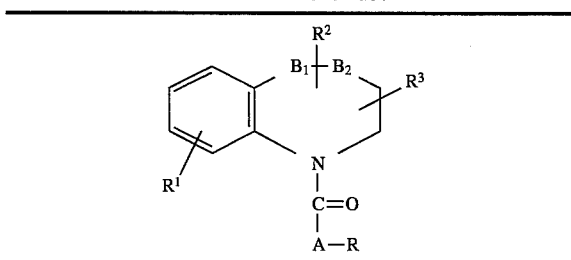

—A—R: 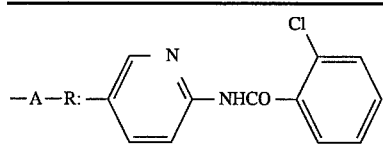

Crystalline form: Colorless amorphous
NMR analysis: 37)
Form: Free
Example 131

Structure:

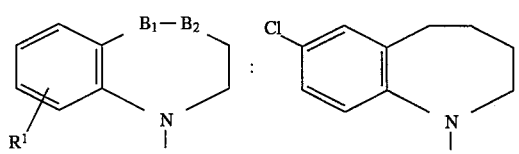

R²: 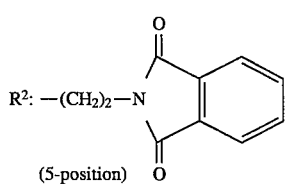

(5-position)

R³: H

—A—R: 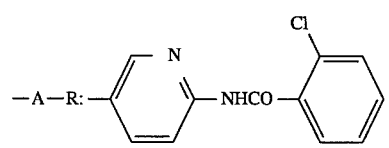

Crystalline form: Colorless amorphous
NMR analysis: 38)
Form: Free
Example 132

Structure:

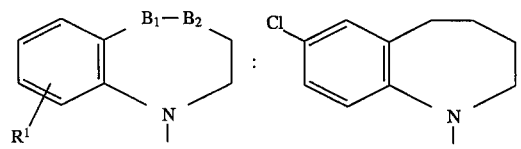

R²: —(CH₂)₂NH₂ (5-position)
R³: H

—A—R: 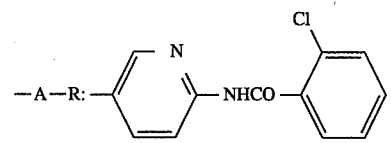

Crystalline form: Colorless amorphous

TABLE 1-continued

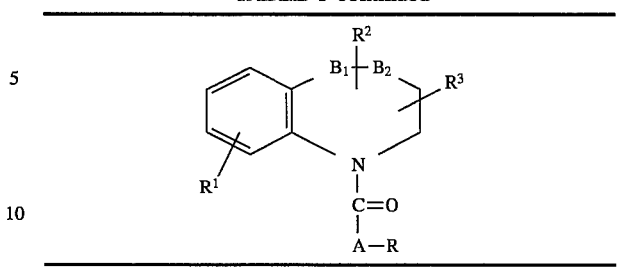

NMR analysis: 39)
Form: Free
Example 133

Structure:

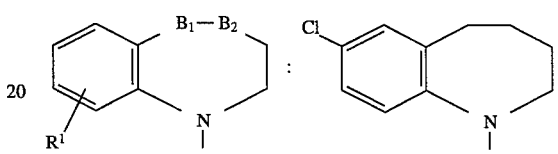

R²: —(CH₂)₂N(CH₃)₂ (5-position)
R³: H

—A—R: 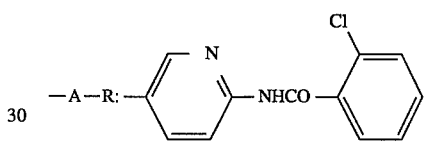

Crystalline form: Colorless amorphous
NMR analysis: 40)
Form: Free
Example 134

Structure:

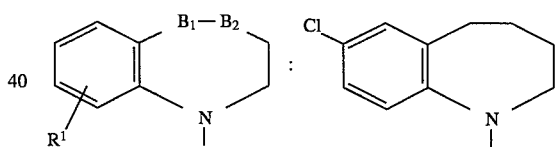

R²: —(CH₂)₂OSO₂CH₃ (5-position)
R³: H

—A—R: 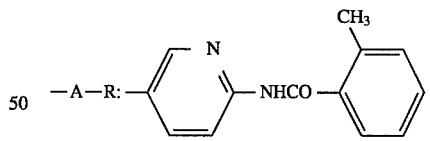

Crystalline form: Colorless amorphous
NMR analysis: 41)
Form: Free
Example 135

Structure:

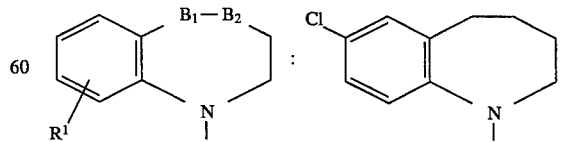

TABLE 1-continued

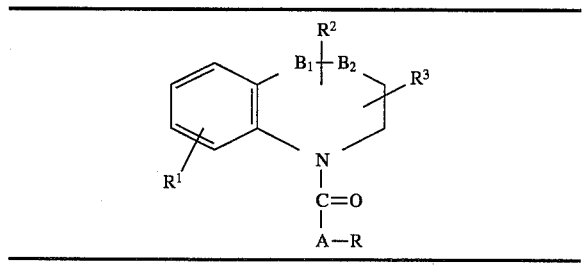

R²: —(CH₂)₂—N⟨pyrrolidine⟩
(5-position)

R³: H

—A—R: 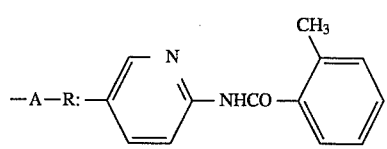

Crystalline form: Yellow amorphous
NMR analysis: 42)
Form: Free
Example 136

Structure:

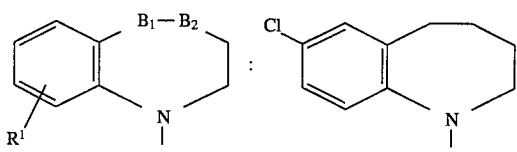

R²: —(CH₂)₂—N⟨piperazine⟩N—COCH₃
(5-position)

R³: H

—A—R: 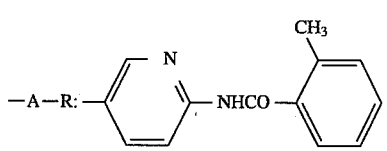

Crystalline form: Yellow amorphous
NMR analysis: 43)
Form: Free
Example 137

Structure:

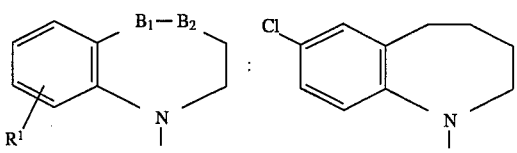

R²: —(CH₂)₂—N⟨morpholine⟩O
(5-position)

TABLE 1-continued

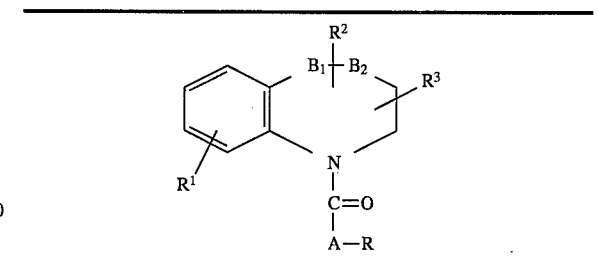

R³: H

—A—R: 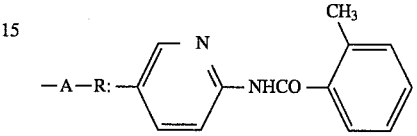

Crystalline form: Yellow amorphous
NMR analysis: 44)
Form: Free
Example 138

Structure:

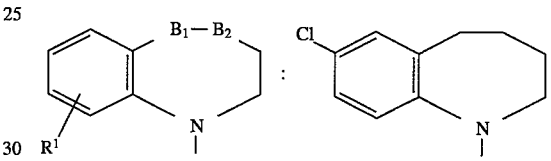

R²: —(CH₂)₂—N⟨imidazole⟩N
(5-position)

R³: H

—A—R: 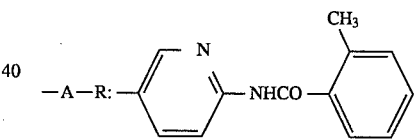

Crystalline form: White powder
Recrystallization solvent: Dichloromethane-diethyl ether
Melting Point: 192–195° C.
Form: Free
Example 139

Structure:

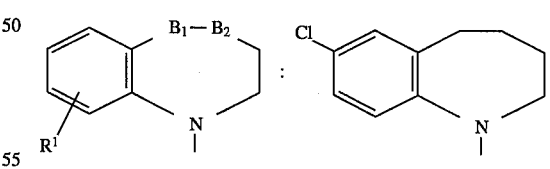

R²: —(CH₂)₂NHCH(CH₃)₂ (5-position)
R³: H

—A—R: 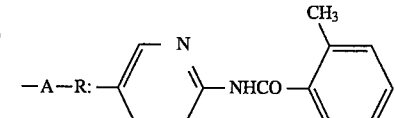

Crystalline form: Yellow amorphous

TABLE 1-continued

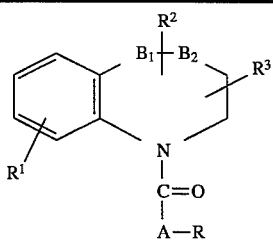

NMR analysis: 45)
Form: Free

Example 140

Structure:

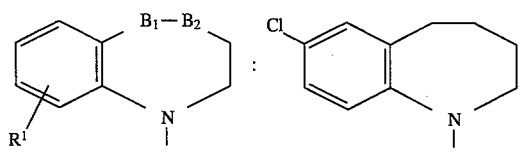

R²: —(CH₂)₂—N⟨triazole⟩ (5-position)

R³: H

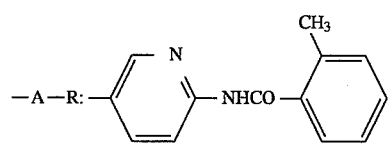

Crystalline form: White powder
Recrystallization solvent: Dichloromethane-diethyl ether
Melting point: 149–152° C.
Form: Free Example 141

Structure:

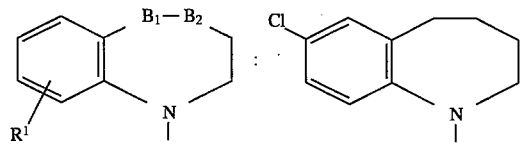

R²: —(CH₂)₂—N(phthalimido) (5-position)

R³: H

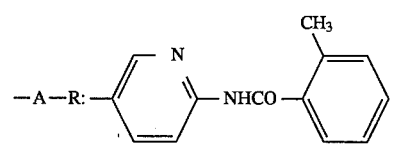

Crystalline form: Colorless amorphous
NMR analysis: 46)

TABLE 1-continued

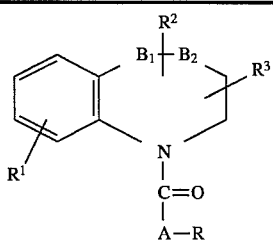

Form: Free

Example 142

Structure:

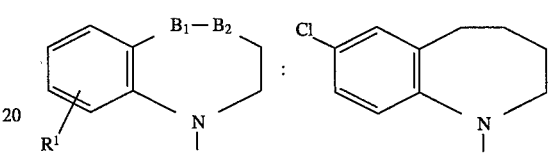

R²: —(CH₂)₂NH₂ (5-position)
R³: H

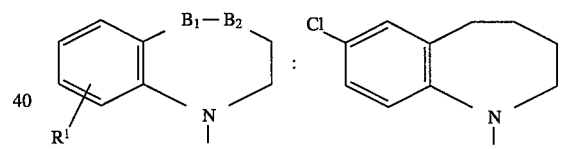

Crystalline form: Colorless amorphous
NMR analysis: 47)
Form: Free

Example 143

Structure:

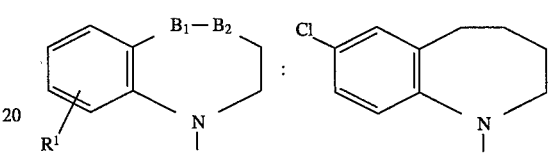

R²: —(CH₂)₂NHCOCH₃ (5-position)
R³: H

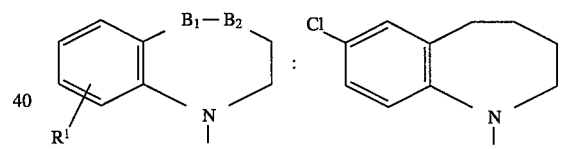

Crystalline form: White powder
NMR analysis: 48)
Form: Free

Example 144

Structure:

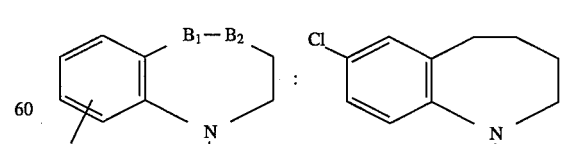

R²: =CH₂ (5-position)

TABLE 1-continued

[Structure with R², B₁, B₂, R³, R¹, N, C=O, A—R]

R³: H

—A—R: [pyridine-NHCO-(2-chlorophenyl)]

Crystalline form: Colorless amorphous
NMR analysis: 49)
Form: Free

Example 145

Structure:

[Benzazepine structure with B₁—B₂, R¹, N; and chloro-tetrahydrobenzazepine]

R²: —OH (5-position)
R³: —CH₂OH (5-position)

—A—R: [pyridine-NHCO-(2-chlorophenyl)]

Crystalline form: Colorless amorphous
NMR analysis: 50)
Form: Free

Example 146

Structure:

[Benzazepine structure with B₁—B₂, R¹, N; and chloro-tetrahydrobenzazepine]

R²: —OCH₃ (4-position)
R³: —OCH₃ (4-position)

—A—R: [pyridine-NHCO-(2-methylphenyl)]

Crystalline form: Colorless amorphous
NMR analysis: 51)
Form: Free

Example 147

Structure:

TABLE 1-continued

[Structure with R², B₁, B₂, R³, R¹, N, C=O, A—R]

[Benzazepine structure with B₁—B₂, R¹, N; and chloro-tetrahydrobenzazepine]

R²: =O (4-position)
R³: H

—A—R: [pyridine-NHCO-(2-methylphenyl)]

Crystalline form: Colorless amorphous
NMR analysis: 52)
Form: Free

Example 148

Structure:

[Benzazepine structure with B₁—B₂, R¹, N; and chloro-tetrahydrobenzazepine]

R²: —OH (4-position)
R³: H

—A—R: [pyridine-NHCO-(2-methylphenyl)]

Crystalline form: Colorless amorphous
NMR analysis: 53)
Form: Free

TABLE 2

1) $^1$H-NMR (CDCl$_3$) δ: 1.60–2.60 (4H, m), 2.46 (3H, s), 2.70–2.95 (1H, m), 3.73 (1H, s), 4.65–5.65 (2H, m), 6.57 (1H, d, J=8.1 Hz), 7.00 (1H, d, J=6.5 Hz), 7.15–8.40 (8H, m), 8.70–8.90 (1H, m)

2) $^1$H-NMR (CDCl$_3$) δ: 1.60–2.45 (4H, m), 2.41 (3H, s), 2.70–3.30 (2H, m), 4.65–5.70 (2H, m), 6.60 (1H, d, J=8.4 Hz), 7.01 (1H, dd, J=2, 8.1 Hz), 7.20– 7.50 (2H, m), 7.50–7.90 (4H, m), 8.05–8.40 (2H, m), 8.72 (1H, s)

3) $^1$H-NMR (CDCl$_3$) δ: 1.60–2.45 (4H, m), 2.41 (3H, s), 2.70–2.90 (1H, m), 3.20–3.60 (1H, m), 4.65–5.70 (2H, m), 6.59 (1H, d, J=8.2 Hz), 7.00 (1H, dd, J=2, 8.1 Hz), 7.15–7.30 (2H, m), 7.50–7.85 (4H, m), 8.05–8.40 (2H, m), 8.77 (1H, s)

4) ¹H-NMR (CDCl₃) δ: 1.60–2.90 (6H, m), 4.06 (3H, s), 4.75–5.20 (2H, m), 6.61 (1H, d, J=8 Hz), 6.95–7.25 (3H, m), 7.45–7.85 (3H, m), 8.10–8.50 (3H, m), 10.39 (1H, s)

5) ¹H-NMR (CDCl₃) δ:1.50–2.50 (4H, m), 2.60–2.90 (1H, m), 3.40–3.70 (1H, m), 4.60–5.20 (2H, m), 6.56 (1H, d, J=8.2 Hz), 7.01 (1H, dd, J=2.1, 8.3 Hz), 7.20–7.90 (6H, m), 7.90–8.20 (2H, m), 9.29 (1H, s)

6) ¹H-NMR (CDCl₃) δ:1.55–2.60 (4H, m), 2.65–2.95 (1H, m), 3.20–3.60 (1H, m), 4.70–5.25 (2H, m), 6.58 (1H, d, J=8.2 Hz), 7.01 (1H, d, J=8.1 Hz), 7.10–7.90 (6H, m), 7.90–8.40 (2H, m), 9.04 (1H, s)

7) ¹H-NMR (CDCl₃) δ:1.60–2.50 (4H, m), 2.70–2.90 (1H, m), 3.40–3.80 (1H, m), 4.70–5.20 (2H, m), 6.59 (1H, d, J=8.3 Hz), 7.00 (1H, dd, J=2.3, 8.3 Hz), 7.10–7.15 (1H, m), 7.55–7.60 (2H, m), 7.60–7.85 (2H, m), 8.00–8.40 (2H, m), 8.81 (1H, s)

8) ¹H-NMR (CDCl₃) δ:1.20–2.40 (15H, m), 2.70–3.00 (1H, m), 3.20–3.40 (1H, m), 4.70–5.20 (2H, m), 6.57 (1H, d, J=8.3 Hz), 7.00 (1H, d, J=8.4 Hz), 7.47 (1H, d, J=8.8 Hz), 7.71 (1H, s), 8.00–8.35 (3H, m)

9) ¹H-NMR (CDCl₃) δ:1.60–2.40 (4H, m), 2.30 (3H, s), 2.65–3.10 (2H, m), 3.74 (2H, s), 4.70–5.15 (2H, m), 6.54 (1H, d, J=8.3 Hz), 6.97 (1H, dd, J=2.1, 8.3 Hz), 7.20–7.30 (4H, m), 7.45–7.85 (2H, m), 7.88 (1H, s), 7.90–8.30 (2H, m)

10) ¹H-NMR (CDCl₃) δ:1.50–2.60 (3H, m), 2.45 (3H, s), 2.60–2.95 (1H, m), 3.60–4.25 (4H, m), 4.70–5.10 (1H, m), 6.54 (1H, d, J=8.3 Hz), 6.99 (1H, dd, J=2.3, 8.3 Hz), 7.10–7.70 (5H, m), 7.82 (1H, d, J=2.3 Hz), 8.10–8.30 (2H, m), 8.83 s) (1H, s)

11) ¹H-NMR (CDCl₃) δ:1,60–2.60 (8H, m), 2.29, 2.32 (3H, s), 2.50 (3H, s), 2.70–3.05 (1H, m), 3.40–3.80 (4H, m), 4.10–4.50 (2H, m), 4.55–5.20 (2H, m), 6.60–6.75 (1H, m), 7.00–7.15 (1H, m), 7.15–7.85 (6H, m), 8.10–8.40 (3H, m)

12) ¹H-NMR (CDCl₃) δ:1.50–2.60 (4H, m), 2.51 (3H, s), 2.70–3.05 (1H, m), 3.50–4.05 (4H, m), 4.50–5.15 (2H, m), 6.60–6.75 (1H, m), 7.00–7.15 (1H, m), 7.20–7.85 (6H, m), 8.10–8.40 (3H, m)

13) ¹H-NMR (CDCl₃) δ:1.50–3.00 (13H, m), 2.50 (3H, s), 3.40–3.85 (2H, m), 4.45–5.15 (2H, m), 6.60 (1H, d, J=8.1 Hz), 7.00–7.10 (1H, m), 7.20–7.90 (6H, m), 8.05–8.60 (3H, m)

14) ¹H-NMR (CDCl₃) δ:1.60–2.70 (6H, m), 2.50 (3H, s), 2.70–3.00 (1H, m), 3.00–3.20 (1H, m), 3.40–3.80 (4H, m), 4.50–5.10 (2H, m), 5.95–6.15 (1H, m), 6.65–6.80 (1H, m), 7.00–7.20 (1H, m), 7.20–7.80 (6H, m), 8.05–8.50 (3H, m)

15) ¹H-NMR (CDCl₃) δ:1.20–3.95 (16H, m), 2.34 (3H, s), 2.50 (3H, s), 4.40–5.15 (1H, m), 6.61 (1H, d, J=8.3 Hz), 6.97 (1H, dd, J=2.1,8.3 Hz), 7.03 (1H, s), 7.20–7.40 (3H, m), 7.48 (1H, d, J=7.6 Hz), 7.83 (1H, dd, J=2.1, 8.8 Hz), 8.20 (1H, d, J=8.8 Hz), 8.31 (1H, s), 8.38 (1H, d, J=2.1 Hz)

16) ¹H-NMR (CDCl₃) δ:2.43 (3H, s), 2.49 (3H, s), 3.04 (3H, s), 3.70 (1H, d, J=14 Hz), 4.02 (1H, d, J=14 Hz), 4.85–5.10 (1H, m), 6.61 (1H, d, J=8.3 Hz), 7.03 (1H, dd, J=2.4, 8.3 Hz), 7.20–7.60 (6H, m), 8.01 (1H, d, J=1.7 Hz), 8.12 (1H, d, J=8.7 Hz), 8.67 (1H, s)

17) ¹H-NMR (CDCl₃) δ:1.75–2.20 (2H, m), 2.80–3.30 (2H, m), 2.96 (3H, s), 3.40–3.65 (1H, m), 4.45–4.70 (1H, m), 6.52 (1H, d, J=8.2 Hz), 6.62 (1H, dd, J=1.8, 8.2 Hz), 6.90 (1H, d, J=1.9 Hz), 7.30–7.55 (4H, m), 7.66 (1H, d, J=7.1 Hz), 7.95 (1H, d, J=1.6 Hz), 8.16 (1H, d, J=8.6 Hz), 9.14 (1H, s)

18) ¹H-NMR (CDCl₃) δ:1.20–2.60 (10H, m), 2.44 (3H, s), 3.15–3.65 (2H, m), 4.00–5.00 (1H, m), 6.50 (2H, s), 6.90–7.50 (6H, m), 7.67 (1H, s), 8.73 (1H, s)

19) ¹H-NMR (CDCl₃) δ: 1.85–2.20 (2H, m), 2.30–3.30 (3H, m), 2.50 (3H, s), 4.75–5.15 (1H, m), 5.20–5.35 (2H, m), 6.61 (1H, d, J=8.3 Hz), 7.01 (1H, dd, J=2.5, 8.4 Hz), 7.20–7.60 (6H, m), 8.06 (1H, d, J=2 Hz), 8.19 (1H, d, J=8.7 Hz), 8.34 (1H, s)

20) ¹H-NMR (CDCl₃) δ:2.00–2.40 (2H, m), 2.30 (3H, s), 2.85 (2H, t, J=6.2 Hz), 3.74 (2H, s), 3.40–4.60 (2H, m), 6.66 (1H, d, J=8.4 Hz), 7.15–7.30 (5H, m), 7.52 (1H, dd, J=2.4, 8.6 Hz), 7.74 (1H, s), 7.82 (1H, d, J=2.5 Hz), 8.05–8.15 (2H, m)

21) ¹H-NMR (CDCl₃) δ:1.60–2.60 (4H, m), 2.51 (3H, s), 3.70–3.80 (3H, m), 4.10–4.50 (2H, m), 4.55–5.20 (2H, m), 6.60–6.70 (1H, m), 7.00–7.15 (1H, m), 7.20–7.90 (6H, m), 8.10–8.45 (3H, m)

22) ¹H-NMR (CDCl₃) δ:1.50–2.60 (4H, m), 2.50 (3H, s), 2.70–3.20 (1H, m), 2.93, 3.13 (3H, s), 3.70–4.05 (2H, m), 4.20–5.20 (4H, m), 6.64 (1H, d, J=8.1 Hz), 7.00–7.10 (1H, m), 7.20–7.85 (6H, m), 8.05–8.40 (3H, m)

23) ¹H-NMR (CDCl₃) δ:1.45–2.55 (4H, m), 2.51 (3H, s), 2.60–2.95 (1H, m), 3.70–4.20 (2H, m), 4.50–5.15 (2H, m), 6.58 (1H, d, J=8.2 Hz), 6.99 (1H, d J=8.5 Hz), 7.20–8.50 (15H, m)

24) ¹H-NMR (CDCl₃) δ: 1.50–2.60 (4H, m), 2.50 (3H, s), 2.65–3.20 (3H, m), 3.40–3.80 (2H, m), 4.45–5.15 (2H, m), 6.62 (1H, d, J=8.1 Hz), 7.04 (1H,d, J=8.1 Hz), 7.15–7.85 (6H, m), 8.10–8.50 (3H, m)

25) ¹H-NMR (CDCl₃) δ:1.60–2.50 (3H, m), 2.65–2.90 (1H, m), 3.20–3.35 (1H, m), 3.81 (3H, s), 4.70–5.15 (2H, m), 6.57 (1H, d, J=8.3 Hz), 7.01 (1H, d, J=8.2 Hz), 7.20–8.25 (8H, m), 8.85–9.15 (1H, m)

26) ¹H-NMR (CDCl₃) δ:1.40–1.70 (1H, m), 1.85–2.20 (3H, m), 2.70–3.15 (3H, m), 3.06 (3H, s), 4.45–4.55 (2H, m), 4.60–4.70 (2H, m), 4.95–5.15 (1H, m), 6.62 (1H, d, J=8.2 Hz), 6.97 (2H, t, J=8.2 Hz), 7.17 (1H, t, J=7.2 Hz), 7.28 (1H, s), 7.45–7.60 (2H, m), 8.09 (1H, s), 8.15–8.30 (2H, m), 10.23 (1H, s)

27) ¹H-NMR (DMSO-d₆) δ:1.18 (6H, d, J=6.4 Hz), 1.30–1.60 (1H, m), 1.70–2.15 (3H, m), 2.10–3.20 (3H, m), 3.20–3.55 (3H, m), 4.40–4.55 (2H, m), 4.75–4.95 (1H, m), 6.89 (1H, d, J= 8.4 Hz), 7.05–7.25 (3H, m), 7.45–7.80 (4H, m), 8.01 (1H, s), 8.11 (1H, d, J=8.6 Hz), 9.27 (2H, brs), 10.71 (1H, s)

28) ¹H-NMR (CDCl₃) δ:1.30–1.65 (1H, m), 1.90–2.20 (3H, m), 2.60–3.10 (3H, m), 4.10–4.30 (2H, m), 4.40–4.60 (2H, m), 4.90–5.10 (1H, m), 6.60 (1H, d, J=8 Hz), 6.90–7.00 (1H, m), 7.00–7.15 (2H, m), 7.25–7.30 (1H, m), 7.40–7.55 (2H, m), 7.60–7.85 (4H, m), 7.97 (1H, s), 8.10–8.20 (2H, m), 10.05 (1H, s)

29) ¹-NMR (CDCl₃) δ: 1.35–2.20 (4H, m), 2.60–3.40 (5H, m), 4.15–4.30 (2H, m), 4.90–5.10 (1H, m), 6.61 (1H, d, J=8.2 Hz), 6.90–7.30 (4H, m), 7.40–7.55 (2H, m), 8.15–8.25 (3H, m), 10.81 (1H, s)

30) ¹H-NMR (DMSO-d₆) δ:1.30–1.60 (1H, m), 1.80–2.15 (3H, m), 2.79 (6H, s), 2.60–3.20 (3H, m), 3.55 (2H, s), 4.53 (2H, s), 4.75–4.90 (1H, m), 5.60 (1H, brs), 6.87 (1H, d, J=8.4 Hz), 7.05–7.25 (3H, m), 7.45–7.75 (4H, m), 8.05–8.15 (2H, m), 10.69 (1H, s), 10.90 (1H, brs)

31) ¹H-NMR (CDCl₃) δ: 1.30–2.15 (4H, m), 2.49 (3H, s), 2.62 (6H, s), 2.30–3.90 (8H, m), 4.35–4.55, 5.10–5.30 (1H, m), 6.60 (1H, d, J=8.3 Hz), 6.90–7.05 (1H, m), 7.20–7.80 (7H, m), 8.15 (1H, d, J=8.5 Hz), 8.30–8.40 (2H, m)

32) ¹H-NMR (CDCl₃) δ:1.30–2.10 (4H, m), 1.49 (9H, s), 2.60–3.95 (12H, m), 4.40–4.60, 5.05–5.20 (1H, m), 6.58 (1H, d, J=8.2 Hz), 6.90–7.05 (2H, m), 7.30–7.50 (3H, m), 7.60–7.90 (2H, m), 8.00–8.25 (1H, m), 8.35 (1H, d, J=2 Hz), 8.75 (1H, s)

33) ¹H-NMR (CDCl₃) δ: 1.30–2.50 (6H, m), 2.55–3.45 (2H, m), 3.04 (3H, s), 4.20–4.60, 5.10–5.25 (3H, m), 6.64

(1H, d, J=8.3 Hz), 7.03 (1H, d, J=8.2 Hz), 7.15–7.50 (5H, m), 7.56 (1H, d, J=8.6 Hz), 7.72 (1H, d, J=6.2 Hz), 8.09 (1H, s), 8.21 (1H, d, J=8.7 Hz), 8.74 (1H, s)

34) $^1$H-NMR (CDCl$_3$) δ:1.30–2.80 (14H, m), 3.05–3.40 (2H, m), 4.25–4.45, 5.05–5.25 (1H, m), 6.60 (1H, d, J=8.2 Hz), 6.90–7.05 (1H, m), 7.25–7.60 (5H, m), 7.72 (1H, d, J=6.4 Hz), 8.17 (1H, d, J=8.1 Hz), 8.70 (1H, s)

35) $^1$H-NMR (CDCl$_3$) δ:1.30–2.80 (12H, m), 3.05–3.40 (2H, m), 3.60–3.90 (4H, m), 4.30–4.60, 5.05–5.25 (1H, m), 6.61 (1H, d, J=8.2 Hz), 6.90–7.10 (1H, m), 7.20–7.70 (5H, m), 7.72 (1H, d, J=6.2 Hz), 8.10–8.30 (2H, m), 8.69 (1H, s)

36) $^1$H-NMR (CDCl$_3$) δ:1.25–2.30 (6H, m), 2.07 (3H, s), 2.30–2.80 (6H, m), 3.00–3.70 (6H, m), 4.30–4.50, 5.10–5.25 (1H, m), 6.55–6.64 (1H, m), 6.90–7.05 (1H, m), 7.20–7.30 (1H, m), 7.40–7.50 (3H, m), 7.55–7.65 (1H, m), 7.73 (1H, d, J=6.3 Hz), 8.10–8.25 (2H, m), 8.68 (1H, s)

37) $^1$H-NMR (CDCl$_3$) δ:1.04–1.12 (6H, m), 1.20–2.30 (6H, m), 2.50–3.00 (3H, m), 3.00–3.40 (2H, m), 4.30–4.50, 5.10–5.25 (1H, m), 6.50–6.65 (1H, m), 6.90–7.15 (1H, m), 7.25–7.65 (5H, m), 7.73 (1H, d, J=7.2 Hz), 8.17 (1H, d, J=8.9 Hz), 8.70 (1H, brs)

38) $^1$H-NMR (CDCl$_3$) δ: 1.25–2.50 (6H, m), 2.60–3.40 (2H, m), 3.70–4.00 (2H, m), 4.30–4.50, 5.10–5.30 (1H, m), 6.62 (1H, d, J=8.5 Hz), 6.90–7.15 (1H, m), 7.25–7.60 (5H, m), 7.65–7.90 (5H, m), 8.00–8.30 (2H, m), 8.72 (1H, s)

39) $^1$H-NMR (CDCl$_3$) δ:1.20–2.30 (6H, m), 2.60–3.40 (4H, m), 4.25–4.45, 5.05–5.25 (1H, m), 6.56–6.65 (1H, m), 6.90–7.05 (1H, m), 7.20–7.60 (5H, m), 7.69 (1H, d, J=6.4 Hz), 8.05–8.25 (2H, m), 9.02 (1H, brs)

40) $^1$H-NMR (CDCl$_3$) δ:1.20–2.80 (8H, m), 2.22, 2.26 (6H, s), 3.05–3.40 (2H, m), 4.25–4.44, 5.10–5.20 (1H, m), 6.50–6.65 (1H, m), 6.90–7.05 (1H, m), 7.20–7.30 (1H, m), 7.30–7.60 (4H, m), 7.71 (1H, d, J=6.3 Hz), 8.15–8.20 (2H, m), 8.73 (1H, s)

41) $^1$H-NMR (CDCl$_3$) δ: 1.20–2.80 (6H, m), 2.50 (3H, s), 3.03 (3H, s), 3.10–3.50 (2H, m), 4.20–4.55, 5.10–5.30 (3H, m), 6.65 (1H, d, J=8.4 Hz), 7.03 (1H, d, J=8.4 Hz), 7.20–7.65 (6H, m), 8.09 (1H, s), 8.20–8.25 (2H, m)

42) $^1$H-NMR (CDCl$_3$) δ:1.20–2.30 (10H, m), 2.50 (3H, s), 2.30–2.80 (6H, m), 3.10–3.40 (2H, m), 4.20–4.45, 5.05–5.25 (1H, m), 6.50–6.65 (1H, m), 6.90–7.05 (1H,), 7.20–7.60 (6H, m), 8.10–8.20 (2H, m), 8.35 (1H, s)

43) $^1$H-NMR (CDCl$_3$) δ: 1.20–2.30 (6H, m), 2.07 (3H, s), 2.50 (3H, s), 2.30–2.80 (6H, m), 3.00–3.70 (6H, m), 4.25–4.45, 5.05–5.25 (1H, m), 6.55–6.65 (1H, m), 6.95–7.05 (1H, m), 7.20–7.65 (6H, m), 8.05–8.30 (3H, m)

44) $^1$H-NMR (CDCl$_3$) δ:1.20–2.70 (12H, m), 2.50 (3H, s), 3.00–3.40 (2H, m), 3.65–3.75 (4H, m), 4.30–4.50, 5.10–5.30 (1H, m), 6.55–6.65 (1H, m), 6.95–7.05 (1H, m), 7.25–7.60 (5H, m), 8.11–8.30 (3H, m)

45) $^1$H-NMR (CDCl$_3$) δ:0.95–1.05 (6H, m), 1.10–2.90 (9H, m), 2.42 (3H, s), 2.90–3.30 (2H, m), 4.20–4.40, 5.00–5.20 (1H, m), 6.53 (1H, d, J=8.1 Hz), 6.85–7.00 (1H, m), 7.10–7.45 (6H, m), 8.00–8.15 (2H, m), 8.37 (1H, s)

46) $^1$H-NMR (CDCl$_3$) δ:1.20–2.70 (6H, m), 2.50 (3H, s), 2.80–3.40 (2H, m), 3.70–3.95 (2H, m), 4.30–4.50, 5.10–5.30 (1H, m), 6.63 (1H, d, J=8.6 Hz), 7.00–7.05 (1H, m), 7.20–7.60 (5H, m), 7.65–7.90 (5H, m), 8.00–8.35 (3H, m)

47) $^1$H-NMR (CDCl$_3$) δ: 1.20–2.30 (6H, m), 2.50 (3H, s), 2.55–3.40 (4H, m), 4.25–4.45, 5.10–5.25 (1H, m), 6.50–6.65 (1H, m), 6.95–7.05 (1H, m), 7.20–7.60 (6H, m), 8.05–8.25 (2H, m), 8.47 (1H, s)

48) $^1$H-NMR (CDCl$_3$)δ:1.20–2.30 (6H, m), 1.99 (3H, s), 2.50 (3H, s), 2.80–3.60 (6H, m), 4.30–4.50, 5.05–5.25 (1H, m), 5.45–5.80 (1H, m), 6.55–6.65 (1H, m), 6.95–7.05 (1H, m), 7.20–7.60 (6H, m), 8.00–8.30 (3H, m)

49) $^1$H-NMR (CDCl$_3$) δ:1.80–2.25 (2H, m), 2.30–3.20 (3H, m), 4.70–5.20 (1H, m), 5.26 (1H, s), 5.33 (1H, s), 6.61 (1H, d, J=8.4 Hz), 7.01 (1H dd, J=1.9, 8.4 Hz), 7.30–7.60 (5H, m), 7.71 (1H, dd, J=1.7, 6.3 Hz), 8.06 (1H, d, J=1.7 Hz), 8.18 (1H, d, J=8.7 Hz), 8.75 (1H, s)

50) $^1$H-NMR (CDCl$_3$) δ:1.50–2.25 (4H, m), 2.70–3.00 (1H, m), 3.40–4.20 (4H, m), 4.70–5.10 (1H, m), 6.54 (1H, d, J=8.3 Hz), 6.99 (1H, dd, J=2.4, 8.3 Hz), 7.25–7.40 (3H, m), 7.55–7.65 (2H, m), 7.84 (1H, d, J=2.4 Hz), 8.10–8.20 (2H, m), 9.07 (1H, s)

51) $^1$H-NMR (CDCl$_3$) δ:2.00–2.15 (2H, m), 2.49 (3H, s), 3.13 (2H, s), 3.20 (3H, s), 3.31 (3H, s), 3.10–3.35 (1H, m), 4.70–4.85 (1H, m), 6.58 (1H, d, J=8.4 Hz), 7.00 (1H, dd, J=2.3, 8.3 Hz), 7.20–7.55 (6H, m), 7.95 (1H, d, J=1.8 Hz), 8.20 (1H, d, J=8.7 Hz), 8.55 (1H, s)

52) $^1$H-NMR (CDCl$_3$) δ:2.50 (3H, s), 2.65–3.00 (2H, m), 3.40–3.70 (2H, m), 4.00–4.30 (1H, m), 4.65–5.00 (1H, m), 6.73 (1H, d, J=8.4 Hz), 7.11 (1H, dd, J=2.4, 8.4 Hz), 7.20–7.65 (6H, m), 8.07 (1H, d, J=1.7 Hz), 8.24 (1H, d, J=8.7 Hz), 8.50 (1H, s)

53) $^1$H-NMR (CDCl$_3$) δ:1.80–2.30 (2H, m), 2.49 (3H, s), 2.75–3.40 (3H, m), 3.75–4.00, 4.30–4.45 (1H, m), 4.70–5.10 (1H, m), 6.55–6.65 (1H, m), 7.01 (1H, d, J=8.3 Hz), 7.20–7.60 (6H, m), 8.01 (1H, s), 8.20 (1H, d, J=8.6 Hz), 8.50 (1H, s)

54) $^1$H-NMR (CDCl$_3$) δ:1.55–2.50 (4H, m), 2.51 (3H, s), 2.65–3.00 (1H, m), 4.00–4.25 (2H, m), 4.45–4.80 (2H, m), 5.00–5.45 (2H, m), 5.75–6.15 (1H, m), 6.61 (1H, d, J=8.1 Hz), 7.03 (1H, d, J=8.2 Hz), 7.20–7.80 (6H, m), 8.05–8.40 (3H, m)

55) $^1$H-NMR (CDCl$_3$) δ:0.35–0.65 (4H, m), 1.35–2.40 (6H, m), 2.50 (3H, s), 2.60–3.30 (1H, m), 3.90–5.20 (2H, m), 6.62 (1H, d, J=8.2 Hz), 6.95–7.10 (1H, m), 7.20–7.85 (6H, m), 8.15–8.40 (3H, m)

56) $^1$H-NMR (CDCl$_3$) δ:1.25–2.20 (4H, m), 2.40–3.00 (5H, m), 3.10–3.35 (1H, m), 3.50–3.90 (1H, m), 4.40–4.55, 5.00–5.15 (1H, m), 5.90–6.10 (1H, m), 6.59 (1H, d, J=8.3 Hz), 6.98 (1H, d, J=8.3 Hz), 7.12 (1H, d, J=2.1 Hz), 7.30–7.60 (3H, m), 7.60–7.75 (2H, m), 8.10–8.30 (2H, m), 8.94 (1H, s)

EXAMPLE 149

To a suspension of 7-chloro-5-hydroxy-1-[6-(2-methoxycarbonyl-benzoylamino)nicotinoyl]-2,3,4,5-tetrahydro-1H-benzazepine (0.3 g) in methanol (4 ml) is added 5% aqueous sodium hydroxide solution (1.5 ml), and the mixture is stirred at room temperature for one hour. To the reaction solution are added water and diluted aqueous hydrochloric acid solution in order to make the mixture weak acidic. The mixture is extracted with dichloromethane, and the extract is washed with water, dried over magnesium sulfate and evaporated under reduced pressure to remove the solvent. The residue is recrystallized from dichloromethane-methanol to give 7-chloro-5-hydroxy- 1-[6-(2-carboxybenzoylamino)nicotinoyl]- 2,3,4,5-tetrahydro-1H-benzazepine (150 mg) as white powder.

M.p. 153°–155° C.

Using the suitable starting compounds, there are obtained the compounds of Examples 83, 85 and 86 in the same manner as in Example 149.

EXAMPLE 150

To a solution of 7-chloro-1-{6-[2-(3-ethoxycarbonylpropoxy)benzoyl-amino]nicotinoyl}- 2,3,4,5-tetrahydro-1H- benzazepine (2.5 g)in ethylene glycol dimethyl ether (70 ml)is added sodium trimethoxyborohydride (3.78 g), and the mixture is refluxed for 3 hours. The reaction solution is gradually poured into diluted hydrochloric acid, and the mixture is extracted with ethyl acetate. The extract is washed with water, dried over magnesium sulfate, and evaporated under reduced pressure to remove the solvent. The residue is purified by silica gel column chromatography, and recrystallized from dichloromethane-diethyl ether to give 7-chloro-1-{6-[2-( 4-hydroxybutoxy)benzoylamino]nicotinoyl}-2,3,4,5-tetrahydro- 1H-benzazepine (1.12 g) as white powder.

M.p. 157°–158.5° C.

Using the suitable starting compounds, there is obtained the compound of Example 83 in the same manner as in Example 150.

EXAMPLE 151

To a solution of 7-chloro-1-[6-( 2-carboxymethoxybenzoylamino)-nicotinoyl]-2,3,4,5-tetrahydro- 1H-benzazepine (0.4 g) in dichloromethane (10 ml) is added with stirring N,N-bis(2-oxo-3-oxazolidinyl)phosphinic chloride (0.25 g) under ice-cooling, and the mixture is stirred at room temperature for 15 minutes. Subsequently, to the reaction mixture is added N-methylpiperazine (0.11 ml), and thereto is added triethylamine (0.23 ml). The mixture is stirred at room temperature overnight, and thereto is added water. The mixture is extracted with dichloromethane, and the extract is washed successively with diluted aqueous sodium hydroxide solution and water, dried over magnesium sulfate, and evaporated under reduced pressure to remove the solvent. The residue is purified by silica gel column chromatography, and recrystallized from dichloromethane-diethyl ether to give 7-chloro-1-{6-[2-( 4-methyl-1-piperazinyl)-carbonyl methoxybenzoylamino]nicotinoyl}- 2,3,4,5-tetrahydro-1H-benzazepine (390 mg) as white powder.

M.p. 111°–114° C.

Using the suitable starting compounds, there are obtained the compounds of Examples 89 and 97 in the same manner as in Example 151.

EXAMPLE 152

To a solution of 7-chloro-1-{6-[2-( 2-hydroxyethoxy)benzoylamino]-nicotinoyl}-2,3,4,5-tetrahydro- 1H-benzazepine (0.5 g )in pyridine (10 ml) is added with stirring methanesulfonyl chloride (0.1 ml) under ice-cooling, and the mixture is stirred at room temperature for 2 hours. To the reaction solution is added water, and the precipitated crystals are collected by filtration, and dissolved in dichloromethane. The mixture is washed successively with diluted hydrochloric acid and water, dried over magnesium sulfate and evaporated under reduced pressure. The residue is crystallized from diethyl ether to give 7-chloro-1-{ 6-[2-( 2-methanesulfonyloxyethoxy)benzoylamino]nicotinoyl}- 2,3,4,5-tetrahydro-1H-benzazepine (0.59 g) as white powder.

$^1$H-NMR (CDCl$_3$) δ:1.40–1.70 (1H, m), 1.85–2.20 (3H, m), 2.70– 3.15 (3H, m), 3.06 (3H, s), 4.45–4.55 (2H, m), 4.60–4.70 (2H, m), 4.95–5.15 (1H, m), 6.62 (1H, d, J=8.2 Hz), 6.97 (2H, t, J=8.2 Hz), 7.17 (1H, t, J=7.2 Hz), 7.28 (1H, s), 7.45–7.60 (2H, m), 8.09 (1H, s), 8.15–8.30 (2H, m), 10.23 (1H,s)

EXAMPLE 153

To a solution of 7-chloro-1-{6-[2-( 2-methanesulfonyloxyethoxy)-benzoylamino]nicotinoyl}- 2,3,4,5-tetrahydro-1H-benzazepine (0.6 g) in dimethylformamide (5 ml) are added sodium iodide (0.22 g), potassium carbonate (0.23 g) and 4-acetylaminopiperidine (0.2 g), and the mixture is heated with stirring at 110° C. for 2 hours. The mixture is cooled, and thereto is added water, and the mixture is extracted with dichloromethane. The extract is washed with water, dried over magnesium sulfate, and evaporated under reduced pressure to remove the solvent. The residue is purified by silica gel column chromatography to give 7-chloro-1-{6-[ 2-(4-acetylamino-1-piperidinyl)-ethoxy] benzoylamino]nicotinoyl}- 2,3,4,5-tetrahydro-1H-benzazepine (0.3 g) as white powder.

M.p. 159°–162° C.

Using the suitable starting compounds, there are obtained the compounds of Examples 91, 93, 95 and 96 in the same manner as in Example 153.

EXAMPLE 154

To a solution of 7-chloro-1-{6-[2-( 2-methanesulfonyloxyethoxy)-benzoylamino]nicotinoyl}- 2,3,4,5-tetrahydro-1H-benzazepine (0.75 g) in dimethylformamide (10 ml) is added potassium phthalimide (0.26 g), and the mixture is stirred at 110° C. for one hour. The mixture is poured into ice-water, and extracted with dichloromethane. The extract is washed with water, dried over magnesium sulfate, and evaporated under reduced pressure. The residue is purified by silica gel column chromatography to give 7-chloro-1-[6-(6,7-benzo-1-oxo-4-azepin-5-on- 4-yl)nicotinoyl]-2,3, 4,5-tetrahydro-1H-benzazepine (0.23 g, Compound A) and 7-chloro-1-{6-[ 2-(2-phthalimido-ethoxy)benzoylamino] nicotinoyl}- 2,3,4,5-tetrahydro-1H-benzazepine (0.25 g, Compound B), separately.

Compound A

White powder

M.p. 176°–179° C. (recrystallized from ethyl acetate)

Compound B

White powder $^1$H-NMR (CDCl$_3$) δ:1.30–1.65 (1H, m), 1.90–2.20 (3H, m), 2.60– 3.10 (3H, m), 4.10–4.30 (2H, m), 4.40–4.60 (2H, m), 4.90–5.10 (1H, m), 6.60 (1H, d, J=8 Hz), 6.90–7.00 (2H, m), 7.00–7.15 (2H, m), 7.25–7.30 (1H, m), 7.40– 7.55 (2H, m), 7.60–7.85 (4H, m), 7.97 (1H, s), 8.10–8.20 (2H, m), 10.05 (1H, s)

EXAMPLE 155

To a solution of 7-chloro-1-{6-[2-( 2-phthalimidoethoxy)benzoyl-amino]nicotinoyl}- 2,3,4,5-tetrahydro-1H-benzazepine (0.25 g)in ethanol (5 ml) is added hydrazine monohydrate (0.03 ml), and the mixture is refluxed for one hour, and cooled. To the mixture is added water, and the mixture is made acidic with diluted hydrochloric acid, and washed with diethyl ether. The aqueous layer is made basic with aqueous sodium hydroxide solution, and extracted with dichloromethane. The extract is washed with water, dried over magnesium sulfate, and evaporated under reduced pressure to remove the solvent. The residue is crystallized from diethyl ether to give 7-chloro-1-{ 6-[2-(2-aminoethoxy)benzoylamino]nicotinoyl}- 2,3,4,5-tetrahydro-1H-benzazepine (110 mg) as white powder.

$^1$H-NMR (CDCl$_3$) δ:1.35–2.20 (4H, m), 2.60–3.40 (5H, m), 4.15– 4.30 (2H, m), 4.90–5.10 (1H, m), 6.61 (1H, d, J=8.2 Hz), 6.90–7.30 (4H, m), 7.40–7.55 (2H, m), 8.15–8.25 (3H, m), 10.81 (1H, s)

EXAMPLE 156

To a solution of 7-chloro-1-{6-[2-( 2-aminoethoxy)benzoylamino]-nicotinoyl}- 2,3,4,5-tetrahydro-1H-benzazepine (0.11 g) in methanol (3 ml) is added 37% formalin (0.24 ml), and thereto is added sodium cyanoborohydride (0.044 g), and thereto is added with stirring acetic acid (0.18 ml) at 10° C. The mixture is stirred at room temperature for one hour, and poured into ice-water, and the mixture is made basic with potassium carbonate, and extracted with dichloromethane. The extract is washed with water, dried over magnesium sulfate, and evaporated under reduced pressure to remove the solvent. The residue is purified by silica gel column chromatography, and the resultant is dissolved in ethanol (5 ml), and thereto is added conc. hydrochloric acid, and the mixture is stirred at room temperature for one hour. The mixture is evaporated under reduced pressure to remove the solvent, and crystallized from diethyl ether to give 7-chloro-1-{6-[2-( 2-dimethylaminoethoxy)benzoyl-amino]nicotinoyl}- 2,3,4,5-tetrahydro-1H-benzazepine dihydrochloride (53 mg) as white powder.

$^1$H-NMR (DMSO-d$_6$) δ:1.30–1.60 (1H, m), 1.80–2.15 (3H, m), 2.79 (6H, s), 2.60–3.20 (3H, m), 3.55 (2H, s), 4.53 (2H, s), 4.75–4.90 (1H, m), 5.60 (1H, brs), 6.87 (1H, d, J=8.4 Hz), 7.05–7.25 (3H, m), 7.45–7.75 (4H, m), 8.05– 8.15 (2H, m), 10.69 (1H, s), 10.90 (1H, brs)

Using the suitable starting compounds, there is obtained the compound of Example 91 in the same manner as in Example 156.

EXAMPLE 157

To a solution of 7-chloro-5-(4-t-butoxycarbonyl- 1-piperazinyl)-carbonylmethyl-1-[ 6-(2-chlorobenzoylamino)nicotinoyl]-2,3,4,5-tetrahydro- 1H-benzazepine (1.2 g)in dioxane (20 ml)is added 5 N hydrochloric acid (2 ml), and the mixture is stirred at room temperature overnight. Water is added to the reaction mixture, and the mixture is made basic with aqueous sodium hydroxide solution, and extracted with dichloromethane. The extract is washed with water, dried over magnesium sulfate, and evaporated under reduced pressure to remove the solvent. The residue is purified by silica gel column chromatography, and recrystallized from ethyl acetate-diethyl ether to give 7-chloro- 5-(1-piperazinyl)carboxymethyl-1-[6-( 2-chlorobenzoylamino)nicotinoyl]-2,3,4,5-tetrahydro- 1H-benzazepine (0.54 g) as white powder.

M.p. 157°–160° C.

EXAMPLE 158

To a solution of 7-chloro-5-methoxycarbonylmethyl-1-[6-( 2-chlorobenzoylamino)nicotinoyl]- 2,3,4,5-tetrahydro-1H-benzazepine (8 g) in ethylene glycol dimethyl ether (50 ml)is added sodium trimethoxyborohydride (6 g), and the mixture is refluxed for 4 hours. To the mixture is added sodium trimethoxyborohydride (3 g), and the mixture is refluxed for two hours. The reaction solution is gradually poured into diluted aqueous hydrochloric acid solution, and the mixture is extracted with dichloromethane. The extract is washed with water, dried over magnesium sulfate, and evaporated under reduced pressure to remove the solvent. The residue is purified by silica gel column chromatography, and recrystallized from dichloromethane-diethyl ether to give 7-chloro-5-(2-hydroxyethyl)-1-[ 6-(2-chlorobenzoylamino)nicotinoyl]- 2,3,4,5-tetrahydro-1 H-benzazepine (3.1 g) as white powder.

M.p. 161°–163° C.

Using the suitable starting compounds, there is obtained the compound of Example 123 in the same manner as in Example 158.

EXAMPLE 159

To a solution of 7-chloro-5-(2-hydroxyethyl)- 1-[6-(2-chlorobenzoylamino)nicotinoyl]- 2,3,4,5-tetrahydro-1H-benzazepine (0.3 g) in pyridine (6 ml) is added acetic anhydride (0.09 ml), and the mixture is stirred at 80° C. for 2 hours. The reaction solution is poured into water, and extracted with ethyl acetate. The extract is washed successively with diluted hydrochloric acid, water and aqueous sodium hydrogen carbonate solution, dried over magnesium sulfate, and evaporated under reduced pressure to remove the solvent. The residue is purified by silica gel column chromatography, and recrystallized from dichloromethane-diethyl ether to give 7-chloro- 5-(2-acetyloxyethyl)-1-[ 6-(2-chlorobenzoylamino )nicotinoyl]- 2,3,4,5-tetrahydro-1H-benzazepine (230 mg) as white powder.

M.p. 151°–153° C.

Using the suitable starting compounds, there is obtained the compound of Example 124 in the same manner as in Example 159.

EXAMPLE 160

To a solution of 7-chloro-5-(2-hydroxyethyl)-1-[ 6-(2-chlorobenzoyl-amino)nicotinoyl]- 2,3,4,5-tetrahydro-1H-benzazepine (3.7 g) in pyridine (50 ml) is added with stirring methanesulfonyl chloride (0.71 ml) under ice-cooling, and the mixture is stirred at room temperature for 3 hours. Water is added to the reaction solution, and the mixture is extracted with ethyl acetate. The extract is washed with successively with diluted hydrochloric acid and water, dried over magnesium sulfate, and evaporated under reduced pressure to remove the solvent. The residue is purified by silica gel column chromatography to give 7-chloro- 5-(2-methanesulfonyloxyethyl)-1-[6-(2-chlorobenzoylamino)nicotinoyl]-2,3,4,5-tetrahydro-1H-benzazepine (2.8 g) as colorless amorphous.

$^1$H-NMR (CDCl$_3$) δ:1.30–2.50 (6H, m), 2.55–3.45 (2H, m), 3.04 (3H, s), 4.20–4.60, 5.10–5.25 (3H, m), 6.64 (1H, d, J=8.3 Hz), 7.03 (1H, d, J=8.2 Hz), 7.15–7.50 (5H, m), 7.56 (1H, d, J=8.6 Hz), 7.72 (1H, d, J=6.2 Hz), 8.09 (1H, s), 8.21 (1H, d, J=8.7 Hz), 8.74 (1H, s)

Using the suitable starting compounds, there is obtained the compound of Example 134 in the same manner as Example 160.

EXAMPLE 161

To a solution of 7-chloro-5-(2-methanesulfonyloxyethyl)-1-[ 6-(2-chlorobenzoylamino)nicotinoyl]- 2,3,4,5-tetrahydro-1H-benzazepine (0.4 g) in dimethylformamide (5 ml) are added pyrrolidine (0.09 ml), sodium iodide (0.14 g) and potassium carbonate (0.15 g), and the mixture is stirred at 110° C. for 2 hours. Water is added to the reaction solution, and the mixture is extracted with dichloromethane. The extract is washed with water, dried over magnesium sulfate, and evaporated under reduced pressure to remove the solvent. The residue is purified by silica gel column chromatography to give 7-chloro- 5-[2-(1-pyrrolidinyl)ethyl]-1-[ 6-(2-chlorobenzoylamino)nicotinoyl]-2,3,4,5-tetrahydro-1H-benzazepine (98 mg) as colorless amorphous.

¹H-NMR (CDCl₃) δ: 1.30–2.80 (14H, m), 3.05–3.40 (2H, m), 4.25– 4.45, 5.05–5.25 (1H, m), 6.60 (1H, d, J=8.2 Hz), 6.90–7.05 (1H, m), 7.25–7.60 (5H, m), 7.72 (1H, d, J=6.4 Hz), 8.17 (1H, d, J=8.1 Hz), 8.70 (1H, s)

Using the suitable starting compounds, there are obtained the compounds of Examples 127–133 and 135–143 in the same manner as in Example 161.

EXAMPLE 162

To a solution of 7-chloro-5-(2-methanesulfonyloxyethyl)-1-[6-(2-chlorobenzoylamino)nicotinoyl]- 2,3,4,5-tetrahydro-1H-benzazepine (1.6 g) in dimethylformamide (30 ml) is added potassium phthalimide (0.58 g), and the mixture is stirred at 110° C. for 3 hours. The mixture is poured into ice-water, and the mixture is extracted with dichloromethane. The extract is washed with water, dried over magnesium sulfate, and evaporated under reduced pressure to remove the solvent. The residue is purified by silica gel column chromatography to give 7-chloro-5-(2-phthalimido-ethyl)- 1-[6-(2-chlorobenzoyl-amino)nicotinoyl]- 2,3,4,5-tetrahydro-1H-benzazepine (1.8 g) as colorless amorphous.

¹H-NMR (CDCl₃) δ: 1.25–2.50 (6H, m), 2.60–3.40 (2H, m), 3.70– 4.00 (2H, m), 4.30–4.50, 5.10–5.30 (1H, m), 6.62 (1H, d, J=8.5 Hz), 6.90–7.15 (1H, m), 7.25–7.60 (5H, m), 7.65–7.90 (5H, m), 8.00–8.30 (2H, m), 8.72 (1H, s)

Using the suitable starting compounds, there is obtained the compound of Example 141 in the same manner as in Example 162.

EXAMPLE 163

To a solution of 7-chloro-5-(2-phthalimidoethyl)- 1-[6-(2-chloro-benzoylamino)nicotinoyl]- 2,3,4,5-tetrahydro-1H-benzazepine (1.8 g) in ethanol (50 ml) is added hydrazine monohydrate (0.19 ml), and the mixture is refluxed for 4 hours. The mixture is cooled, and thereto is added water. The mixture is extracted with dichloromethane, and the extract is washed with water, dried over magnesium sulfate, and evaporated under reduced pressure to remove the solvent. The residue is purified by silica gel column chromatography to give 7-chloro-5-(2-aminoethyl)-1-[6-( 2-chlorobenzoylamino)nicotinoyl]-2,3,4,5-tetrahydro-1H-benzazepine (0.5 g) as colorless amorphous.

¹H-NMR (CDCl₃) δ: 1.20–2.30 (6H, m), 2.60–3.40 (4H, m), 4.25– 4.45, 5.05–5.25 (1H, m), 6.56–6.65 (1H,m), 6.90–7.05 (1H, m), 7.20–7.60 (5H, m), 7.69 (1H, d, J=6.4 Hz), 8.05– 8.25 (2H, m), 9.02 (1H, brs)

Using the suitable starting compounds, there is obtained the compound of Example 142 in the same manner as in Example 163.

EXAMPLE 164

To a solution of 7-chloro-5-(2-aminoethyl)-1-[ 6-(2-chlorobenzoyl-amino)nicotinoyl]- 2,3,4,5-tetrahydro-1H-benzazepine (0.5 g) in methanol (20 ml) is added 37% formalin (1.4 ml), and thereto is added sodium cyanoborohydride (0.2 g), and further thereto is added with stirring acetic acid (0.9 ml) at 10° C., and the mixture is stirred at room temperature for 3 hours. The mixture is poured into ice-water, and the mixture is made basic with potassium carbonate, and the mixture is extracted with dichloromethane. The extract is washed with water, dried over magnesium sulfate, and evaporated under reduced pressure to remove the solvent. The residue is purified by silica gel column chromatography to give 7-chloro-5-(2-dimethylaminoethyl)- 1-[6-(2-chlorobenzoylamino)nicotinoyl]- 2,3,4,5-tetrahydro-1H-benzazepine (0.37 g) as colorless amorphous.

¹H-NMR (CDCl₃) δ:1.20–2.80 (8H, m), 2.22, 2.26 (6H, s), 3.05– 3.40 (2H, m), 4.25–4.44, 5.10–5.20 (1H, m), 6.50–6.65 (1H, m), 6.90–7.05 (1H, m), 7.20–7.30 (1H, m), 7.30–7.60 (4H, m), 7.71 (1H, d, J=6.3 Hz), 8.15– 8.20 (2H, m), 8.73 (1H, s)

Using the suitable starting compounds, there are obtained the compounds of Examples 130 and 139 in the same manner as in Example 164.

EXAMPLE 165

To a solution of 7-chloro-5-(2-aminoethyl)-1-[ 6-(2-methylbenzoyl-amino)nicotinoyl]- 2,3,4,5-tetrahydro-1H-benzazepine (0.42 g) in pyridine (10 ml) is added acetic anhydride (0.13 ml), and the mixture is stirred at 80° C. for 2 hours, and then stirred at room temperature overnight. Water is added to the reaction solution, and the mixture is extracted with dichloromethane. The extract is washed successively with diluted hydrochloric acid, water, and aqueous sodium hydrogen carbonate solution, dried over magnesium sulfate, and evaporated under reduced pressure to remove the solvent. The residue is purified by silica gel column chromatography to give 7-chloro-5-( 2-acetylamino-ethyl)-1-[6-( 2-methylbenzoylamino)nicotinoyl]-2,3,4,5-tetrahydro- 1H-benzazepine (91 mg) as white powder.

¹H-NMR (CDCl₃) δ:1.20–2.30 (6H, m), 1.99 (3H, s), 2.50 (3H, s), 2.80–3.60 (4H, m), 4.30–4.50,5.05–5.25 (1H, m), 5.45–5.80 (1H, m), 6.55– 6.65 (1H, m), 6.95–7.05 (1H, m), 7.20–7.60 (6H, m), 8.00–8.30 (3H, m)

EXAMPLE 166

To a solution of 7-chloro-4,4-dimethoxy-1-[ 6-(2-methylbenzoyl-amino)nicotinoyl]- 2,3,4,5-tetrahydro-1H-benzazepine (1 g) in acetone (10 ml) is added 1N hydrochloric acid (5 ml), and the mixture is stirred at room temperature for 6 hours. Water is added to the reaction solution, and the mixture is neutralized with aqueous sodium hydroxide solution, and extracted with dichloromethane. The extract is washed with water, dried over magnesium sulfate, and evaporated under reduced pressure to remove the solvent. The residue is purified by silica gel column chromatography to give 7-chloro-4-oxo-1-[6-( 2-methylbenzoylamino )nicotinoyl]-2,3,4,5-tetrahydro- 1H-benzazepine (0.92 g) as colorless amorphous.

¹H-NMR (CDCl₃) δ:2.50 (3H, s), 2.65–3.00 (2H, m), 3.40–3.70 (2H, m), 4.00–4.30 (1H, m), 4.65–5.00 (1H, m), 6.73 (1H, d, J=8.4 Hz), 7.11 (1H, dd, J=2.4, 8.4 Hz), 7.20–7.65 (6H, m), 8.07 (1H, d, J=1.7 Hz), 8.24 (1H, d, J=8.7 Hz), 8.50 (1H, s)

EXAMPLE 167–198

Using the suitable starting compounds, the following compounds listed in Table 3 are obtained in the same manner as in Examples 1 and 17. Table 4 shows the NMR analysis of these compounds.

TABLE 3

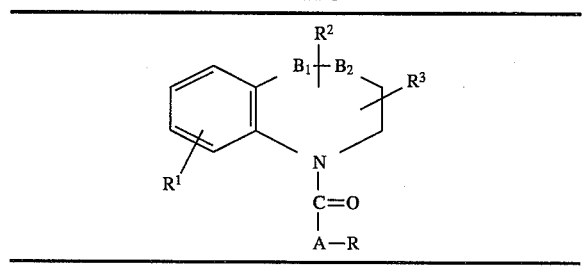

Example 167

Structure:

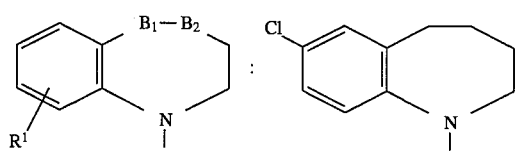

R²: —OCH₂CO—N⟨⟩N.CH₃

(5-position)

R³: H

—A—R: 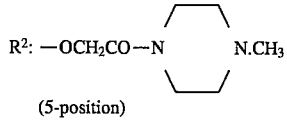

Crystalline Form: Colorless amorphous
NMR analysis: 57)
Form: Free

Example 168

Structure:

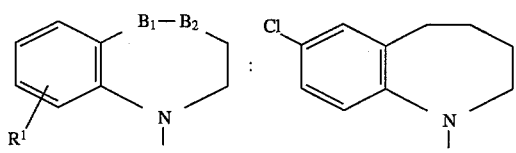

R²: —OCH₂COOH (5-position)
R³: H

—A—R: 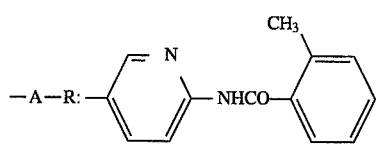

Crystalline Form: White powder
Recrystallization solvent: Diethyl ether-dichloromethane
Melting point: 220–222° C.
Form: Free Example 169

Structure:

TABLE 3-continued

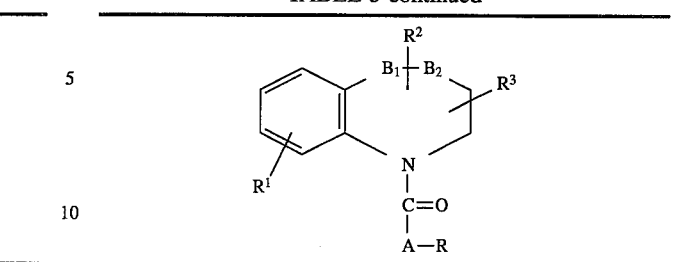

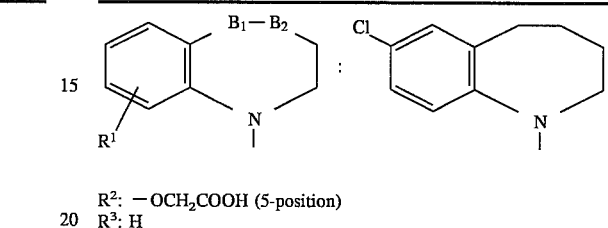

R²: —OCH₂COOH (5-position)
R³: H

—A—R: 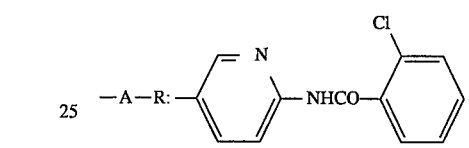

Crystalline Form: White powder
Recrystallization solvent: Dichloromethane-diethyl ether
Melting point: 223–225° C.
Form: Free Example 170

Structure:

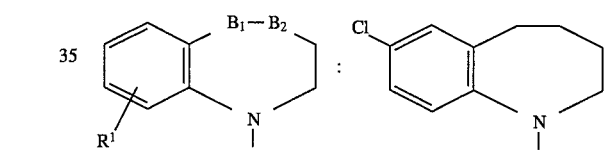

R²: —OCH₂CONH₂ (5-position)
R³: H

—A—R: 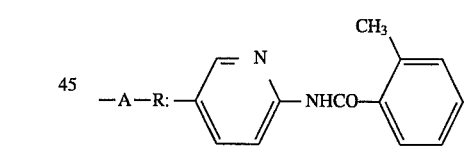

Crystalline Form: Colorless amorphous
NMR analysis: 58)
Form: Free

Example 171

Structure:

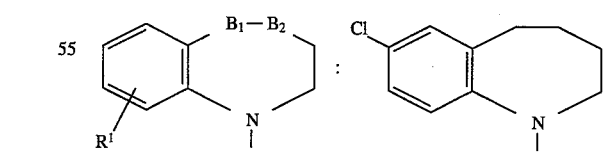

R²: —OCH₂CONH₂ (5-position)
R³: H

TABLE 3-continued

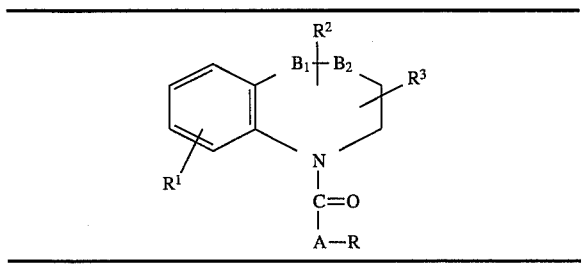

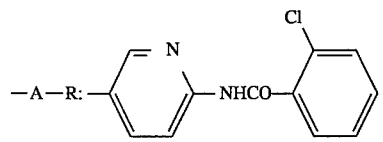

Crystalline Form: Colorless amorphous
NMR analysis: 59)
Form: Free
Example 172

Structure:

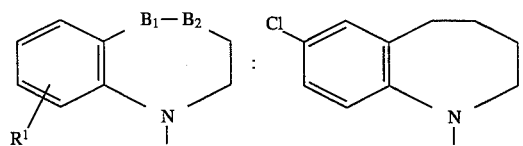

R²: —OCH₂CON(CH₃)₂ (5-position)
R³: H

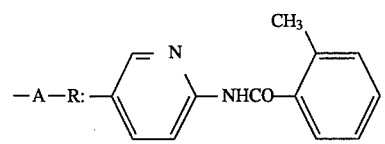

Crystalline Form: White powder
Recrystallization solvent: Dichloromethane-diethyl ether
Melting point: 107–110° C.
Form: Free
Example 173

Structure:

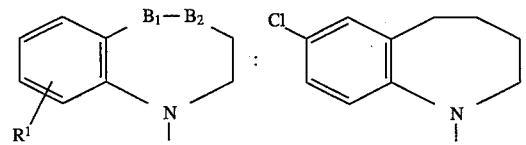

R²: —OCH₂CON(CH₃)₂ (5-position)
R³: H

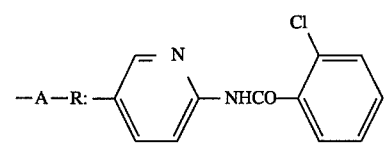

Crystalline Form: White powder
Recrystallization solvent: Dichloromethane-diethyl ether
Melting point: 119–122° C.
Form: Free
Example 174

Structure:

TABLE 3-continued

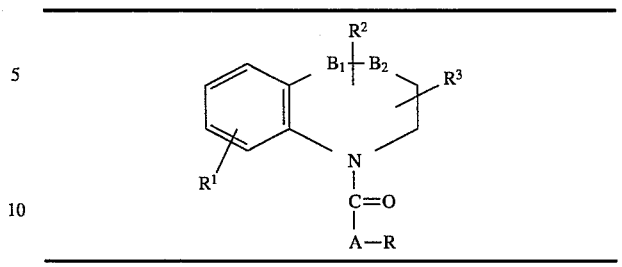

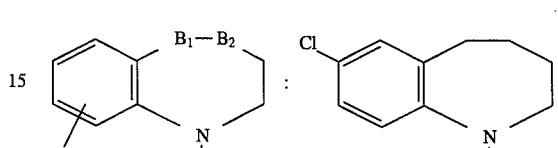

R²: —OCH₂CON$\begin{matrix}CH_3\\(CH_2)_2N(C_2H_5)_2\end{matrix}$ (5-position)

R³: H

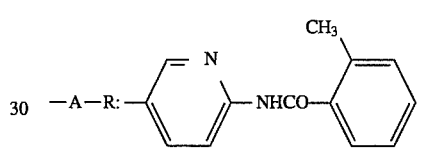

Crystalline Form: Colorless amorphous
NMR analysis: 60)
Form: Free
Example 175

Structure:

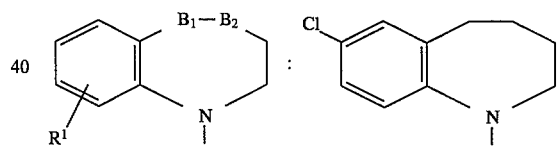

R²: —OCH₂CON$\begin{matrix}CH_3\\(CH_2)_2N(C_2H_5)_2\end{matrix}$ (5-position)

R³: H

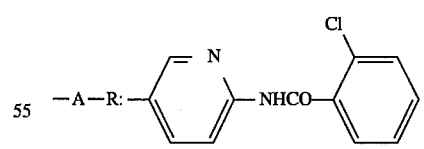

Crystalline Form: Colorless amorphous
NMR analysis: 61)
Form: Free
Example 176

Structure:

TABLE 3-continued

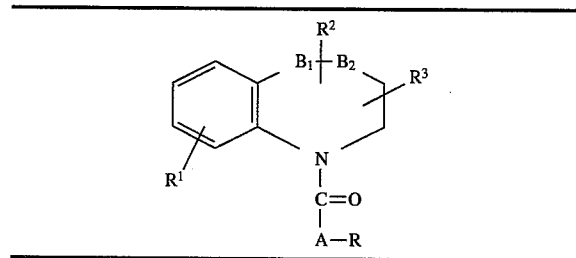

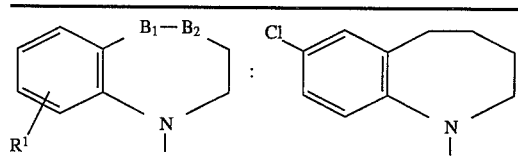

R²: —O(CH₂)₂OH (5-position)
R³: H

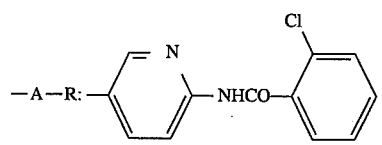

Crystalline Form: Colorless amorphous
NMR analysis: 62)
Form: Free
Example 177

Structure:

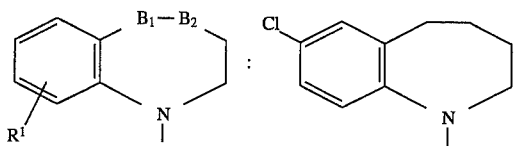

R²: —O(CH₂)₂N(CH₃)₂ (5-position)
R³: H

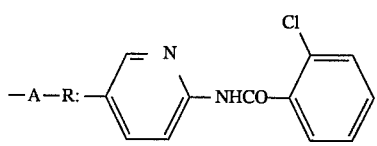

Example 178

Structure:

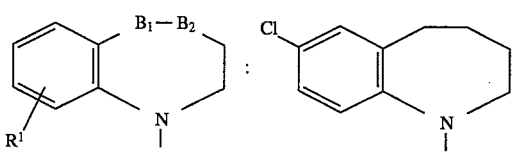

R²: —O(CH₂)₂—N⌒N
(5-position)

R³: H

TABLE 3-continued

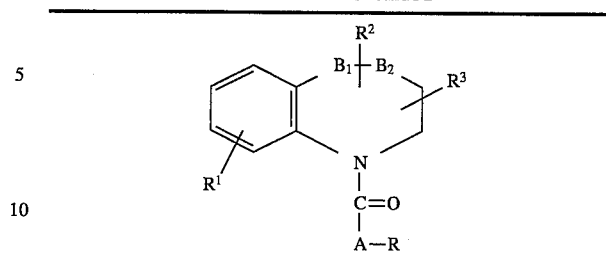

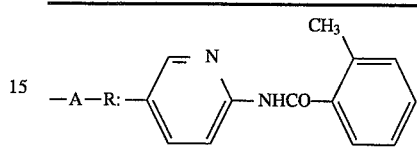

Crystalline Form: Colorless amorphous
NMR analysis: 63)
Form: Free
Example 179

Structure:

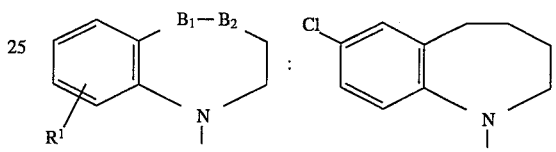

R²: —O(CH₂)₂—N⌒N
(5-position)

R³: H

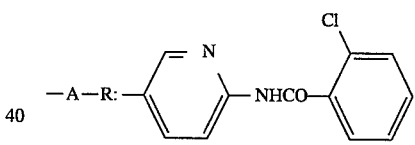

Example 180

Structure:

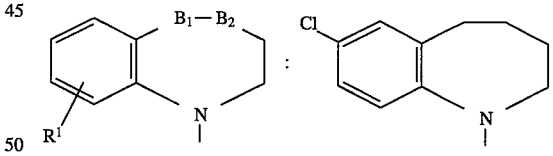

R²: —O(CH₂)₂—N⌒N—COCH₃
(5-position)

R³: H

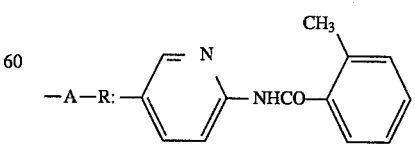

Crystalline Form: Colorless amorphous
NMR analysis: 64)
Form: Free

TABLE 3-continued

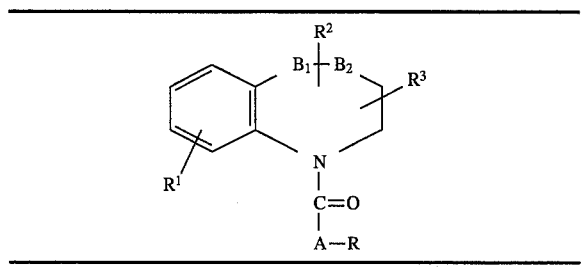

Example 181

Structure:

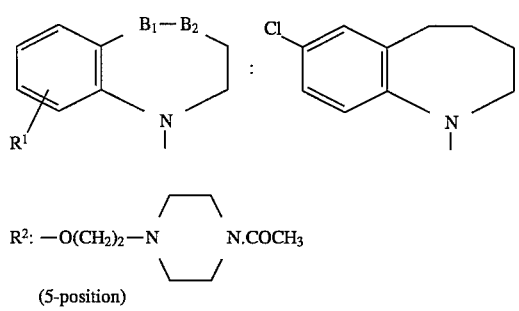

R²: —O(CH₂)₂—N⌒N.COCH₃

(5-position)

R³: H

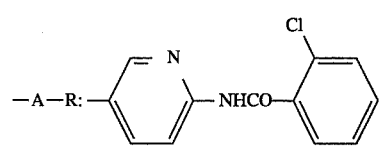

Crystalline Form: Colorless amorphous
NMR analysis: 65)
Form: Free

Example 182

Structure:

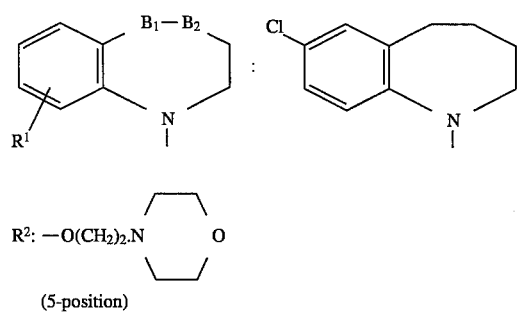

R²: —O(CH₂)₂.N⌒O (5-position)

R³: H

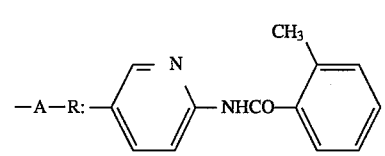

Crystalline Form: Colorless amorphous
NMR analysis: 66)
Form: Free

Example 183

Structure:

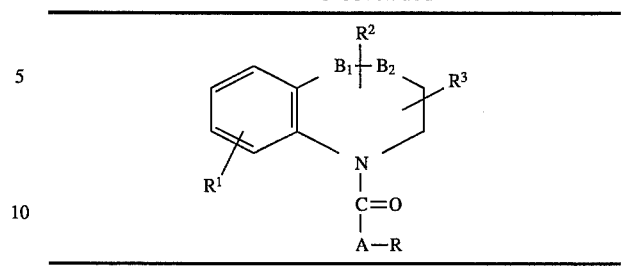

R²: —O(CH₂)₂.N⌒O (5-position)

R³: H

—A—R: 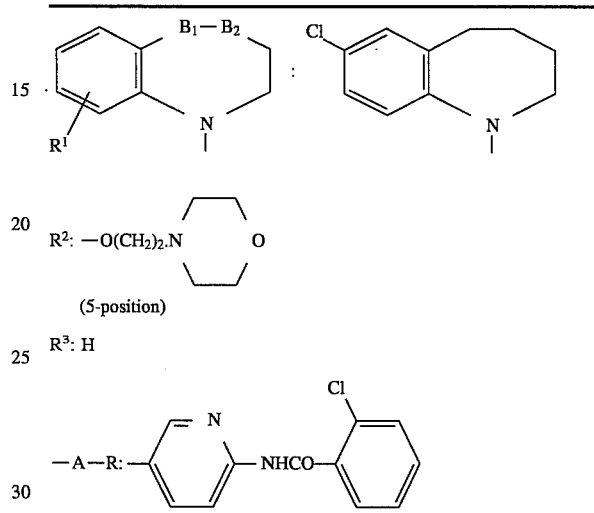

Crystalline Form: Colorless amorphous
NMR analysis: 67)
Form: Free

Example 184

Structure:

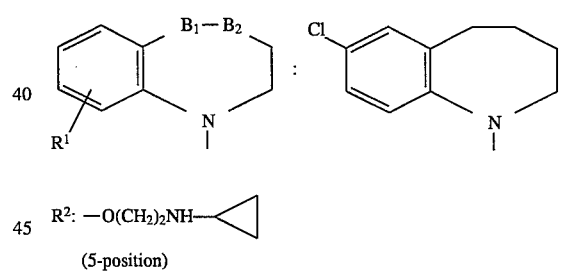

R²: —O(CH₂)₂NH—◁

(5-position)

R³: H

—A—R: 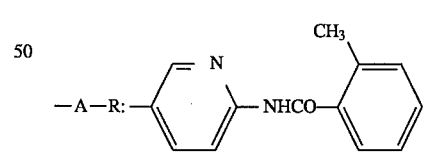

Crystalline Form: Colorless amorphous
NMR analysis: 68)
Form: Free

Example 185

Structure:

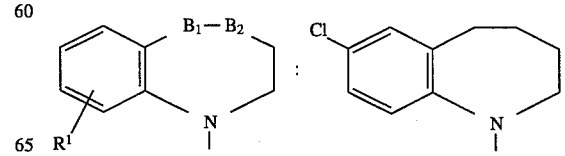

TABLE 3-continued

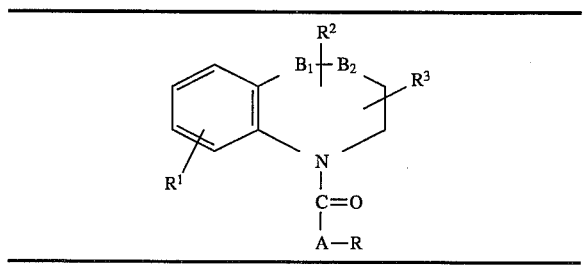

R²: —O(CH₂)₂NH—<cyclopropyl>

(5-position)

R³: H

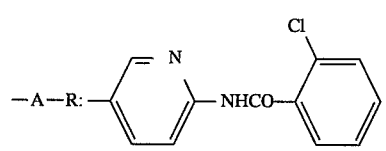

Crystalline Form: Yellow amorphous
NMR analysis: 69)
Form: Free
Example 186

Structure:

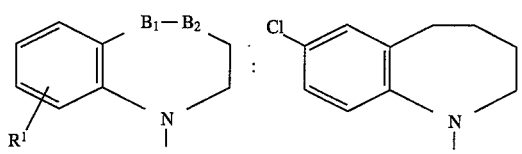

R²: —O(CH₂)₂NH—<cyclopentyl>

(5-position)

R³: H

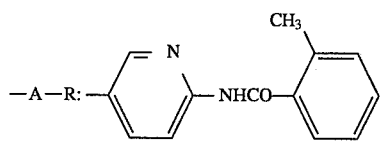

Crystalline Form: Brown amorphous
NMR analysis: 70)
Form: Free
Example 187

Structure:

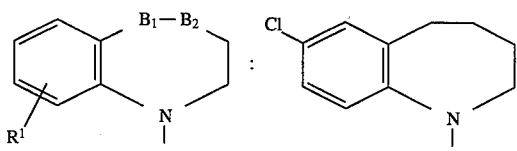

R²: —O(CH₂)₂NH—<cyclopentyl>

(5-position)

R³: H

TABLE 3-continued

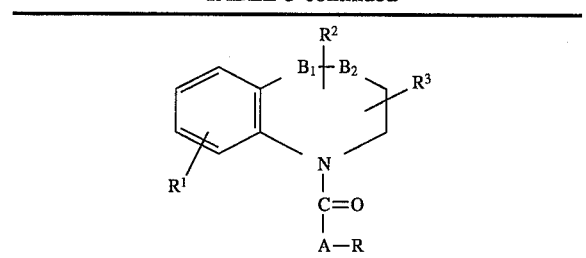

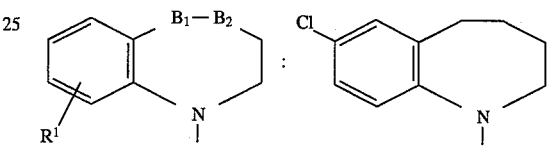

Crystalline Form: Brown amorphous
NMR analysis: 71)
Form: Free
Example 188

Structure:

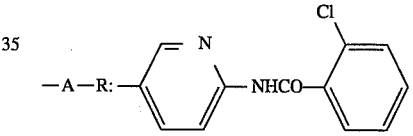

R²: —O(CH₂)₂NHCOCH₃ (5-position)
R³: H

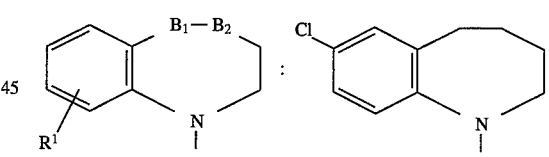

Example 189

Structure:

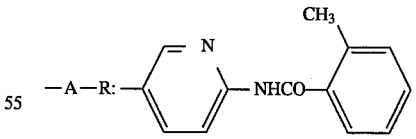

R²: —OCOCH₂N(CH₃)₂ (5-position)
R³: H

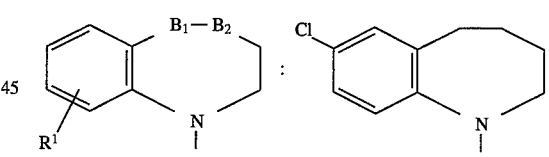

Crystalline Form: Colorless amorphous
NMR analysis: 72)
Form: 2 HCl
Example 190

Structure:

TABLE 3-continued

[Structure: Ar-N(R¹)(B₁-B₂-C(R²)(R³)-)-N-C(=O)-A-R general formula]

---

-A-R: (benzazepine with Cl)

R²: —OCOCH₂N(CH₃)₂ (5-position)
R³: H

-A-R: pyridine-NHCO-(2-chlorophenyl)

Crystalline Form: Colorless amorphous
NMR analysis: 73)
Form: Free

Example 191

Structure:

(aniline-B₁-B₂ : F-benzazepine)

R²: —OH (5-position)
R³: H

-A-R: pyridine-NHCO-(2-chlorophenyl)

Crystalline Form: White powder
Recrystallization solvent: Diethyl ether
Melting point: 115–118° C.
Form: Free Example 192

Structure:

(aniline-B₁-B₂ : F-benzazepine)

R²: —N(CH₃)₂ (5-position)
R³: H

-A-R: pyridine-NHCO-(2-chlorophenyl)

Crystalline Form: Colorless oil
NMR analysis: 74)
Form: Free

Example 193

Structure:

(aniline-B₁-B₂ : Cl-benzazepine)

R²: H
R³: H

-A-R: thiazole-NHCO-(2-chlorophenyl)

Example 194

Structure:

(aniline-B₁-B₂ : Cl-benzazepine)

R²: H
R³: H

-A-R: thiazole-NHCO-(2-methylphenyl)

Example 195

Structure:

(aniline-B₁-B₂ : Cl-benzazocine)

TABLE 3-continued

[Structure diagram with R², B₁, B₂, R³, R¹, N, C=O, A—R]

R²: —CH₂CO—N(piperazine)N.CH₃
(5-position)

R³: H

—A—R: [thiazole]—NHCO—[2-chlorophenyl]

Example 196

Structure:

[Two-ring structure with B₁—B₂, R¹, N; and 7-chloro-tetrahydrobenzazepine]

R²: —CH₂CO—N(piperazine)N.CH₃
(5-position)

R³: H

—A—R: [thiazole]—NHCO—[2-methylphenyl]

Example 197

Structure:

[Two-ring structure with B₁—B₂, R¹, N; and 7-chloro-tetrahydrobenzazepine]

R²: —CH₂CON(CH₂)₂N(C₂H₅)₂ with CH₃
(5-position)

R³: H

TABLE 3-continued

[Structure diagram with R², B₁, B₂, R³, R¹, N, C=O, A—R]

—A—R: [thiazole]—NHCO—[2-chlorophenyl]

Example 198

Structure:

[Two-ring structure with B₁—B₂, R¹, N; and 7-chloro-tetrahydrobenzazepine]

R²: —CH₂CON(CH₂)₂N(C₂H₅)₂ with CH₃
(5-position)

R³: H

—A—R: [thiazole]—NHCO—[2-methylphenyl]

TABLE 4

57) ¹H-NMR (CDCl₃) δ:1.60– 1.90 (2H, m), 2.30–2.65 (9H, m), 2.70– 3.05 (1H, m), 3.45–3.80 (4H, m), 4.20–5.20 (4H, m), 6.55–6.70 (1H, m), 7.00– 7.15 (1H, m), 7.30–7.50 (3H, m), 7.50–7.85 (3H, m), 8.20–8.30 (2H, m), 8.86 (1H, s)

58) ¹H-NMR (CDCl₃) 821.60–2.60 (4H, m), 2.50 (3H, s), 2.70–3.05 (1H, m), 4.00–4.20 (2H, m), 4.50–5.15 (2H, m), 5.70–6280 (2H, m), 6.60–6.80 (1H, m), 7.00–7.75 (7H, m), 8.00–8.30 (2H, m), 8.53 (1H, s)

59) ¹H-NMR (CDCl₃) δ:1.60–2.55 (4H, m), 2.70–3.05 (1H, m), 3.90– 4.25 (2H, m), 4.50–5.15 (2H, m), 5.85–6.80 (2H, m), 6.55–6.80 (1H, m), 7.00– 7.20 (1H, m), 7.25–7.55 (4H, m), 7.55–7.75 (2H, m), 8.00–8.30 (2H, m), 8.99 (1H, s)

60) ¹H-NMR (CDCl₃) δ:0.85–1.15 (6H, m), 1.55–1.90 (2H, m), 2.25– 2.70 (11H, m), 2.70–3.15 (4H, m), 3.20–3.65 (2H, m), 4.15–5.20 (4H, m), 6.55– 6.70 (1H, m), 7.00–7.15 (1H, m), 7.20–7.85 (6H, m), 8.05–8.35 (2H, m), 8.35– 8.50 (1H, m)

61) $^1$H-NMR (CDCl$_3$) δ:0.85–1.15 (6H, m), 1.55–1.90 (2H, m), 2.30– 2.70 (8H, m), 2.70–3.15(4H, m), 3.20–3.65 (2H, m), 4.15–5.20 (4H, m), 6.55– 6.75 (1H, m), 6.95–7.15(1H, m), 7.30–7.55 (3H, m), 7.55–7.85 (3H, m), 8.10– 8.35 (2H, m), 8.75–8.95(1H, m)

62) $^1$H-NMR (CDCl$_3$) δ : 1.50–2.55 (4H, m), 2.70–3.00 (1H, m), 3.50– 4.00 (4H, m), 4.50–5.10 (2H, m), 6.61 (1H, d, J=8.1 Hz), 7.00–7.15 (1H, m), 7.25–7.85 (6H, m), 8.05–8.35 (2H, m), 8.85 (1H, s)

63) $^1$H-NMR (CDCl$_3$) δ:1.50–2.60 (4H, m), 2.51 (3H, s), 2.65–3.05 (1H, m), 3.70–4.05 (2H, m), 4.05–5.20 (4H, m), 6.55–6.70 (1H, m), 6.90–7.80 (10H, m), 8.05–8.25 (2H, m), 8.52, 8.61 (1H, s)

64) $^1$H-NMR (CDCl$_3$) δ:1.60–1.90 (2H, m), 2.01,2.06 (3H, s), 1.90–3.00 (9H, m), 2.50 (3H, s), 3.30–3.85 (6H, m), 4.45–5.15 (2H, m), 6.62 (1H, d, J=8.3 Hz), 7.04 (1H, d, J=8.2 Hz), 7.20–7.85 (6H, m), 8.05–8.35 (2H, m), 8.52, 8.57 (1H, s)

65) $^1$H-NMR (CDCl$_3$) δ:1.55–3.00 (11H, m), 2.02, 2.10 (3H, s), 3.30– 3.85 (6H, m), 4.40–5.15 (2H, m), 6.62 (1H, d, J=8.1 Hz), 7.04 (1H, d, J=8.3 Hz), 7.35–7.90 (6H, m), 8.10–8.40 (2H, m), 8.76, 8.80 (1H, s)

66) $^1$H-NMR (CDCl$_3$) δ:1.55–3.00 (11H, m), 2.50 (3H, s), 3.55–3.90 (6H, m), 4.45–5.15 (2H, m), 6.61 (1H, d, J=8.2 Hz), 7.03 (1H, d, J=8.2 Hz), 7.20– 7.85 (6H, m), 8.05–8.35 (2H, m), 8.51 (1H, s)

67) $^1$H-NMR (CDCl$_3$) δ:1.55–3.00 (11H, m), 3.55–3.90 (6H, m), 4.45– 5.15 (2H, m), 6.61(1H, d, J=8.3 Hz), 7.03 (1H, d, J=8.2 Hz), 7.30–7.85 (6H, m), 8.10–8.35 (2H, m), 8.75, 8.80 (1H, s)

68) $^1$H-NMR (CDCl$_3$) δ:0.20–0.60 (4H, m), 1.55–2.65 (5H, m), 2.50 (3H, s), 2.65–3.10 (3H, m), 3.50–3.85 (2H, m), 4.40–5.15 (2H, m), 6.62 (1H, d, J=8.2 Hz), 7.04 (1H, d, J=8.1 Hz), 7.20–7.80 (6H, m), 8.09–8.40 (3H, m)

69) $^1$H-NMR (CDCl$_3$) δ: 0.20–0.60 (4H, m), 1.50–2.60 (5H, m), 2.65– 3.10 (3H, m), 3.50–3.80 (2H, m), 4.45–5.15 (2H, m), 6.61 (1H, d, J=8.4 Hz), 7.04 (1H, d, J=6.9 Hz), 7.30–7.85 (6H, m), 8.05–8.35 (2H, m), 8.78 (1H

70) $^1$H-NMR (CDCl$_3$) δ:1.05–2.20 (12H, m), 2.20–2.60 (1H, m), 2.50 (3H, s), 2.70–3.05 (3H, m), 3.50–3.90 (2H, m), 4.45–5.15 (2H, m), 6.55–6.70 (1H, m), 7.04 (1H, d, J=8.4 Hz),7.20– 7.80 (6H, m), 8.05–8.30 (2H, m), 8.35–8.50 (1H, m)

71) $^1$H-NMR (CDCl$_3$) δ: 1.05–2.60 (12H, m), 2.65–3.30 (4H,), 2.50– 3.85 (2H, m), 4.45–5.10 (2H, m), 6.55–6.70 (1H, m), 7.04 (1H, d, J=8.0 Hz), 7.30–7.80 (6H, m), 8.10–8.33 (2H, m), 8.60–8.90 (1H, m)

72) $^1$H-NMR (CDCl$_3$) δ:1.60–2.45 (4H, m), 2.30–2.40 (3H, m), 2.70– 3.10 (7H, m), 4.10–5.00 (3H, m), 6.05–6.20 (1H, m), 6.95 (1H, d, J=8.2 Hz), 7.15–7.60 (6H, m), 7.70–7.90 (1H, m), 8.03 (1H, d, J=8.6 Hz), 8.20 (1H, s), 11.04 (1H, s), 11.28, 11.85 (1H, s)

73) $^1$H-NMR (CDCl$_3$) δ:2.34, 2.43 (6H, s), 1.70–2.65 (5H, m), 2.70– 3.00 (1H, m), 3.40 (2H, s), 4.70–5.15 (1H, m), 6.00–6.20 (1H, m), 6.55–6.70 (1H, m), 7.00–7.15 (1H, m), 7.30–7.45 (3H, m), 7.50–7.70 (2H, m), 8.05–8.25 (2H, m), 9.15–9.50 (1H, br)

74) $^1$H-NMR (CDCl$_3$) δ: 1.16–2.57 (4H, m), 2.15, 2.40 (total, 6H, s), 2.61– 3.63 (2H, m), 4.03–5.09 (1H, m), 6.53–8.26 (10H, m), 8.36, 8.77 (total, 1H, brs)

Pharmacological Test

Experiment 1: V$_1$ receptor binding assay

Using rat liver plasma membrane preparations prepared according to Ichihara's method [cf: Akira Ichihara, J. Bio. Chem., 258, 9283 (1983)], the plasma membrane (50000 dpm, 2×10$^{-10}$M) of [$^3$H]-Arg-vasopressin and a test compound (60 μg, 10$^{-8}$ to 10$^{-4}$ M) are incubated at 37° C. for 10 minutes in 100 mM Tris-HCl buffer (pH: 8.0) (250 μl) containing 5 mM MgCl$_2$, 1 mM EDTA and 0.1% BSA. After incubation, the mixture is filtered three times using the glass filter (GF/F) so as to separate the membrane preparation binding with vasopressin and then washed with the buffer (5 ml). This glass filter is taken out and mixed with liquid scintillation cocktail. The amount of [$^3$H]-vasopressin binding with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_1} \times 100$$

$C_1$: The amount of [$^3$H]-vasopressin binding with the membrane in the presence of the test compound (known amount)

$C_0$: The amount of [$^3$H]-vasopressin binding with the membrane in the absence of the test compound $B_1$: The amount of [$^3$H]-vasopressin binding with the membrane in the presence of the excess amount of vasopressin (10$^{-6}$ M)

The results are expressed as IC$_{50}$ value, which is the concentration of the test compound required to achieve the inhibitory effect in the rate of 50%.

The results are shown in the following Table 5.

Experiment 2: V$_2$ receptor binding assay

Using rat kidney plasma membrane preparations prepared according to O. Hechter's method [cf: J. Bio. Chem., 253, 3211 (1978)], the plasma membrane (100000 dpm, 4×10$^{-10}$ M) of [$^3$H]-Arg-vasopressin and a test compound (0.6 mg, 10$^{-10}$ to 10$^{-5}$ M) are incubated at 4° C. for 3 hours in 100 mM Tris-HCl buffer (pH: 8.0) (250 μl) containing 5 mM MgCl$_2$, 1 mM EDTA and 0.1% BSA. After incubation, the mixture is filtered using the glass filter (GF/F) so as to separate the membrane preparation binding with vasopressin and then washed twice with the buffer (each 5 ml). This glass filter is taken out and mixed with liquid scintillation cocktail. The amount of [$^3$H]-vasopressin binding with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_1} \times 100$$

$C_1$: The amount of [$^3$H]-vasopressin binding with the membrane in the presence of the test compound (known amount)

$C_0$: The amount of [$^3$H]-vasopressin binding with the membrane in the absence of the test compound $B_1$: The amount of [$^3$H]-vasopressin binding with the membrane in the presence of the excess amount of vasopressin (10$^{-6}$ M)

The results are expressed as IC$_{50}$ value, which is the concentration of the test compound required to achieve the inhibitory effect in the rate of 50%.

The results are shown in the following Table 5.

TABLE 5

| Test compound No | $IC_{50}$ (µM) in V1 receptor binding assay | $IC_{50}$ (µM) in V2 receptor binding assay |
|---|---|---|
| Compound of Ex. 25 | 0.014 | 0.004 |
| Compound of Ex. 26 | 0.078 | 0.021 |
| Compound of Ex. 28 | 0.077 | 0.17 |
| Compound of Ex. 29 | 0.024 | 0.011 |
| Compound of Ex. 31 | 0.057 | 0.12 |
| Compound of Ex. 32 | 0.012 | 0.016 |
| Compound of Ex. 33 | 0.007 | 0.003 |
| Compound of Ex. 34 | 0.066 | 0.016 |
| Compound of Ex. 35 | 0.020 | 0.007 |
| Compound of Ex. 36 | 0.043 | 0.003 |
| Compound of Ex. 37 | 0.011 | 0.005 |
| Compound of Ex. 38 | 0.026 | 0.003 |
| Compound of Ex. 39 | 0.91 | 0.068 |
| Compound of Ex. 40 | 0.044 | 0.009 |
| Compound of Ex. 41 | 0.022 | 0.004 |
| Compound of Ex. 42 | 0.030 | 0.003 |
| Compound of Ex. 43 | 0.013 | 0.010 |
| Compound of Ex. 44 | 0.008 | 0.011 |
| Compound of Ex. 45 | 0.005 | 0.007 |
| Compound of Ex. 47 | 0.15 | 0.089 |
| Compound of Ex. 48 | 0.067 | 0.30 |
| Compound of Ex. 49 | 0.041 | 0.25 |
| Compound of Ex. 50 | 0.078 | 0.061 |
| Compound of Ex. 52 | 0.051 | 0.022 |
| Compound of Ex. 53 | 0.055 | 0.019 |
| Compound of Ex. 73 | 0.012 | 0.0019 |
| Compound of Ex. 76 | 0.027 | 0.008 |
| Compound of Ex. 78 | 0.017 | 0.010 |
| Compound of Ex. 79 | 0.041 | 0.0037 |
| Compound of Ex. 83 | 0.071 | 0.43 |
| Compound of Ex. 88 | 0.026 | 0.20 |
| Compound of Ex. 92 | 0.060 | 0.38 |
| Compound of Ex. 94 | 0.042 | 0.036 |
| Compound of Ex. 96 | 0.043 | 0.30 |
| Compound of Ex. 97 | 0.005 | 0.16 |
| Compound of Ex. 101 | 0.49 | 0.033 |
| Compound of Ex. 104 | 0.038 | 0.024 |
| Compound of Ex. 105 | 0.009 | 0.003 |
| Compound of Ex. 112 | 0.009 | 0.003 |
| Compound of Ex. 114 | 0.011 | 0.003 |
| Compound of Ex. 116 | 0.012 | 0.0031 |
| Compound of Ex. 122 | 0.015 | 0.003 |
| Compound of Ex. 123 | 0.020 | 0.0032 |
| Compound of Ex. 126 | 0.019 | 0.0053 |
| Compound of Ex. 127 | 0.029 | 0.0059 |
| Compound of Ex. 128 | 0.016 | 0.0046 |
| Compound of Ex. 129 | 0.031 | 0.0048 |
| Compound of Ex. 139 | 0.016 | 0.0041 |
| Compound of Ex. 140 | 0.031 | 0.0056 |
| Compound of Ex. 143 | 0.0066 | 0.0031 |
| Compound of Ex. 148 | 0.027 | 0.017 |
| Compound of Ex. 173 | 0.024 | 0.0053 |
| Compound of Ex. 175 | 0.0084 | 0.0027 |
| Compound of Ex. 171 | 0.0071 | 0.0031 |
| Compound of Ex. 169 | 0.117 | 0.019 |
| Compound of Ex. 178 | 0.029 | 0.0080 |
| Compound of Ex. 182 | 0.028 | 0.010 |
| Compound of Ex. 187 | 0.0078 | 0.0080 |
| Compound of Ex. 181 | 0.015 | 0.0044 |
| Compound of Ex. 189 | 0.034 | 0.012 |

Experiment 3: Oxytocin receptor binding assay

According to the method of W. Y. Chan et al. [Endocrinology, 126, 2095–2101 (1990)], uterine muscle is taken out from a rat which has previously been injected subcutaneously with diethylstilbestrol the day before, and homogenized, which is used as a membrane preparation. The membrane preparation (0.2 mg), [$^3$H]-oxytocin (100000 dpm, $10^{-9}$ M), a test compound ($10^{-9}$–$10^{-5}$ M) are incubated at 25° C. for one hour in 100 mM Tris-HCl buffer (pH 8.0, 250 µl) containing a 5 mM MgCl$_2$, 1 mM MEDTA and 0.1% BSA. The mixture is filtered through the glass filter (GF/B) so as to separate the membrane preparation binding with [$^3$H]-oxytocin, and then, washed twice with the buffer (5 ml). This glass filter is put into a vial and mixed with Aquasole (liquid scintillation cocktail). The amount of [$^3$H]-oxytocin binding with the membrane is measured by liquid scintillation counter. The rate of the inhibitory effect of the test compound is estimated according to the following equation.

Inhibitory Rate (%)=100-[($C_1$-B)/($C_0$-B)]×100

$C_1$: The amount of [$^3$H]-oxytocin binding with the membrane in the presence of a test compound (known amount)

$C_0$: The amount of [$^3$H]-oxytocin binding with the membrane in the absence of a test compound B: The amount of [$^3$H]-oxytocin binding with the membrane in the presence of the excess amount of oxytocin ($5 \times 10^{-6}$ M).

The results are expressed as $IC_{50}$ value, which is the concentration of the test compound required to achieve the inhibitory rate in the rate of 50%.

The results are shown in the following Table 6.

TABLE 6

| Test compound No. | $IC_{50}$ (µM) | Test Compound No. | $IC_{50}$ (µM) |
|---|---|---|---|
| Compound of Ex. 37 | 1.14 | Compound of Ex. 40 | 0.74 |
| Compound of Ex. 44 | 0.307 | Compound of Ex. 45 | 0.26 |
| Compound of Ex. 46 | 0.36 | Compound of Ex. 43 | 0.29 |
| Compound of Ex. 52 | 1.6 | Compound of Ex. 72 | 0.44 |
| Compound of Ex. 76 | 1.5 | Compound of Ex. 77 | 1.8 |
| Compound of Ex. 80 | 1.0 | Compound of Ex. 82 | 9.7 |
| Compound of Ex. 83 | 6.6 | Compound of Ex. 86* | 17% |
| Compound of Ex. 88 | 4.5 | Compound of Ex. 89 | 7.3 |
| Compound of Ex. 91* | 38% | Compound of Ex. 92* | 38% |
| Compound of Ex. 97 | 1.8 | Compound of Ex. 94 | 0.84 |
| Compound of Ex. 104 | 0.51 | Compound of Ex. 107 | 0.41 |
| Compound of Ex. 112 | 0.28 | Compound of Ex. 114 | 0.32 |
| Compound of Ex. 101 | 3.5 | Compound of Ex. 120 | 0.35 |
| Compound of Ex. 122 | 0.64 | Compound of Ex. 145 | 1.2 |
| Compound of Ex. 123 | 0.32 | Compound of Ex. 126 | 1.32 |
| Compound of Ex. 127 | 0.68 | | |

*): Inhibitory Rate (%) at $10^{-5}$ M

We claim:

1. A benzoheterocyclic compound of the formula (1):

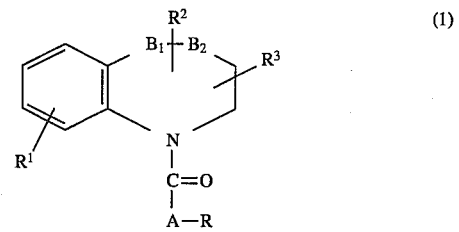

wherein $R^1$ is hydrogen atom or a halogen atom, $R^2$ is hydrogen atom, oxo group, a lower alkylidene group, hydroxy group, a lower alkoxy group, a lower alkenyloxy group, a hydroxy-substituted lower alkoxy group, a lower alkoxycarbonyl-substituted lower alkoxy group, a carboxy-substituted lower alkoxy group, a lower alkylsulfonyloxy-substituted lower alkoxy group, a phthalimide-substituted lower alkoxy group, a hydroxy-substituted lower alkyl group, a group of the formula: —O—D—(CO)$_1$NR$^4$R$^5$ (wherein D is a lower alkylene group, l is 0 or 1, R$^4$ and R$^5$ are the same or different and are hydrogen atom, a lower alkyl group, a lower alkanoyl group, a cycloalkyl group, or an amino-substituted lower alkyl group which may optionally have a lower alkyl substituent, or $R^4$ and $R^5$ may combine together with the nitrogen atom to which they bond to form a 5- or 6-membered saturated heterocyclic group which may be intervened or not with a nitrogen atom, an oxygen atom or a sulfur atom, wherein said heterocyclic group may optionally be substituted by a lower alkyl group or a lower alkanoyl group), a group of the formula: —E—$(CO)_1NR^6R^7$ (wherein I is the same as defined above, E is a lower alkylene group, $R^6$ and $R^7$ are the same or different and are hydrogen atom, a lower alkyl group, an amino-substituted lower alkyl group which may optionally have a lower alkyl substituent, or a lower alkanoyl group, or $R^6$ and $R^7$ may combine together with the nitrogen atom to which they bond to form a 5- or 6-membered saturated heterocyclic group which may be intervened or not with a nitrogen atom, an oxygen atom or a sulfur atom, wherein said heterocyclic group may optionally be substituted by a lower alkyl group, a lower alkanoyl group or a lower alkoxycarbonyl group), a lower alkanoyloxy-substituted lower alkyl group, a lower alkoxycarbonyl-substituted lower alkyl group, an amino which may optionally be substituted by a lower alkyl group or a cycloalkyl group, a carboxy-substituted lower alkyl group, a lower alkylsulfonyloxy-substituted lower alkyl group, a phthalimide-substituted lower alkyl group, an imidazolyl-substituted lower alkyl group, a 1,2,4-triazolyl-substituted lower alkyl group, an amino-substituted lower alkanoyloxy group which may optionally have a lower alkyl substituent, or an imidazolyl-substituted lower alkoxy group, $R^3$ is hydrogen atom, a lower alkoxy group or a hydroxy-substituted lower alkyl group, $B_1$ and $B_2$ are each methylene group A is a 5- or 6-membered unsaturated heterocyclic residue having 1 to 2 heteroatoms selected from an oxygen atom, a nitrogen atom and a sulfur atom, and R is a group of the formula: —$NHR^4$ or a group of the formula:

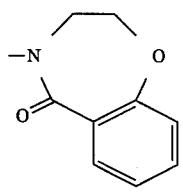

wherein $R^4$ is a group of the formula:

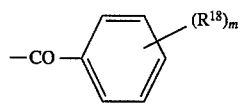

wherein m is an integer of 1 to 3, $R^{18}$ is hydrogen atom, a lower alkyl group, a lower alkoxy group, a halogen atom, nitro group, a lower alkoxycarbonyl group, carboxy group, a lower alkoxycarbonyl-substituted lower alkoxy group, a hydroxy-substituted lower alkoxy group, a carboxy-substituted lower alkoxy group, a lower alkylsulfonyloxy-substituted lower alkoxy group, a phthalimide-substituted lower alkoxy group, or a group of the formula: —O—E—$(CO)_lNR^{19}R^{20}$ (wherein E and I are the same as defined above, $R^{19}$ and $R^{20}$ are the same or different and are hydrogen atom or a lower alkyl group, or $R^{19}$ and $R^{20}$ may combine together with the nitrogen atom to which they bond to form a 5- or 6-membered saturated heterocyclic group which may be intervened or not with a nitrogen atom or an oxygen atom, wherein said heterocyclic group may optionally be substituted by a lower alkyl group, or an amino group which may optionally be substituted by a lower alkanoyl group), thienylcarbonyl group, a cycloalkylcarbonyl group or a phenyl-lower alkanoyl group which may optionally have a lower alkyl substituent on the phenyl ring, or a salt thereof.

2. The benzoheterocyclic compound according to claim 1, wherein both $B^1$ and $B^2$ are methylene group, the unsaturated heterocyclic residue for A is imidazolyl, pyrrolyl, imidazolinyl, pyridyl, pyrimidinyl, oxazolyl, pyrazolyl, pyrazolinyl, thiazolyl, thiazolinyl, thienyl, furyl, pyranyl, isothiazolyl, isoxazolyl, pyrazinyl, pyridazinyl, pyrrolinyl, or a salt thereof.

3. The benzoheterocyclic compound according to claim 1, wherein R is a group of the formula:

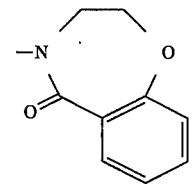

and the unsaturated heterocyclic residue for A is imidazolyl, pyrrolyl, imidazolinyl, pyridyl, pyrimidinyl, oxazolyl, pyrazolyl, pyrazolinyl, thiazolyl, thiazolinyl, thienyl, furyl, pyranyl, isothiazolyl, isoxazolyl, pyrazinyl, pyridazinyl, pyrrolinyl, or a salt thereof.

4. The benzoheterocyclic compound according to claim 1, wherein $R^3$ is a lower alkoxy group or a hydroxy-substituted lower alkyl group, or a salt thereof.

5. The benzoheterocyclic compound according to claim 2, wherein A is pyridyl group, or a salt thereof.

6. The benzoheterocyclic compound according to claim 2, wherein A is thiazolyl group, or a salt thereof.

7. The benzoheterocyclic compound according to claim 2, wherein A is thienyl group or furyl group, and R is a group of the formula: —$NHR^4$ or a salt thereof.

8. The benzoheterocyclic compound according to claim 3, wherein A is pyridyl group, thiazolyl group, thienyl group or furyl group, and both $B_1$ and $B_2$ are methylene group, or a salt thereof.

9. The benzoheterocyclic compound according to claim 5, wherein $R^3$ is hydrogen atom, R is a group of the of the formula: —$NHR^4$ $R^2$ is hydrogen atom, oxo group, a lower alkylidene group, a lower alkoxy group, a lower alkenyloxy group, a hydroxy-substituted lower alkoxy group, a lower alkoxycarbonyl-substituted lower alkoxy group, a carboxy-substituted lower alkoxy group, a lower alkylsulfonyloxy-substituted lower alkoxy group, a phthalimide-substituted lower alkoxy group, a group of the formula: —O—D—$(CO)_lNR^4R^5$ (wherein D is a lower alkylene group, l is 0 or 1, $R^4$ and $R^5$ are the same or different and are hydrogen atom, a lower alkyl group, a lower alkanoyl group, a cycloalkyl group, or an amino-substituted lower alkyl group which may optionally have a lower alkyl substituent, or $R^4$ and $R^5$ may combine together with the nitrogen atom to which they bond to form a 5- or 6-membered saturated heterocyclic group which may be intervened or not with a nitrogen atom, an oxygen atom or a sulfur atom, wherein said heterocyclic group may optionally be substituted by a lower alkyl group or a lower alkanoyl group), a lower alkanoyloxy-substituted lower alkyl group, a lower alkoxycarbonyl-substituted lower alkyl group, an amino which may optionally be substituted by a lower alkyl group or a cycloalkyl group, a lower alkylsulfonyloxy-substituted lower alkyl group, a phthalimide-substituted lower alkyl group, an imidazolyl-substituted lower alkyl group, a 1,2,4-triazolyl-substituted lower alkyl group, an amino-substituted lower alkanoyloxy group which may optionally have a lower alkyl substituent, or an imidazolyl-substituted lower alkoxy group, or a salt thereof.

10. The benzoheterocyclic compound according to claim 5, wherein $R^3$ is hydrogen atom, R is a group of the formula: —$NHR^A$ defined in claim 1 ), $R^2$ is a group of the formula: —E—(CO)$_l$NR$^6$R$^7$ (wherein E and I are the same as defined in claim 1, $R^6$ and $R^7$ are the same or different and are hydrogen atom, a lower alkyl group, an amino-substituted lower alkyl group which may optionally have a lower alkyl substituent, or a lower alkanoyl group), or a salt thereof.

11. The benzoheterocyclic compound according to claim 5, wherein $R^3$ is hydrogen atom, R is a group of the formula: —$NHR^A$ $R^2$ is a group of the formula: —E—(CO)$_l$NR$^6$R$^7$ (wherein E and I are the same as defined above, $R^6$ and $R^7$ combine together with the nitrogen atom to which they bond to form a 5- or 6-membered saturated heterocyclic group which may be intervened or not with a nitrogen atom, an oxygen atom or a sulfur atom, wherein said heterocyclic group is pyrrolidinyl, piperidinyl, piperazinyl, morpholino or thiomorphlino, and said heterocyclic group may optionally be substituted by a lower alkyl group, a lower alkanoyl group or a lower alkoxycarbonyl group), or a salt thereof.

12. The benzoheterocyclic compound according to claim 5, wherein $R^3$ is hydrogen atom, R is a group of the formula: —$NHR^A$ $R^2$ is hydroxy group, a carboxy-substituted lower alkyl group or a hydroxy-substituted lower alkyl group, or a salt thereof.

13. The benzoheterocyclic compound according to claim 6, wherein $R^3$ is hydrogen atom, R is a group of the formula: —$NHR^A$ $R^2$ is hydrogen atom, oxo group, a lower alkylidene group, a lower alkoxy group, a lower alkenyloxy group, a hydroxy-substituted lower alkoxy group, a lower alkoxycarbonyl-substituted lower alkoxy group, a carboxy-substituted lower alkoxy group, a lower alkylsulfonyloxy-substituted lower alkoxy group, a phthalimide-substituted lower alkoxy group, a group of the formula: —O—D—(CO)$_l$NR$^4$R$^5$ (wherein D is a lower alkylene group, l is 0 or 1, $R^4$ and $R^5$ are the same or different and are hydrogen atom, a lower alkyl group, a lower alkanoyl group, a cycloalkyl group, or an amino-substituted lower alkyl group which may optionally have a lower alkyl substituent, or $R^4$ and $R^5$ may combine together with the nitrogen atom to which they bond to form a 5- or 6-membered saturated heterocyclic group which may be intervened or not with a nitrogen atom, an oxygen atom or a sulfur atom, wherein said heterocyclic group may optionally be substituted by a lower alkyl group or a lower alkanoyl group), a lower alkanoyloxy-substituted lower alkyl group, a lower alkoxycarbonyl-substituted lower alkyl group, an amino which may optionally be substituted by a lower alkyl group or a cycloalkyl group, a lower alkylsulfonyloxy-substituted lower alkyl group, a phthalimide-substituted lower alkyl group, an imidazolyl-substituted lower alkyl group, a 1,2,4-triazolyl-substituted lower alkyl group, an amino-substituted lower alkanoyloxy group which may optionally have a lower alkyl substituent, or an imidazolyl-substituted lower alkoxy group, or a salt thereof.

14. The benzoheterocyclic compound according to claim 6, wherein $R^3$ is hydrogen atom, R is a group of the formula: —$NHR^A$ $R^2$ is a group of the formula: —E—(CO)$_l$NR$^6$R$^7$ (wherein E and I are the same as defined in claim 1, $R^6$ and $R^7$ are the same or different and are hydrogen atom, a lower alkyl group, an amino-substituted lower alkyl group which may optionally have a lower alkyl substituent, or a lower alkanoyl group), or a salt thereof.

15. The benzoheterocyclic compound according to claim 6, wherein $R^3$ is hydrogen atom, R is a group of the formula: —$NHR^A$ $R^2$ is a group of the formula: —E—(CO)$_l$NR$^6$R$^7$ (wherein E and I are the same as defined above, $R^6$ and $R^7$ combine together with the nitrogen atom to which they bond to form a 5- or 6-membered saturated heterocyclic group which may be intervened or not with a nitrogen atom, an oxygen atom or a sulfur atom, wherein said heterocyclic group is pyrrolidinyl, piperidinyl, piperazinyl, morpholino or thiomorphlino, and said heterocyclic group may optionally be substituted by a lower alkyl group, a lower alkanoyl group or a lower alkoxycarbonyl group), or a salt thereof.

16. The benzoheterocyclic cyclic compound according to claim 6, wherein $R^3$ is hydrogen atom, R is a group of the formula: —$NHR^A$ $R^2$ is hydroxy group, a carboxy-substituted lower alkyl group or a hydroxy-substituted lower alkyl group, or a salt thereof.

17. The benzoheterocyclic compound according to any one of claims 9 to 16, wherein $R^A$ is a group of the formula:

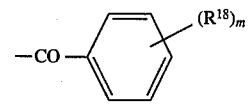

(in which $R^{18}$ is a lower alkyl group or a halogen atom, and m is 1), or a salt thereof.

18. The benzoheterocyclic compound according to any one of claims 9 to 16, wherein $R^A$ is a group of the formula:

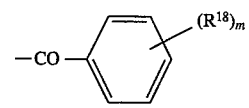

(in which $R^{18}$ is hydrogen atom, a lower alkoxy group, nitro group, a lower alkoxycarbonyl group, carboxy group, a lower alkoxycarbonyl-substituted lower alkoxy group, a hydroxy-substituted lower alkoxy group, a carboxy-substituted lower alkoxy group, a lower alkylsulfonyloxy-substituted lower alkoxy group, a phthalimide-substituted lower alkoxy group, or a group of the formula: —O—E—(CO)$_l$NR$^{19}$R$^{20}$ (E and I are the same as defined above, $R^{19}$ and $R^{20}$ are the same or different and are hydrogen atom or a lower alkyl group, or $R^{19}$ and $R^{20}$ may combine together with the nitrogen atom to which they bond to form a 5- or 6-membered saturated heterocyclic group which may be intervened or not with a nitrogen atom or an oxygen atom, wherein said heterocyclic group may optionally be substituted by a lower alkyl group, or an amino group which may optionally be substituted by a lower alkanoyl group), and m is 1), or a salt thereof.

19. The benzoheterocyclic compound according to any one of claims 9 to 16, wherein $R^A$ is a group of the formula:

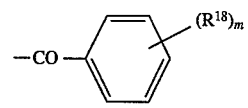

(in which $R^{18}$ is the same as defined in claim 1, and m is 2 or 3), or a salt thereof.

20. The benzoheterocyclic compound according to any one of claims 9 to 16 wherein $R^A$ is thienylcarbonyl group, a cycloalkylcarbonyl group or a phenyl-lower alkanoyl group which may optionally have a lower alkyl substituent on the phenyl ring, or a salt thereof.

21. The benzoheterocyclic compound according to claim 1, which is 7-chloro-5-[N-methyl-N-( 2-diethylaminoethyl)amino]carbonylmethyl-1-[6-( 2-methylbenzoylamino)nicotinoyl]-2,3,4,5-tetrahydro- 1H-benzazepine.

22. The benzoheterocyclic compound according to claim 1, which is 7-chloro-5-carboxymethyl-1-[6-( 2-bromobenzoylamino)nicotinoyl]-2,3,4,5-tetrahydro- 1H-benzazepine.

23. The benzoheterocyclic compound according to claim 1, which is 7-chloro-5-(2-hydroxyethyl)-1-[6-( 2-methylbenzoylamino )nicotinoyl]-2,3,4,5-tetrahydro- 1H-benzazepine.

24. The benzoheterocyclic compound according to claim 1, which is 7-chloro-5-(2-acetylaminoethyl)-1-[ 6-(2-methylbenzoylamino)nicotinoyl]- 2,3,4,5-tetrahydro-1H-benzazepine.

25. The benzoheterocyclic compound according to claim 1, which is 7-chloro-5-hydroxy-1-[5-(2-methylbenzoylamino)- 2-thiazolylcarbonyl]-2,3,4,5-tetrahydro- 1H-benzazepine.

26. An vasopressin antagonist, which comprises as an active ingredient a benzoheterocyclic compound as set forth in claim 1, or a pharmaceutically acceptable salt thereof, in admixture with a pharmaceutically acceptable carrier or diluent.

27. An oxytocin antagonist, which comprises as an active ingredient a benzoheterocyclic compound as set forth in claim 1, or a pharmaceutically acceptable salt thereof, in admixture with a pharmaceutically acceptable carrier or diluent.

28. The benzoheterocyclic compound according to claim 5, wherein $R^3$ is a hydrogen atom, $R^2$ is a group of the formula:

$$-O-D(CO)_R NR^4 S^5$$

wherein R is a group of the formula:

$$-NHR^A$$

wherein $R^A$ is a group of the formula:

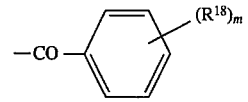

in which $R^{18}$ is a lower alkyl group or a halogen atom, and m is 1, or a salt thereof.

29. The benzoheterocyclic compound according to claim 1, which is 7-chloro-5-(2-cyclopentylaminoethoxy)- 1-[6-(2-chlorobenzoylamino)-nicotinoyl]-2,3,4,5-tetrahydro-1H-benzazepine.

* * * * *